(12) United States Patent
Wang et al.

(10) Patent No.: US 10,725,054 B2
(45) Date of Patent: Jul. 28, 2020

(54) PROTEIN BIOMARKERS FOR ACUTE, SUBACUTE AND CHRONIC TRAUMATIC INJURIES OF THE CENTRAL NERVOUS SYSTEM

(71) Applicants: UNIVERSITY OF FLORIDA RESEARCH FOUNDATION, INCORPORATED, Gainesville, FL (US); THE RESEARCH FOUNDATION FOR STATE UNIVERSITY OF NEW YORK, Albany, NY (US)

(72) Inventors: Kevin Ka-Wang Wang, Gainesville, FL (US); Zhihui Yang, Gainesville, FL (US); Ahmed Moghieb, Richland, WA (US); Richard Rubenstein, Staten Island, NY (US)

(73) Assignees: University of Florida Research Foundation, Incorporated, Gainesville, FL (US); The Research Foundation For The State University of New York, Albany, NY (US)

( * ) Notice: Subject to any disclaimer, the term of this patent is extended or adjusted under 35 U.S.C. 154(b) by 0 days.

(21) Appl. No.: 15/308,934

(22) PCT Filed: Apr. 8, 2015

(86) PCT No.: PCT/US2015/024880
§ 371 (c)(1),
(2) Date: Nov. 4, 2016

(87) PCT Pub. No.: WO2015/157390
PCT Pub. Date: Oct. 15, 2015

(65) Prior Publication Data
US 2017/0146555 A1    May 25, 2017

Related U.S. Application Data

(60) Provisional application No. 61/976,733, filed on Apr. 8, 2014.

(51) Int. Cl.
*G01N 33/68* (2006.01)
(52) U.S. Cl.
CPC ..... *G01N 33/6896* (2013.01); *G01N 33/6893* (2013.01); *G01N 2800/28* (2013.01); *G01N 2800/40* (2013.01); *G01N 2800/56* (2013.01); *G01N 2800/60* (2013.01)
(58) Field of Classification Search
CPC ........... G01N 33/6896; G01N 2800/28; G01N 2800/56; G01N 33/6893; G01N 2800/40; G01N 2800/60
See application file for complete search history.

(56) References Cited

U.S. PATENT DOCUMENTS

| | | | |
|---|---|---|---|
| 2004/0030258 | A1 | 2/2004 | Williams et al. |
| 2004/0091942 | A1 | 5/2004 | Vanmechelen et al. |
| 2009/0263824 | A1* | 10/2009 | Lee ..................... G01N 33/6896 435/7.1 |
| 2010/0136573 | A1 | 6/2010 | Petrucelli et al. |
| 2013/0022982 | A1 | 1/2013 | Wang et al. |

FOREIGN PATENT DOCUMENTS

| | | |
|---|---|---|
| WO | 2005117550 A2 | 12/2005 |
| WO | WO 2011/032155 | 3/2011 |
| WO | 2013119673 A1 | 8/2013 |

OTHER PUBLICATIONS

Billingsley et al. Regulated phosphorylation and dephosphorylation of tau protein: effects on microtubule interaction, intracellular trafficking and neurodegeneration. Biochem J. May 1, 1997;323 ( Pt 3):577-91.*
Riemenschneider et al. Phospho-tau/total tau ratio in cerebrospinal fluid discriminates Creutzfeldt-Jakob disease from other dementias. Mol Psychiatry. Mar. 2003;8(3):343-7.*
Moisse et al. Divergent patterns of cytosolic TDP-43 and neuronal progranulin expression following axotomy: implications for TDP-43 in the physiological response to neuronal injury. Brain Res. Jan. 16, 2009;1249:202-11. doi: 10.1016/j.brainres.2008.10.021. Epub Nov. 1, 2008.*
Kondo et al. Antibody against early driver of neurodegeneration cis P-tau blocks brain injury and tauopathy. Nature. Jul. 23, 2015; 523(7561):431-436. doi: 10.1038/nature14658. Epub Jul. 15, 2015.*
Knoblach, S. M. et al. "Proteases in Traumatic Brain Injury" *Proteases in the Brain*, 2005, pp. 79-108 vol. 3, Chapter 4.
Yang, Z. et al. "Dual vulnerability of TDP-43 to calpain and caspase-3 proteolysis after neurotoxic conditions and traumatic brain injury" *Journal of Cerebral Blood Flow & Metabolism*, Jun. 11, 2014, pp. 1-9, vol. 34, No. 9.
Written Opinion in International Application No. PCT/US2015/024880, dated Jul. 20, 2015, pp. 1-8.
Notice of the First Office Action dated Jan. 10, 2018 in corresponding Chinese Patent Application No. 201580030441.9.

(Continued)

*Primary Examiner* — Gregory S Emch
(74) *Attorney, Agent, or Firm* — Timothy H. Van Dyke; Beusse, Wolter, Sanks & Maire PLLC

(57) ABSTRACT

Proteins that are differentially expressed or elevated in tissue and biofluids after central nervous system injuries are described. Elevated or reduced levels of the proteins, alone or in various combinations or ratios, can be used to assess severity of central nervous system injury (CNS injury) including traumatic brain injury (TBI), traumatic spinal cord injury (SCI) and chronic traumatic encephalopathy (CTE). Time course measurements post CNS-injury of these proteins can be used to monitor progress or recovery over periods up to several months. Differentiation of acute, subacute and chronic injury can be diagnosed by comparing the protein levels in CNS-injury patients at days 1-3, day 4-10 with levels at day 30-180 in comparison with normal controls.

16 Claims, 39 Drawing Sheets

(56) References Cited

OTHER PUBLICATIONS

Stein, T.D., et al., Chronic Traumatic Encephalopathy: a spectrum of neuropathological changes following repetitive brain trauma in athletes and military personnel, Alzheimer's Research & Therapy, 2014, 6:4.

Partial Supplementary European Search Report dated Nov. 24, 2017 in corresponding European Patent Application No. 15776837.5.

Stein et al., "Chronic Traumatic Encephalopathy: a spectrum of neuropathological changes following repetitive brain trauma in athletes and military personnel," Alzheimer's Research & Therapy, Jan. 15, 2014, vol. 6, No. 1, pp. 2-11.

Yang et al., "Dual Vulnerability of TDP-43 to calpain and caspase-3 proteolysis after neurotoxic conditions and traumatic brain injury," Journal of Cerebral Blood Flow & Metabolism, Sep. 1, 2014; vol. 34, No. 9, pp. 1444-1452.

McKee, et al., "The spectrum of disease in chronic traumatic encephalopathy," Brain, vol. 136, No. 1, Dec. 2, 2012, pp. 43-64.

Mondello, S et al., "Serum Concentrations of Ubiquitin C-Terminal Hydrolase-L1 and Glial Fibrillary Acidic Protein after Pediatric Traumatic Brain Injury", Scientific Reports, Jun. 20, 2016, 8 pages.

Neselius, S et al. , "Increased CSF Levels of Phosphorylated Neurofilament Heavy Protein following Bout in Amateur Boxers", Plos One, Nov. 2018, vol. 8, Issue 11, pp. 1-5.

Wang, Shu-Yi et al., "Metabolic syndrome and its components with neuron-specific enolase: a crosssectional study in large health check-up population in China", BMJ Open, 2018, 8 pages.

Boutte, et al., Serum Glial Fibrillary Acidic Protein Predicts tissue glial fibrillary acidic protein break-down products and therapeutic efficacy after penetrating ballistic-like brain injury, "J. of Neurotrauma", vol. 33 pp. 147-156 (2016).

Caccamo, et al. "Cognitive Decline Typical of Frontotemporal Lobar Degeneration in Transgenic Mice Expressing the 25-kDA C-Terminal Fragment of TDP-43", The American Journal of Pathology, 2012, pp. 293-302, vol. 180, No. 1.

Chinese Third Office Action dated Jun. 4, 2019 in corresponding CN Application No. 20150030441.9, pp. 1-9.

DeKosky, et al., "Acute and Chronic Traumatic Encephalophthies: pathogenesis and biomarkers", Nat. Rev. Neurol., 2013, pp. 192-200, vol. 9.

Kanazawa, et al., "Biochemical and histopathological alterations in TAR DNA—binding protein—43 after acute ischemic stroke in rates", Journal of Neurochemistry, 2011, pp. 957-965, vol. 116.

Luo, Jian et al., "Long-term cognitive impairments and pathological alterations in a mouse model of repetitive mild traumatic brain injury", Frontiers in Neurology, Feb. 2014, vol. 5, Article 12, 13 pages.

Chinese Fourth Office Action dated Feb. 12, 2020 in corresponding CN Application No. 20150030441.9, pp. 1-9.

* cited by examiner

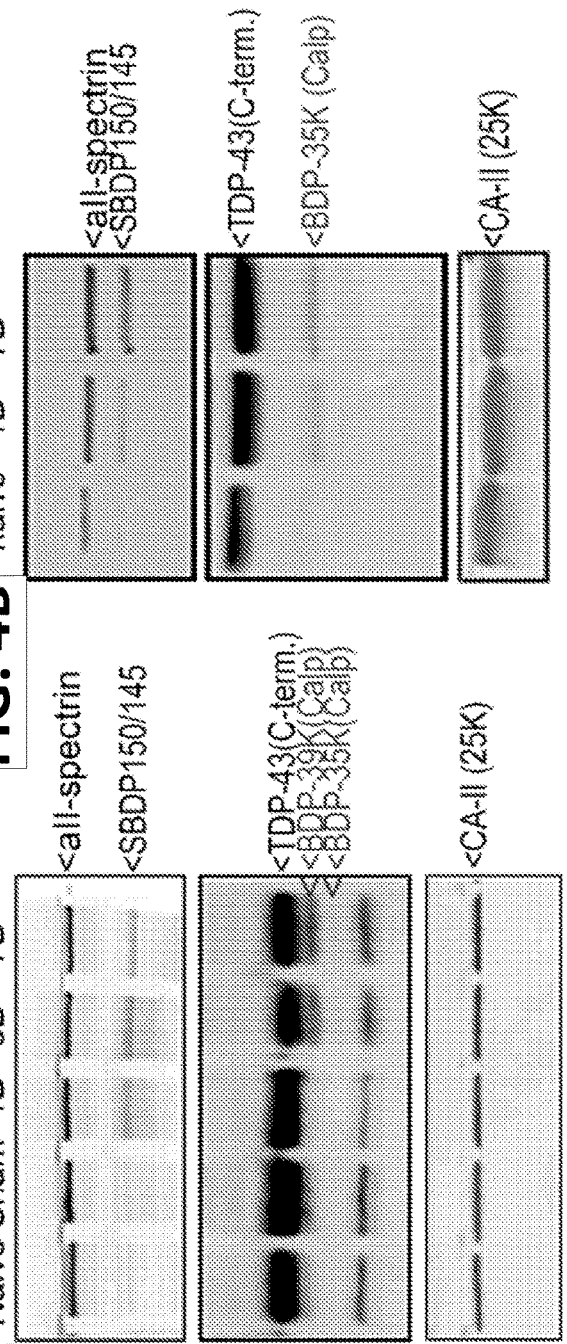
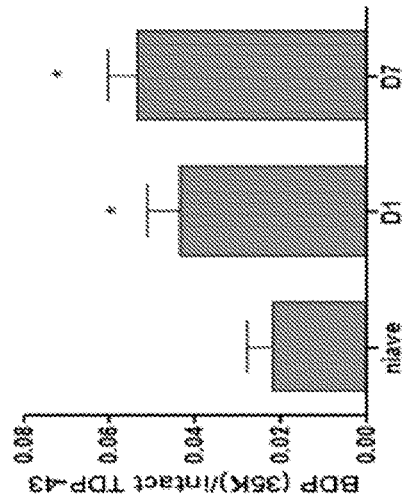
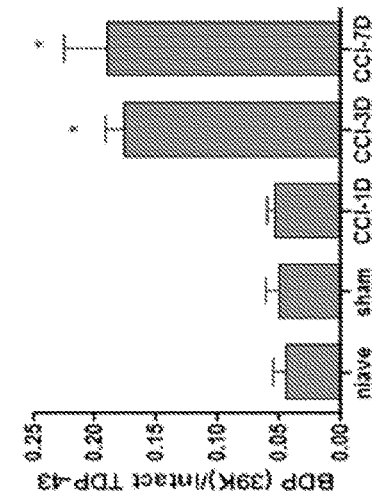
FIG. 4A  FIG. 4B  FIG. 4C  FIG. 4D

FIG. 27

| Table 1. A list of new protein biomarkers for acute, subacute and/or chronic traumatic brain injury and spinal cord injury described in this document | | |
|---|---|---|
| Protein short name | Protein full name | Accession number (human protein) |
| Tau (MAPT) and P-Tau | Microtubule associated Tau protein (Phosphorylated Tau protein) | NP_005901 |
| TDP-43 & BDPs | TAR DNA-binding protein 43 (and its breakdown products) | NM_007375.3 |
| SBDPs (SBDP150, SBDP145, SBDP120, SNTF) | αII-spectrin breakdown products of 150, 145 and 120 kDa and N-terminal spectrin fragment (~140kDa) | NP_003118 |
| GFAP | Glial fibrillary acidic protein (and its breakdown products) (Gfap-α (Isoform 1), Gfap-δ /GFAP-ε (Isoform 2), Gfap-κ (Isoform 3) | NP_002046.1 NP_001124491.1 NP_001229305.1 |
| S100b | Glial S100b protein | NP_006263 |
| MBP | Myelin basic proteins (21K, 18.5, 17K, 14K) | NP_002376, CAG46717, AAH08749, |
| IL-6 | Interleukin-6 | P05231.1 |
| Iba-1 | ionized calcium-binding adapter molecule-1 (Pother name: AIF1 Allograft inflammatory factor 1) in microglia cells, macrophages | BAA13088 |
| VSNL1 / VISL1 | Visinin-Like Protein 1, Hippocalcin-like protein 3, (Other names VILIP, VLP-1, HLP3) | P62760 |
| VSNL2/ HPCAL4 | Hippocalcin-like protein 4, (Other name VILIP-2) | Q9UM19 |
| VSNL3/VILIP-3/HACAL1 | Hippocalcin-like protein 1, (Other name VILIP-3, BDP1) | P37235 |
| Pro-BDNF | Proprotein form of Brain-derived neurotrophic factor (precursor protein) | P23560.1 |
| BDNF | Brain-derived neurotrophic factor (mature form) | P23560.1 |
| Transferrin (TF) | Transferrin precursor | AAA61140 |
| CathD (CTSD) | Cathepsin D / cathepsin D preproprotein | NP_001900 |
| TPI-1 | Triosephosphate isomerase 1 | AAH17917.1 |
| PEA-15 | Phosphoprotein enriched in astrocytes 15 | AAH22554.1 |

FIG. 28

Table 2. Identification of Differentially Expressed Proteins of sham and SCI rat lysate (24h) using CAX-PAGE/RPLC-MSMS platform.

| Band | Protein name | Accession Number (protein / gene) | Gel $M_r$ (KDa) | Intact $M_r$ (KDa) | 24h-Sham unique peptides # | 24h-sham sequence coverage % | 24h-Injured unique peptides # | 24h-Injured sequence coverage % | (up-/down regulated) |
|---|---|---|---|---|---|---|---|---|---|
| 5A | Glyceraldehyde-3-phosphate dehydrogenase | sp\|P04797\|G3P_RAT | 38 | 35 | 5 | 19% | 8 | 32% | ← |
|  | Protein Akr1c1 (aldo-keto reductase family 1, member C-like) | tr\|D3ZF77\|D3ZF77_RAT |  | 37 | 0 | 0% | 5 | 27% |  |
|  | Alcohol dehydrogenase [NADP(+)] | sp\|P51635\|AK1A1_RAT |  | 36 | 0 | 0% | 5 | 23% |  |
|  | Annexin A2 | sp\|Q07936\|ANXA2_RAT |  | 38 | 10 | 30% | 17 | 55% |  |
| 5B | Triosephosphate isomerase (TIM) | sp\|P48500\|TPIS_RAT | 27 | 26 | 0 | 0% | 12 | 68% |  |
| 6A | Aldh4a1 protein (Fragment) | tr\|B4F768\|B4F768_RAT | 60 | 63 | 0 | 0 | 5 | 12% |  |
|  | Pgm1 protein (Fragment) | tr\|A1A5L2\|A1A5L2_RAT |  | 61. | 5 | 12% | 19 | 39% |  |
| 6C | Glutathione S-transferase Mu 1 | sp\|P04905\|GSTM1_RAT | 27 | 26 | 0 | 0% | 6 | 34% |  |
|  | Triosephosphate isomerase (TIM) | sp\|P48500\|TPIS_RAT |  | 27 | 7 | 41% | 14 | 68% |  |
| 11B | Glutathione S-transferase Mu 1 | sp\|P04905\|GSTM1_RAT | 26 | 25 | 6 | 36% | 7 | 44% |  |
|  | Glutathione S-transferase Mu 5 | sp\|Q9Z1B2\|GSTM5_RAT |  | 26 | 7 | 41% | 8 | 53% |  |
| 13A | Serotransferrin (Transferrin) | sp\|P12346\|TRFE_RAT | 75 | 76 | 31 | 52% | 52 | 65% |  |
| 14A | Serotransferrin (Transferrin) | sp\|P12346\|TRFE_RAT | 76 | 76 | 27 | 43% | 34 | 52% |  |
| 14B | LOC367586 protein | tr\|Q5M7V3\|Q5M7V3_RAT | 50 | 51 | 0 | 0% | 8 | 24% |  |
| 14C | Aminoacylase-1A | sp\|Q6AYS7\|ACY1A_RAT | 45 | 45 | 8 | 24% | 11 | 34% |  |
| 18A | Transketolase | sp\|P50137\|TKT_RAT | 70 | 68 | 0 | 0% | 5 | 14% |  |
| 18B | Nucleoside diphosphate kinase A | sp\|Q05982\|NDKA_RAT | 18 | 17 | 0 | 0% | 5 | 45% |  |
|  | Stathmin | sp\|P13668\|STMN1_RAT |  | 17 | 0 | 0% | 5 | 25% |  |
| 20A | Gamma-enolase | sp\|P07323\|ENOG_RAT | 50 | 47 | 9 | 36% | 15 | 59% |  |
| 22A | Elongation factor 2 | sp\|P05197\|EF2_RAT | 85 | 95 | 11 | 13% | 21 | 32% |  |
|  | Phosphorylase | tr\|B1WBU9\|B1WBU9_RAT |  | 97 | 8 | 9% | 12 | 18% |  |
|  | Cytoplasmic aconitate hydratase | tr\|G3V6S2\|G3V6S2_RAT |  | 98 | 7 | 8% | 11 | 17% |  |
| 23A | Protein Tln1 | tr\|G3V852\|G3V852_RAT | 225 | 269 | 0 | 0% | 5 | 46% |  |
|  | Fatty acid synthase | sp\|P12785\|FAS_RAT |  | 272 | 5 | 61% | 23 | 41% |  |
| 23C | Peroxiredoxin-2 | sp\|P35704\|PRDX2_RAT | 21 | 21 | 7 | 41% | 9 | 53% |  |

FIG. 28(cont.)
Table 2. Continued.

| Band | Protein name | Accession Number (protein / gene) | Gel $M_r$ (KDa) | Intact $M_r$ (KDa) | 24h-Sham unique peptides # | 24h-Sham sequence coverage % | 24h-Injured unique peptides # | 24h-Injured sequence coverage % | (up-/down regulated) |
|---|---|---|---|---|---|---|---|---|---|
| 7A | Annexin A2 | sp\|Q07936\|ANXA2_RAT | 37 | 38 | 17 | 56% | 9 | 26% | |
| 11A | Pgm1 protein (Fragment) | tr\|A1A5L2\|A1A5L2_RAT | 60 | 63 | 19 | 43% | 16 | 35% | |
| 13B | Isocitrate dehydrogenase [NADP] cytoplasmic | sp\|Q8VI04\|ASGL1_RAT | 45 | 46 | 13 | 38% | 11 | 41% | |
| | Mannose-6-phosphate isomerase | sp\|Q68FX1\|MPI_RAT | | 46 | 9 | 32% | 5 | 18% | |
| | Aminoacylase-1A | sp\|Q6AYS7\|ACY1A_RAT | | 45 | 9 | 36% | 0 | 0% | |
| 13C | Pyridoxal kinase | sp\|O35331\|PDXK_RAT | 34 | 35 | 11 | 51% | 8 | 38% | |
| | Ester hydrolase C11orf54 homolog | sp\|Q5U2Q3\|CK054_RAT | | 35 | 5 | 29% | 0 | 0% | |
| 20A | Alpha-enolase | sp\|P04764\|ENOA_RAT | 50 | 47 | 12 | 48% | 10 | 42% | |
| | Rab GDP dissociation inhibitor beta | sp\|P50399\|GDIB_RAT | | 50 | 34 | 75% | 27 | 66% | |
| 20B | Triosephosphate isomerase (TIM) | sp\|P48500\|TPIS_RAT | 26 | 27 | 8 | 42% | 6 | 37% | |
| | Dihydropteridine reductase | sp\|P11348\|DHPR_RAT | | 25 | 12 | 62% | 9 | 57% | |
| | Sepiapterin reductase | sp\|P18297\|SPRE_RAT | | 28 | 7 | 33% | 0 | 0% | |
| | Adenylate kinase 3 | tr\|Q6P2A5\|Q6P2A5_RAT | | 25 | 5 | 30% | 0 | 0% | |
| 20C | Stathmin | sp\|P13668\|STMN1_RAT | 19 | 17 | 5 | 25% | 0 | 0% | |
| | Nucleoside diphosphate kinase A | sp\|Q05982\|NDKA_RAT | | 17 | 9 | 66% | 0 | 0% | |
| 21A | Phosphoglycerate mutase 1 | sp\|P25113\|PGAM1_RAT | 27 | 28 | 20 | 78% | 17 | 74% | |
| 24C | Astrocytic phosphoprotein PEA-15 (PEA-15) | sp\|Q5U318\|PEA15_RAT | 14 | 15 | 6 | 62% | 0 | 0% | |
| | Phosphohistidine phosphatase 1 (Predicted), isoform CRA_a | tr\|D3ZP47\|D3ZP47_RAT | | 14 | 5 | 40% | 0 | 0% | |
| | Protein Pmp2 | tr\|D3ZFG5\|D3ZFG5_RAT | | 14 | 6 | 42% | 0 | 0% | |

FIG. 29

Table 3. Identification of Differentially Expressed Proteins of sham and SCI rat lysate (7 days) using CAX-PAGE/RPLC-MSMS platform.

| Band | Protein name | Accession Number (protein / gene) | Gel $M_r$ (KDa) | Intact $M_r$ (KDa) | 7days-Sham unique peptides # | 7days-Sham sequence coverage % | 7days-Injured unique peptides # | 7days-Injured sequence coverage % | (up-/ down regulated) |
|---|---|---|---|---|---|---|---|---|---|
| 6B | Aldo-keto reductase family 1, member B10 (Aldose reductase) | tr\|Q6AY99\|Q6AY99_RAT | 35 | 35 | 0 | 0% | 6 | 36% | ← |
|  | Annexin A1 | sp\|P07150\|ANXA1_RAT |  | 38 | 0 | 0% | 8 | 37% |  |
|  | Annexin A2 | sp\|Q07936\|ANXA2_RAT |  | 38 | 0 | 0% | 20 | 61% |  |
|  | Glyceraldehyde-3-phosphate dehydrogenase | sp\|P04797\|G3P_RAT |  | 35 | 0 | 0% | 12 | 66% |  |
| 9A | Alcohol dehydrogenase [NADP(+)] | sp\|P51635\|AK1A1_RAT | 36 | 36 | 9 | 32% | 10 | 40% |  |
|  | Annexin A1 | sp\|P07150\|ANXA1_RAT |  | 38 | 0 | 0% | 7 | 23% |  |
|  | Annexin A2 | sp\|Q07936\|ANXA2_RAT |  | 38 | 10 | 35% | 22 | 66% |  |
|  | Glyceraldehyde-3-phosphate dehydrogenase | sp\|P04797\|G3P_RAT |  | 35 | 0 | 0% | 8 | 51% |  |
| 11A | Pyruvate kinase PKM | sp\|P11980\|KPYM_RAT | 65 | 57 | 19 | 47% | 12 | 34% |  |
|  | Catalase | sp\|P04762\|CATA_RAT |  | 59 | 0 | 0% | 10 | 29% |  |
|  | Pgm1 protein (Fragment) | tr\|A1A5L2\|A1A5L2_RAT |  | 61 | 11 | 22% | 20 | 46% |  |
|  | Acyl-CoA synthetase family member 2, mitochondrial | sp\|Q499N5\|ACSF2_RAT |  | 67 | 0 | 0% | 9 | 20% |  |
| 11B | Aspartate aminotransferase, mitochondrial | sp\|P00507\|AATM_RAT | 45 | 47 | 0 | 0% | 7 | 24% |  |
| 11C | Glutathione S-transferase Mu 5 | sp\|Q9Z1B2\|GSTM5_RAT | 26 | 26 | 0 | 0% | 8 | 47% |  |
|  | Protein-L-isoaspartate(D-aspartate) | sp\|P22062\|PIMT_RAT |  | 24 | 0 | 0% | 8 | 49% |  |
|  | Triosephosphate isomerase (TIM) | sp\|P48500\|TPIS_RAT |  | 26 | 10 | 65% | 14 | 74% |  |
| 12A | Serotransferrin | sp\|P12346\|TRFE_RAT | 76 | 76 | 21 | 35% | 27 | 43% |  |
|  | Junction plakoglobin | sp\|Q6P0K8\|PLAK_RAT |  | 81 | 0 | 0% | 5 | 11% |  |
| 12B | Catalase | sp\|P04762\|CATA_RAT | 58 | 59 | 5 | 13% | 5 | 14% |  |
|  | Pyruvate kinase PKM | sp\|P11980\|KPYM_RAT |  | 57 | 31 | 63% | 28 | 64% |  |
| 12C | Aspartate aminotransferase, cytoplasmic | sp\|P13221\|AATC_RAT | 45 | 46 | 11 | 29% | 17 | 55% |  |

FIG. 29(cont.)

Table 3. Continued.

| Band | Protein name | Accession Number (protein / gene) | Gel $M_r$ (KDa) | Intact $M_r$ (KDa) | 7days-Sham unique peptides # | 7days-Sham sequence coverage % | 7days-Injured unique peptides # | 7days-Injured sequence coverage % | (up-/down regulated) |
|---|---|---|---|---|---|---|---|---|---|
| 12C | Cathepsin D | tr\|Q6P6T6\|Q6P6T6_RAT | 45 | 44 | 0 | 0% | 8 | 33% | ← → |
| 12D | Macrophage-capping protein | sp\|Q6AYC4\|CAPG_RAT | 40 | 38 | 0 | 0% | 6 | 30% | |
| | Fructose-bisphosphate aldolase A | sp\|P05065\|ALDOA_RAT | | 39 | 9 | 40% | 15 | 64% | |
| | 3-ketoacyl-CoA thiolase A, peroxisomal | sp\|P21775\|THIKA_RAT | | 43 | 7 | 27% | 10 | 44% | |
| | Cathepsin D | sp\|P24268\|CATD_RAT | | 44 | 0 | 0% | 7 | 24% | |
| 12E | Glutathione S-transferase Yb-3 | sp\|P08009\|GSTM4_RAT | 26 | 25 | 6 | 28% | 8 | 36% | |
| | Triosephosphate isomerase (TIM) | sp\|P48500\|TPIS_RAT | | 26 | 10 | 54% | 16 | 80% | |
| 14A | Serotransferrin (Transferrin) | sp\|P12346\|TRFE_RAT | 76 | 76 | 29 | 47% | 39 | 56% | |
| 5A | Aldo-keto reductase family 1, member B10 (Aldose reductase) | tr\|Q6AY99\|Q6AY99_RAT | 35 | 35 | 0 | 0% | 6 | 29% | |
| | Annexin A2 | sp\|Q07936\|ANXA2_RAT | | 38 | 23 | 63% | 13 | 43% | |
| | Alcohol dehydrogenase [NADP(+)] | sp\|P51635\|AK1A1_RAT | | 36 | 7 | 21% | 0 | 0% | |
| | L-lactate dehydrogenase B chain | sp\|P42123\|LDHB_RAT | | 36 | 7 | 26% | 0 | 0% | |
| | NAD-dependent protein deacetylase sirtuin-2 | sp\|Q5RJQ4\|SIR2_RAT | | 39 | 8 | 27% | 0 | 0% | |
| 6A | Aspartate aminotransferase, cytoplasmic | sp\|P13221\|AATC_RAT | 45 | 46 | 18 | 55% | 10 | 34% | |
| | Fumarylacetoacetase | sp\|P25093\|FAAA_RAT | | 45 | 0 | 0% | 10 | 40% | |
| | Cathepsin D | tr\|Q6P6T6\|Q6P6T6_RAT | | 44 | 5 | 20% | 0 | 0% | |
| 10A | Acyl-CoA synthetase family member 2, mitochondrial | sp\|Q499N5\|ACSF2_RAT | 65 | 67 | 9 | 24% | 5 | 14% | |
| | Pgm1 protein (Fragment) | tr\|A1A5L2\|A1A5L2_RAT | | 61 | 17 | 42% | 15 | 41% | |
| 10B | Protein-L-isoaspartate(D-aspartate) O-methyltransferase | sp\|P22062\|PIMT_RAT | 24 | 24 | 7 | 51% | 0 | 0% | |
| | Ribosyldihydronicotinamide dehydrogenase [quinone] | sp\|Q6AY80\|NQO2_RAT | | 26 | 6 | 34% | 0 | 0% | |
| 22A | ATP citrate lyase, isoform CRA_a | tr\|G3V888\|G3V888_RAT | 125 | 120 | 30 | 41% | 18 | 23% | → |
| 22B | Phosphorylase | tr\|B1WBU9\|B1WBU9_RAT | 102 | 97 | 11 | 17% | 7 | 10% | |
| | Cytoplasmic aconitate hydratase | tr\|G3V6S2\|G3V6S2_RAT | | 98 | 6 | 9% | 10 | 18% | |

FIG. 29(cont.)

| Hexokinase-1 | sp|P05708|HXK1_RAT | 102 | 10 | 11% | 0 | 0% |

FIG. 30

Table 4. Various types of traumatic brain injury biomarkers by categories.

| Marker Type | Biomarkers |
|---|---|
| Acute neuronal injury markers | Neurite injury markers (SBDP/MAP2, NF-H, c-Tau, VSNL-1, BDNF, Pro-BDNF), Cell body injury: UCH-L1, NSE, NMDA-R fragment, TPI-1, Cathepsin D), Demyelination (MBP & fragment), and Gliosis/ Glial cell injury (GFAP & BDP; S100b, PEA-15), Blood brain barrier marker (Transferrin, Aquoporin-4) |
| Neurodegeneration markers | AD / CTE markers (P-tau e.g. T181, S202, T231 and Tau, TDP-43), AD markers (A$\beta$1-40, and A$\beta$1-42), Alpha-synuclein, and Park-7 (DJ-1) |
| Neuroinflammatory markers | Cytokines (IL-6, IL-8; TNF-alpha, and IL-10), Microgliosis (iba-1); Inflammasome, and |
| Neuro-Regeneration markers | Neuro-stem cell markers (Nestin, doublecortin) and Neurite Outgrowth markers (GAP43, CRMPs) |

FIG. 31

Table 5. Various types of traumatic brain injury biomarker entities.

| Name | Description |
|---|---|
| SPTEII | AlphaII-spectrin |
| MAPT | Tau |
| NES | Nestin |
| DCX | Doublecortin |
| SYP | Synaptophysin |
| GHRL | Growth hormone releasing |
| IL 10 | Interleukin 10 |
| IgM | CD40 |
| CRH | Corticotrophin releasing factor |
| COMT | Complement C4 |
| APOE | Apolipoprotein E |
| PPP3CA | Protein phosphatase 3 (PPP3CC) |
| ADORA1 | Adenosine A1 receptor (A1AR) |
| GAD1 | Glutamic acid decarboxylase |
| WWC1 | Kidney and brain expressed protein (KIBRA) |
| BDNF | Brain-derived neurotropic factor |
| NGB | Neuroglobin |
| PARP1 | Poly [ADP-ribose] polymerase 1 |
| TP53 | Tumor protein 53 (p53) |
| MME | Neprilysin (NEP) |
| MTHFR | Methylenetetrahydrofolate reductase (NAD(P)H) |
| SLC6A3 | Dopamine transporter I (DAT1) |
| GFAP | Glial Fibrillary acidic protein |
| AIF-1 | Allograft inflammatory factor-1 |
| CHI3L1 | Chitinase-3 like-1 |
| MBP | Myelin basic protein |
| TSH | Thyroid-stimulating hormone | ism

PROTEIN BIOMARKERS FOR ACUTE, SUBACUTE AND CHRONIC TRAUMATIC INJURIES OF THE CENTRAL NERVOUS SYSTEM

This application is the U.S. national stage application of International Patent Application No. PCT/US2015/024880, filed Apr. 8, 2015, which claims the benefit of U.S. Provisional Application Ser. No. 61/976,733, filed Apr. 8, 2014, the disclosures of which are hereby incorporated by reference in their entirety, including all figures, tables and amino acid or nucleic acid sequences.

This invention was made with government support under X81XWH-12-1-0277 awarded by Department of Defense. The government has certain rights in the invention.

BACKGROUND OF THE INVENTION

1. Field of the Invention

The invention relates generally to the field of biological diagnostics, particularly to methods for diagnosis, prognosis and management of injury or chronic dysfunctions of the central nervous system.

2. Description of Background Art

Traumatic spinal cord injury (SCI) is an injury resulting from an insult inflicted on the spinal cord. It can lead to the loss of sensory and motor after injury, and is an important cause of neurologic disability after trauma, such as lifelong paralysis for SCI patients. It is estimated that approximately 300,000 people in North America are living with a spinal cord injury (SCI), and 12,000 to 20,000 new cases occur annually.

It has been hypothesized that the pathologic process that leads to acute traumatic spinal cord injury consists of two steps; the primary injury results from the physical and mechanical damages that occur as a result of direct impact to the spinal cord. The secondary injury is the cascade of biochemical events such as proteolysis of cytoskeletal, membrane, and myelin proteins due to the elevation in intracellular $Ca^{2+}$ that activates cysteine proteases (e.g. calpain). The proteolysis damages the spinal cord by progressive tissue degeneration, including neuronal cell death, axonal degeneration, and demyelination in the spinal cord. Although it is quite easy to diagnose acute traumatic SCI, assessment of injury severity is often challenging. Neurological examinations are currently used for diagnosis, determination of severity, and prediction of neurologic outcome in the brain injury (TBI, stroke). However, these measures often cannot assess the severity of SCI; in addition, the neurological recovery variability for SCI patients is high. Therefore, the discovery and use of biomarkers for SCI is expected to lead to development of new therapeutic interventions that can be applied to prevent or reduce disability of SCI.

In 2010, about 2.5 million emergency department visits, hospitalizations or deaths were associated with traumatic brain injury (TBI), either alone or in combination with other injuries, in the United States. TBI contributed to the deaths of more than 50,000 people and was diagnosed in more than 280,000 hospitalizations and 2.2 million emergency room visits. The emergencies consisted of TBI alone or TBI in combination with other injuries.

Over the past decade (2001-2010), while rates of TBI related emergency visits increased by 70%, hospitalization rates increased by only 11% and death rates decreased by 7%. In 2009, an estimated 248,418 children ages 20 or younger were treated in the United States. Emergency room visits for sports and recreation related injuries that included a diagnosis of concussion or TBI.3. From 2001 to 2009 the rate of emergency room visits for sports and recreational related injuries with a diagnosis of concussion or TBI, alone or in combination with other injuries, rose 57% among children and young adults.

Chronic Traumatic Encephalopathy (CTE) is a form of encephalopathy that is a progressive degenerative disease resulting from repetitive traumatic brain injury. This type of injury was previously called punch-drunk syndrome or dementia pugilistica. CTE is commonly found in professional athletes participating in contact sports such as boxing, Ruby, American football, ice hockey, and professional wrestling. It has also been found in soldiers exposed to blast or concussive injury.

Symptoms associated with CTE may include dementia such as memory loss, aggression, confusion and depression, which generally appear years or decades after the trauma. Post-mortem findings have found Tau protein (MAFT), TAR DNA-binding protein 43 (TDP-43) and other protein deposits in the brain.

Biomarker is defined according to the National Academy of Sciences, as an indicator that signals events in biological samples or systems. Biomarkers are considered to be extremely valuable unbiased tools to define the severity of SCI because they reflect the extent of the spinal cord damage and predict neurologic recovery. There ire some metabolite candidates such as N-acetyl aspartate (NAA, neuronal/axonal marker), creatine marker), and choline (indicator of cellular turnover related to both membrane synthesis and degradation) that can be used as biomarkers for monitoring the pathobiological changes of primary and secondary damage in SCI using proton magnetic resonance spectroscopy (1H-MRS). In vivo 1H-MRS is a valuable tool for noninvasive monitoring of brain biochemistry by quantifying the changes in the metabolites in brain tissue. However, due to the relatively small size of the spinal cord and magnetic susceptibility effects from the surrounding bony structures, the ability to acquire. MR spectra with adequate signal to noise ratio (SNR) is limited, and this precludes the detection of subtle changes in metabolite levels.

SUMMARY OF THE INVENTION

The present invention identifies and analyzes changes in several protein biomarkers which are associated with acute and chronic injuries to the brain and spinal cord. Differential values of selected proteins for example can distinguish chronic from acute traumatic brain and central nervous system injury. Generally, the invention demonstrates that changes in several different protein levels as well as the ratios of some of the proteins, can provide biomarker based tools for diagnosis, prognosis and management of central nervous system injuries.

Table 1 is a list of new protein biomarkers for acute, subacute and/or chronic traumatic brain injury and spinal cord injury described in this document as identified by proteomics, systems biology and immunological assay methods. Markers include protein short name, protein full name and protein accession number. They include: Tau (MAPT) and P-Tau (Microtubule associated Tau protein (Phosphorylated Tau protein)), TDP-43 & BDPs (TAR DNA-binding protein 43 (and its breakdown products), SBDPs (SBDP150, SBDP145, SBDP120, SNTF) (αII-spectrin breakdown products of 150, 145 and 120 kDa and N-terminal spectrin fragment (~140 kDa), GFAP (Glial fibrillary acidic protein (and its breakdown products) (Gfap-α (Isoform 1), Gfap-δ/GFAP-ε (Isoform 2), Gfap-κ (Isoform 3), S100b (Glial S100b protein), MBP (Myelin basic proteins (21K, 18.5, 17K, 14K), IL-6 (Interleukin-6), Iba-1 (ionized calcium-binding adapter molecule-1 (Other name: AIF1 Allograft inflammatory factor 1) in microglia cells, macrophages), VSNL1/VISL1 (Visinin-Like Protein 1, Hippocalcin-like protein 3 (Other names VILIP, VLP-1, HLP3), VSNL2/HPCAL4 (Hippocalcin-like protein 4, (Other name VILIP-2)), VSNL3/VILIP-3/HACAL1 (Hippocalcin-like protein 1, (Other name VILIP-3, BDP1), Pro-BDNF (Proprotein form of Brain-derived neurotrophic factor (precursor protein)), BDNF (Brain-derived neurotrophic factor (mature form)), Transferrin (TF) (transferrin precursor), CathD (CTSD) (Cathepsin D/cathepsin D prepropro-tein), TPI-1 (Triosephosphate isomerase 1, TIM). PEA-15 (Phosphoprotein enriched in astrocytes 15).

In an important aspect, the invention is a method for diagnosing traumatic spinal cord injury (SCI) severity in a subject. The method encompasses the steps of obtaining a preliminary diagnosis of acute traumatic spinal cord injury; selecting a panel of differentially expressed proteins in spinal cord injured subjects compared to uninjured subjects; measuring levels of said proteins in a first tissue or blood sample from the subject at an initial time up to 1-3 days post injury; repeating measurement of the proteins in tissue or blood samples of the injured subject at selected times post the initial measurements; and comparing the differentially expressed levels of proteins in the injured subject at different times post injury to levels of the proteins in uninjured subjects. Increased protein levels within 1-7 days of injury of any two or more proteins, including aldehyde dehydrogenase-4, Aldh4a1 fragment, LOC367586 protein, aminoacylase 1A, gamma-enolase, elongation factor2, protein Tln1 peroxiredoxin-2, aldo-keto reductase family 1, member B10 (aldose reductase), pyruvate kinase PKM, Acyl-CoA synthetase family member 2, mitochondrial, and protein-L-isoaspartate (D-aspartate O-methyltransferase) or decreased levels of isocitrate dehydrogenase (NADP), mannose-6-phosphate isomerase, pyridoxal kinase, starlimin and peripheral myelin protein 2 (Pmp2), alcohol dehydrogenase (NADF(+)), L-lactate dehydrogenase B chain, ribosyldihy-dronicotinamide dehydrogenase [quinone], and ATP citrate lyase-CRA a isoform compared to levels of the same proteins in healthy subjects is indicative of severe SCI.

Acute or subacute CNS injury is indicated when one or more of the following protein levels compared to healthy subjects is increased within 1-10 days of CNS injury: fatty acid synthase, NME/NM23 nucleoside diphosphate kinase 1, eukaryotic translation elongation factor2, annexin A1, annexin A2, cathepsin D, phosphoglucomutase 1, glutamic-oxaloacetic transaminase 2, mitochondrial (aspartate aminotransferase 2), aldehyde dehydrogenase-4, Aldh4a1 fragment, LOC367586 protein, aminoacylase 1A, gamma-enolase, elongation factor2, protein Tln1 peroxiredoxin-2, aldo-keto reductase family 1, member B10 (aldose reductase), pyruvate kinase PKM, Acyl-CoA synthetase family member 2, mitochondrial, and protein-L-isoaspartate (D-aspartate O-methyltransferase). Such injury is also indicated by decreased levels of isocitrate dehydrogenase (NADP), mannose-6-phosphate isomerase, pyridoxal kinase, stathmin and peripheral myelin protein 2 (Pm2), alcohol dehydrogenase [NADP(+)], L-lactate dehydrogenase B chain, ribosyl-dihydronicotinamide dehydrogenase [quinone], and ATP citrate lyase-CRA a isoform when compared to levels of the same proteins in healthy subjects.

The claimed method also allows distinguishing acute and chronic central nervous system (CNS) injury in a subject from an un-injured control subject by measuring the level of total Tau (T-Tau), phosphorylated (P-Tau) and P-Tau/T-Tau ratio in a biofluid sample such as CSF, blood, serum, or plasma at least once during days 1-3 post trauma; measuring the level of T-Tau, P-Tau and P-Tau/T-Tau ratio in a second sample on or about day 30 to about 180 days post CNS-injury; and comparing the levels of T-Tau, P-Tau and P-Tau/T-Tau ratio in the trauma samples in days 1-3 with a sample from an uninjured or healthy subject. Higher levels of T-Tau, P-Tau and P-Tau/T-Tau ratio in days 1-3 compared to levels in a control sample is indicative of acute CNS injury.

The CNS injury can be traumatic brain injury (TBI), acute spinal cord injury or chronic traumatic encephalopathy (CTE).

The method is particularly useful for diagnosis of central nervous system injury in a subject. Biofluid (e.g. CSF, blood, serum, plasma) levels of one or more of a differentially expressed group of proteins are measured. The proteins are selected from TAR DNA-binding protein 43 (TDP-43) and its breakdown products, Visinin-Like Proteins (VILIP-1, VILIP-2, VILIP-3), Brain-derived neurotrophic factor (BDNF) and precursor of BDNF (Pro-BDNF), ionized calcium-binding adapter molecule-1 (iba-1), total Tau (T-Tau), phosphorylated Tau (P-Tau) and the P-Tau/T-Tau ratio, and transferrin, cathepsin D, TIP-1, and PEA-15. The level of the one or more proteins increased over the same proteins in a healthy subject is indicative of acute or chronic spinal cord injury or traumatic brain injury (TBI).

Preferably, one or more proteins with higher levels are selected from the group of TDP-43, Visinin-Like Proteins, BDNF, Pro-BDNF, iba-1, Tau, P-Tau; P-Tau/T-Tau ratio, transferrin, cathepsin D, TIP-1, and PEA-15 and are measured in combination with one or more proteins selected from the group of GFAP, GFAP-BDP and alphaII-spectrin breakdown products (SBDPs), MBP (21K, 18.5, 17K, 14K isoforms), IL-6; UCH-L1 and S100b. Higher levels of the proteins are compared with levels in the healthy subject and are indicative of MS-injury (spinal cord injury or TBI).

The claimed method is useful for early determination of traumatic brain injury (TBI) or spinal cord injury (SCI). Detection of TDP-43 and TDP-43-BDP in CSF, blood, serum or plasma at levels at least twice as high as in controls is indicative of TBI when measured up to 3 days post injury. The injury can be from cortical impact (severe TBI), concussive closed head injury or blast overpressure-induced brain injury or spinal cord injury.

The protein levels can be measured also from one or more biofluids including not only cerebrospinal fluid (CSF), blood, serum, and plasma, but also saliva, urine nasal fluid and sweat, or from solid biosamples selected from biopsy or autopsy brain or spinal cord tissue samples.

A preferred embodiment is a diagnostic kit which includes a collection of tables showing CNS biosample or biofluid levels of differentially expressed proteins in subjects with central nervous system injuries. The tables are organized with respect to severity of injury and patterns associated with time post injury. The kit also includes instructions for use of each table for type of central nervous system injury, and approximate time post injury for making measurements. A diagnosis of level of CNS severity is determined by comparison of levels of said proteins in an injured patient to the protein levels in the tables.

The central nervous system injury is traumatic brain injury (TBI), traumatic spinal cord injury (SCI) or chronic traumatic encephalopathy (CTE).

The biofluids for analysis can be selected from one or more cerebrospinal fluid (CSF), blood, serum, plasma, saliva, urine nasal fluid, and sweat. Solid biosamples can be collected from biopsy or autopsy brain and/or spinal cord tissue samples.

The one or more of the differentially expressed proteins for diagnosis can be TAR DNA-binding protein 43 (TDP-43) and its breakdown products, Visinin-Like Proteins (VILIP-1, VILIP-2, VILIP-3), Brain-derived neurotrophic factor (BDNF) and precursor of BDNE (Pro-BDNF), ionized calcium-binding adapter molecule-1 (iba-1), total Tau (T-Tau), phosphorylated Tau (P-Tau) and the P-Tau/T-Tau ratio, Transferrin, cathepsin D, phosphoprotein enriched in astrocytes 15 (PEA 15), triosephosphate isomerase 1 (TPI-1).

Additionally, the one or more proteins analyzed can be selected from TDP-43, Visinin-Like Proteins, BDNF, Pro-BDNF, iba-1, Tau, P-Tau, P-Tau/T-Tau ratio, transferrin, cathepsin D, TIP-1, and PEA-15, in combination with one or more proteins selected from GFAP, GFAP-BDP and alphaII-spectrin breakdown products (SBDPs), MBP (21K, 18.5, 17K, 14K isoforms), IL-6, UCH-L1 and S100b.

BRIEF DESCRIPTION OF THE FIGURES

FIGS. 4A-4D show TDP-43 proteolysis in mouse cortex after traumatic brain injury (TBI). The brain samples were collected from naive, sham, ipsilateral cortex of the controlled cortical impacted (CCD mice (1.5 mm impact depth) (A) and the frontal cortex of overpressure blast-wave-induced brain injury (OBI) mice (30 psi peak pressure) (B) at 1.3 days after injury. Brain lysates were subjected to immunoblotting and probed with either C-terminal or internal TDP-43, alphaII-spectrin or carbonic anhydrase II (CA-II) antibodies. Quantitative analysis of the ratio of breakdown product to total TDP-43 in CCI mouse cortex (C) and OBI mouse cortex (D) was done by densitometry analysis. Values represent means±sem., n 4-5. *P<0.05 compared with naive (one-way analysis of variance).

(PEA-15) at 4 h, 24 h and/or 7 d after spinal cord injury. Tissue examples are caudal segment from the injury epicenter. These patterns are consistent with differential mass spectrometry proteomic results. Transferrin, Cathepsin D, TPI-1 and PEA-15 (from left to right bars in each set). *p<0.05 moderate or severe TBI different from respective sham and naïve.

FIGS. 15A-15D show rat spinal cord injury CSF samples shows elevations of novel biomarker Transferrin and TPI-1 that have comparable patterns to known neurotrauma biomarkers (SBDPs and GFAP and GFAP BDPs). (A) images of immunoblots, (B) Transferrin (left bars), TPI-1 (right bars), (C) alphaII-spectrin, SBDP150, SBDP145 and SBDP120 (bars form left to right), (D) GFAP-50K (intact, GFAP-BDP-44K, GFAP-BDP-38K (bars from left to right). *p<0.05 moderate or severe SBI different from respective sham and naïve.

Figure 16:
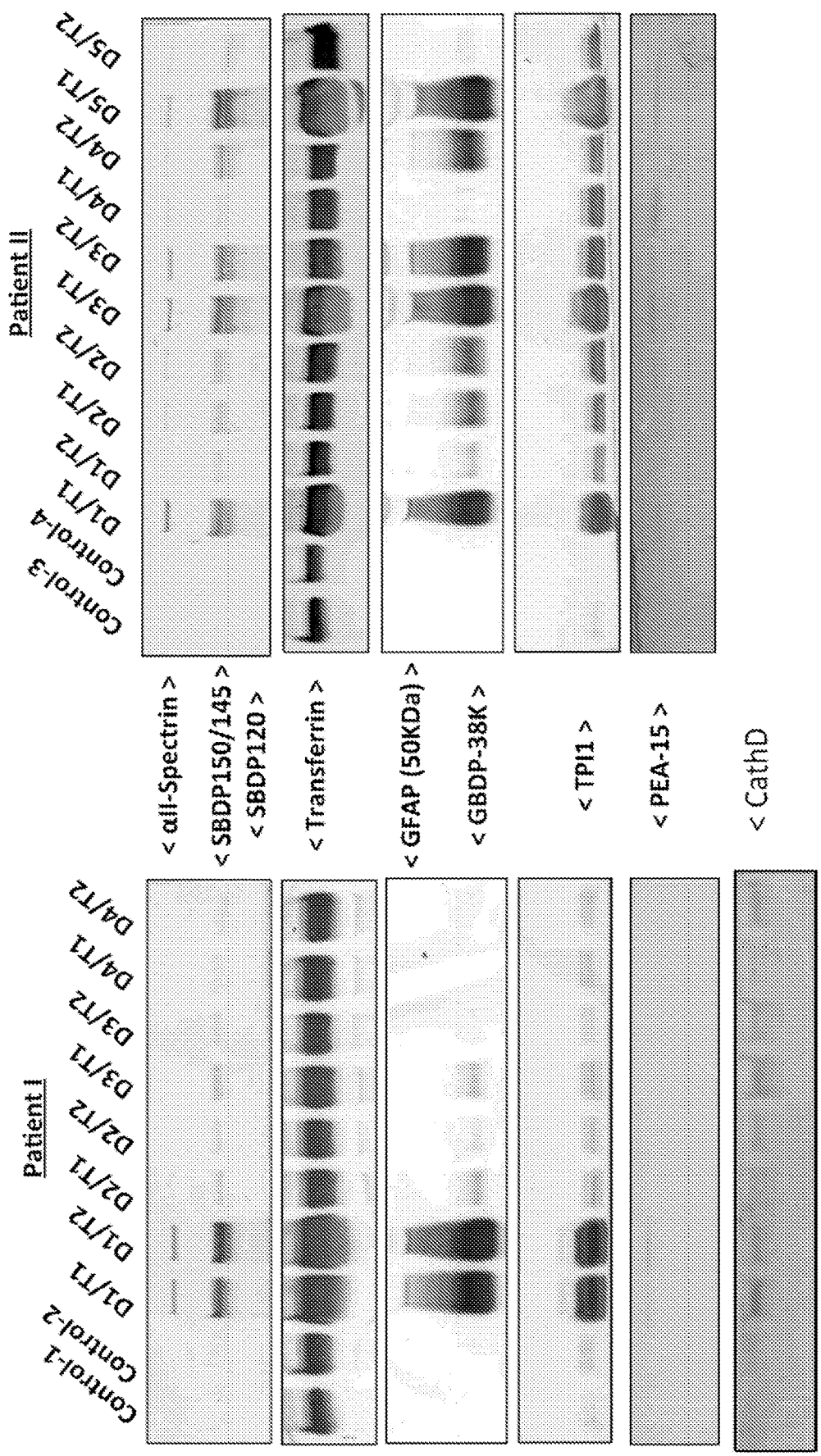

FIG. 16 are examples of human spinal cord injury CSF samples shows elevations of novel biomarker Transferrin, CathD, TPI-1, and PEA-15, as well as other biomarkers previously identified in TBI (SBDPs, GFAP and GFAP-BDPs). Shown are two control CSF samples and serial CSF samples from two SCI patients (from Day 1 time point 1, time point 2 to up to day 5 time point 2).

Figure 8A:
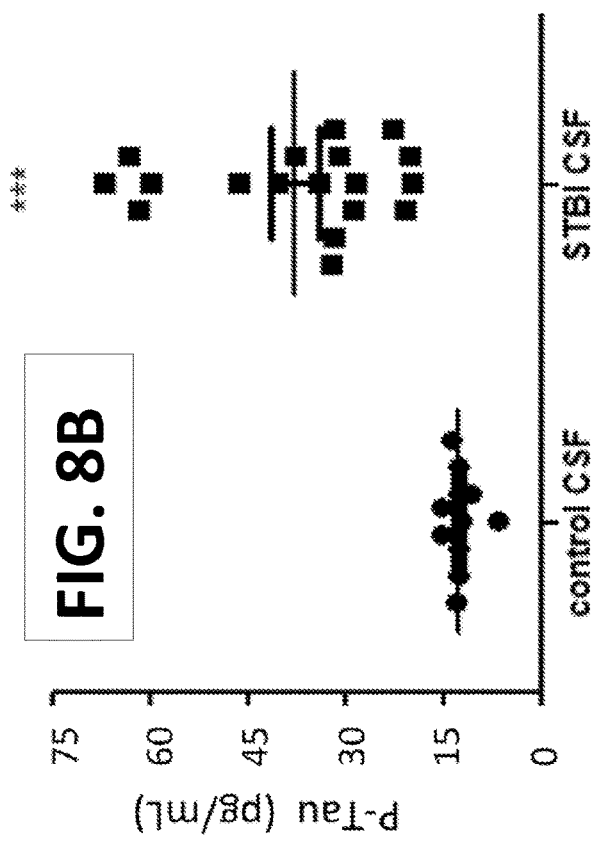
FIGS. 8A-8C. Human CSF T-Tau, P-Tau and P-Tau/T-Tau detection of acute TBI Healthy Control vs. acute severe. TBI (first 24-72 h). (A). Total rau, (B) P-tau and (C) P-Tau/Total-Tau ratio are plotted, *p<0.05 different from control, ***, p<0.001 different from control.
Figure 8B:
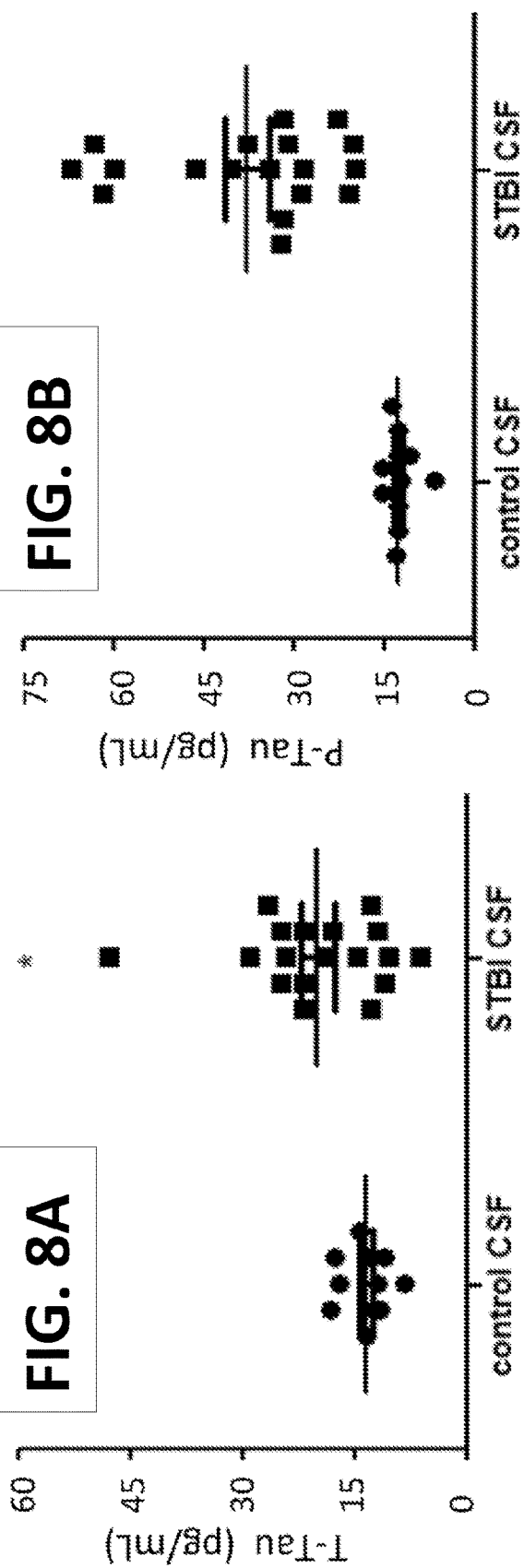
Figure 8C:
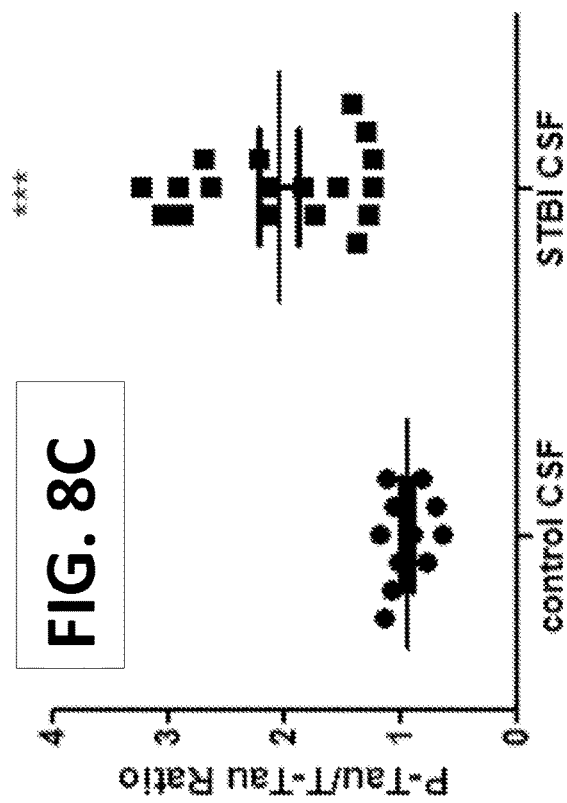
Figure 17A:
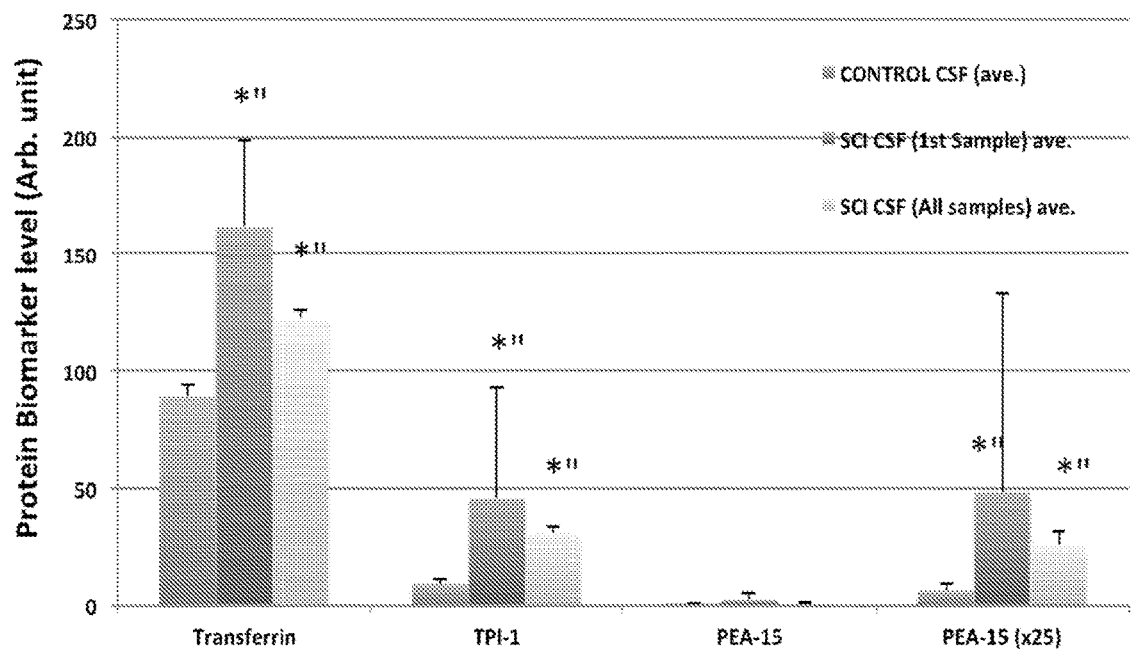

FIGS. 17A-17I8 show human spinal cord injury CSF samples shows elevations of novel biomarker Transferrin and TPI 1 PEA-15 (A) that have comparable patterns to known neurotrauma biomarkers (SBDPs and GFAP and GFAP-BDPs) (B). SCI patient CSF samples are collected from first day (day 0) to day 6 after injury. Shown here are 1$^{st}$ sample signals and all samples from patients (SCI n=12-15, control 10-12. (A & B) Control CSF, SCI CSF (1$^{st}$ sample), SCI CSF (all samples) (from left to right bars in each set). *p<0.05 SCI different from Control CSF.

Figure 18:
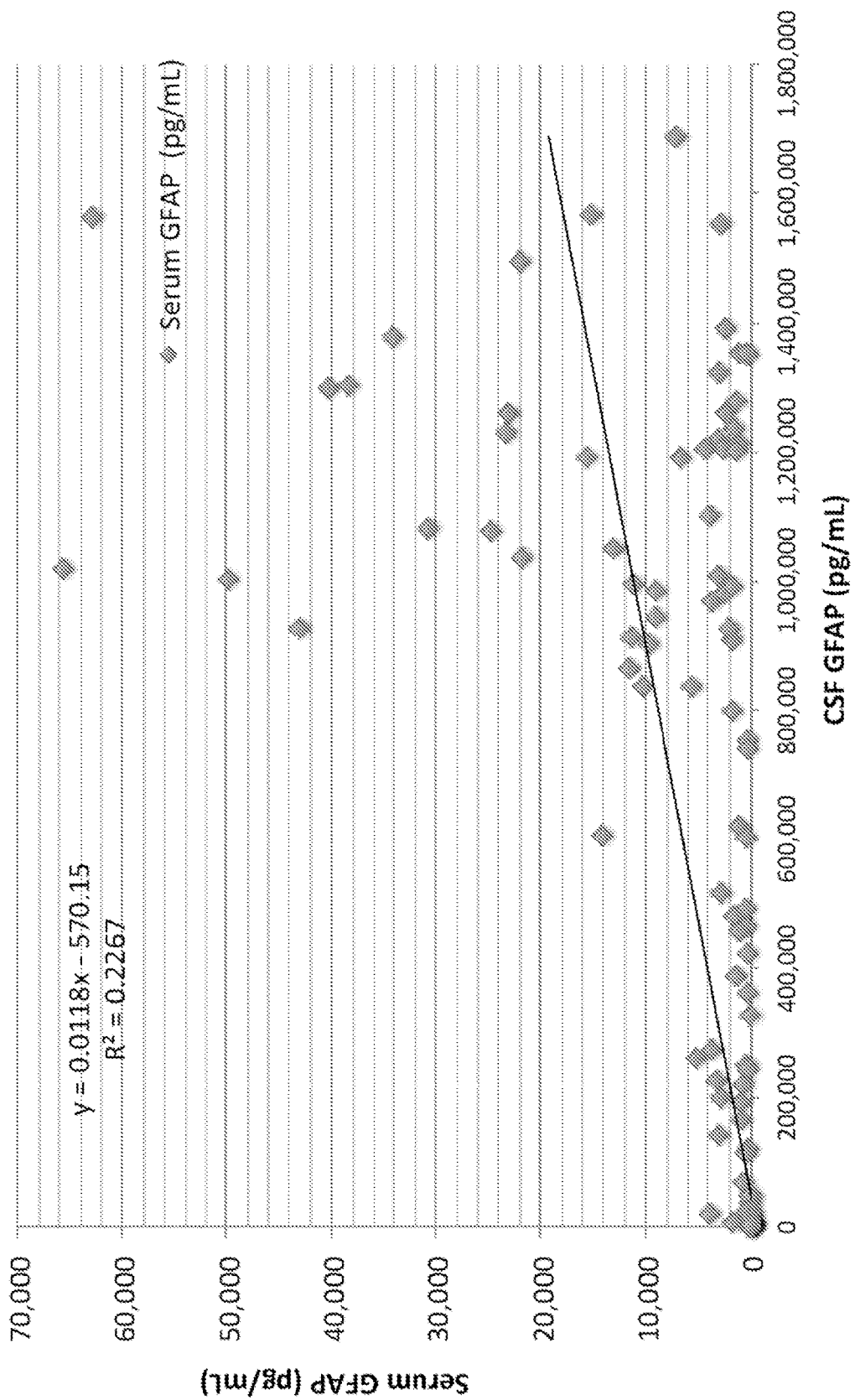

FIG. 18 shows human spinal cord injury CSF and serum GFAP levels from wine subject at same time points showing a correlation. Human SCI subjects n=12, with serial CSF and serum collected every 6 h from day 0-6. The GFAP levels in CSF are about 10-100 higher than those found in serum. Thus we in that if biomarkers are shown to be elevated in human CSF samples they are expected to be elevated in blood (e.g. serum, plasma samples) in a quantifiable manner.

Figure 19:
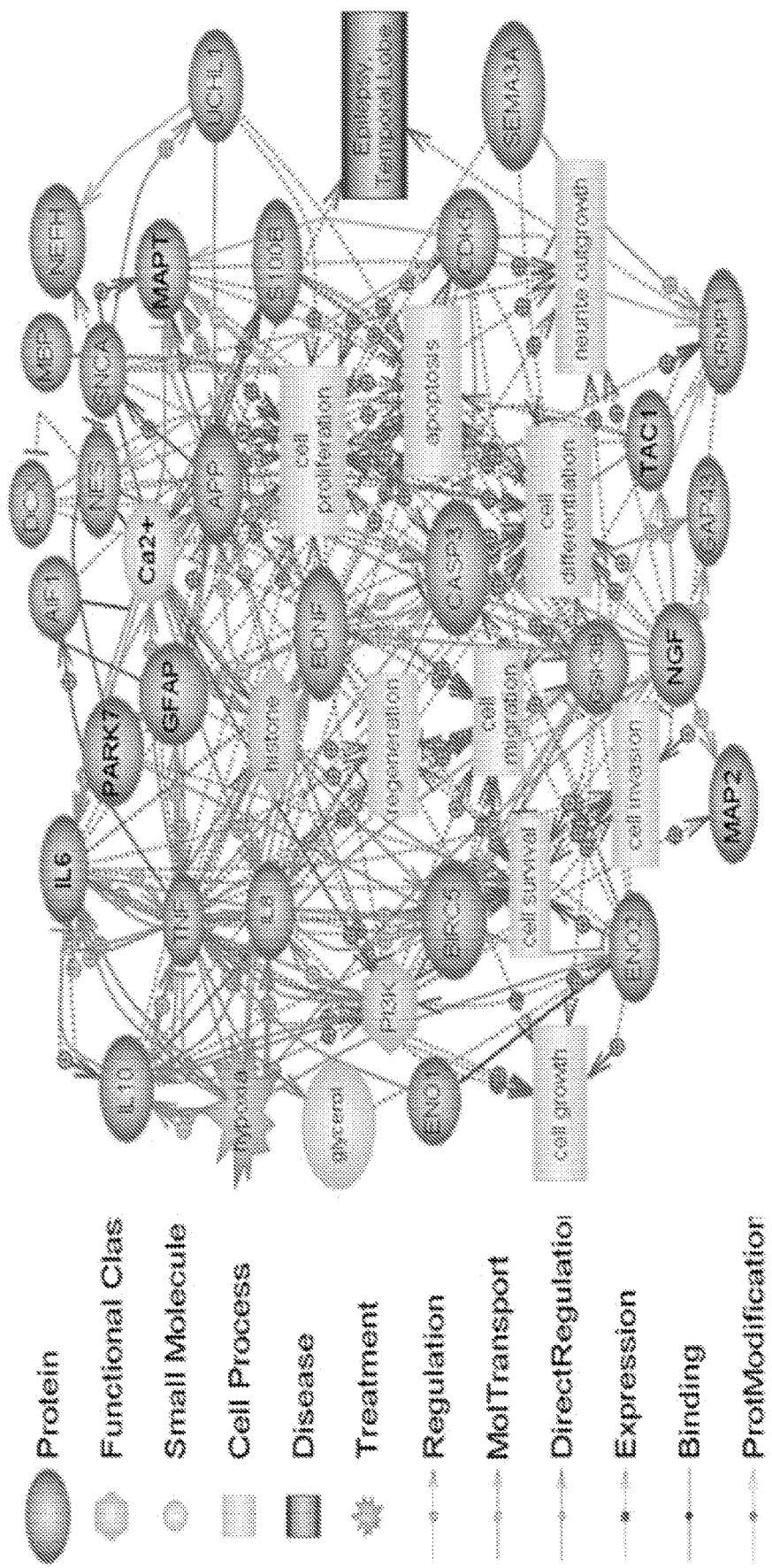

FIG. 19 is a systems biology mapping of interactome of various TBI biomarker types.

Figure 20:
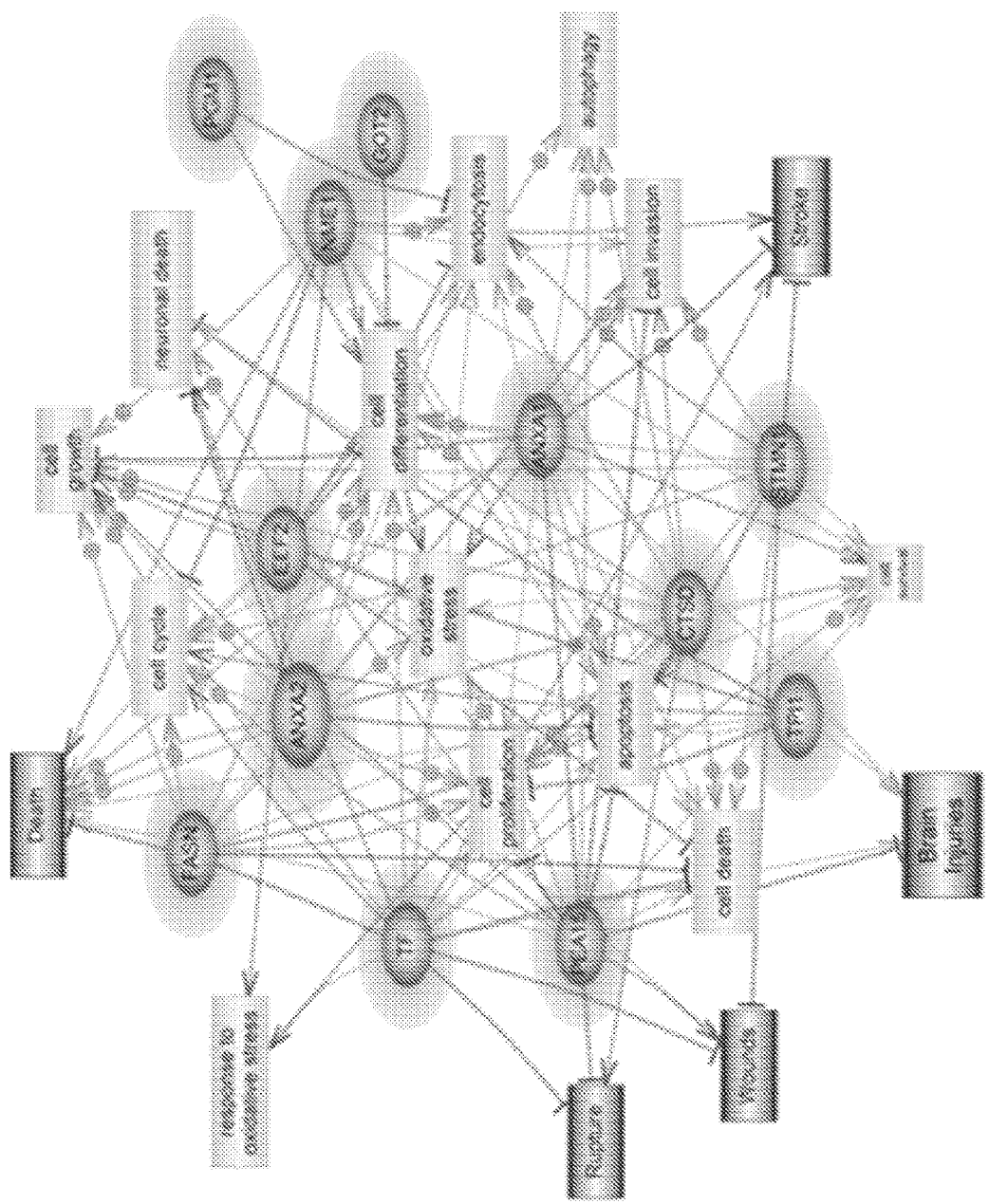

FIG. 20 is a systems biology mapping of interactome of candidate SCI biomarkers.

Figures 21A, 21B:
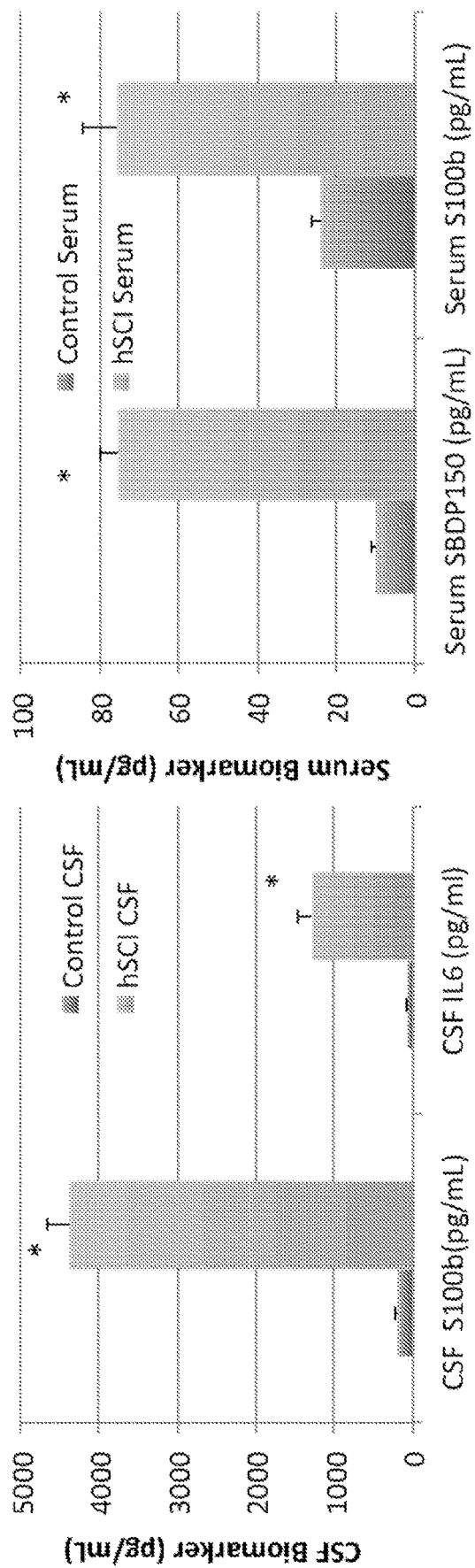

FIGS. 21A-218 show human spinal cord injury CSF samples show elevations of novel SCI biomarker S100b and IL-SCI patient (A) CSF and (B) serum samples are collected from first day (day to day 6 after injury. Shown here are all samples from patients, SCI n=12-15, control n=10-12. *p<0.05, SCI different from respective controls. (A) Control CSF (left bars), hSCI CSF (right bars); (B) Control serum (left bars), hSCI serum (right bars).

Figure 22:
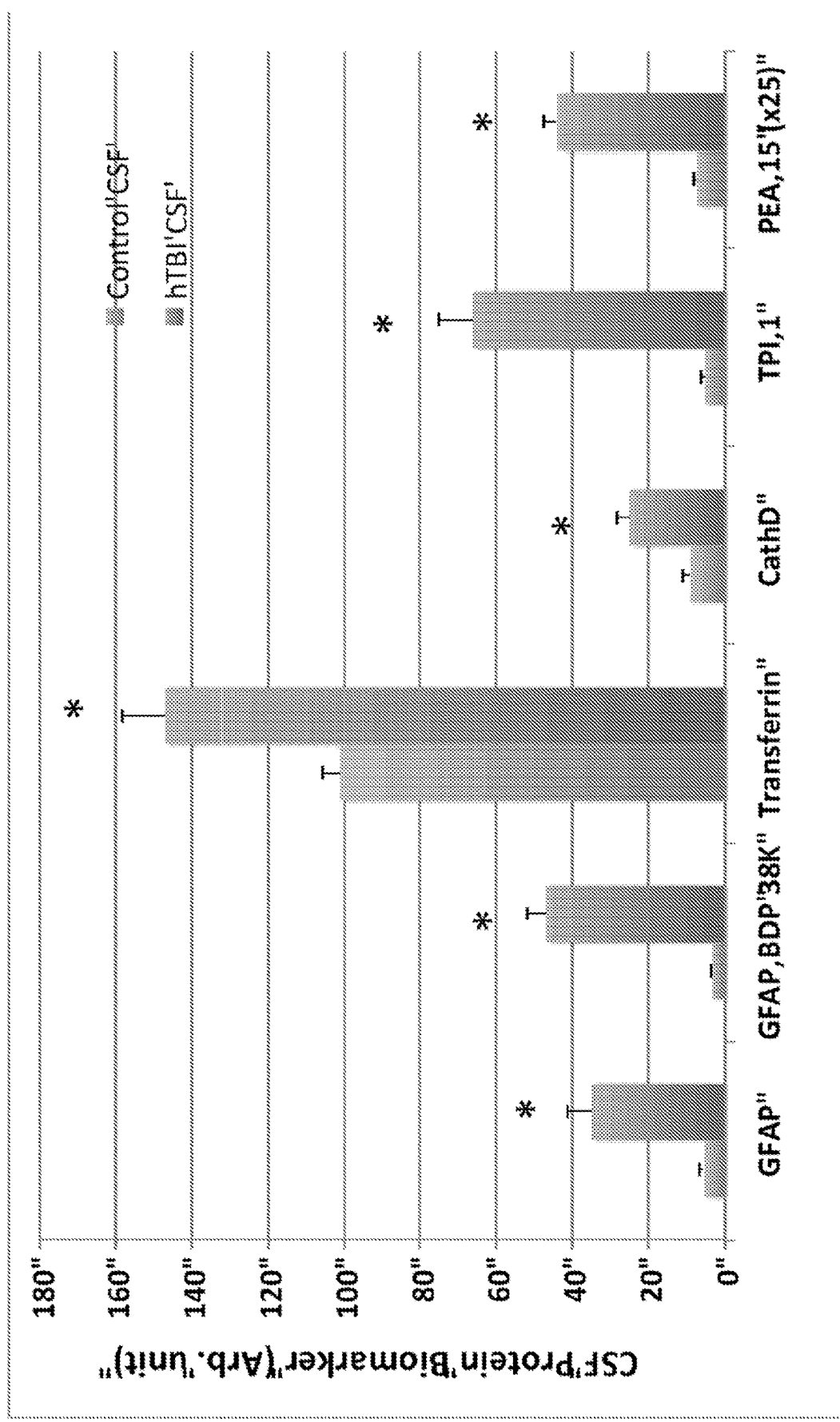

FIG. 22 shows example of detecting elevations of Transferrin, CathD, TPI and PEA-15 and CNS injury biomarkers GFAP and GFAP-BDP in acute human TBI CSF samples as compared to normal controls (N=10-14). Based on our new biomarker data on SCI, and since both SCI and TBI are similar and related neurotrauma, we infer that Transferrin. CathD, TPI-1 and PEA-15 will also be elevated in biofluids in TM patients (such as CSF). Here this TBI CSF biomarker elevation in fact supports our claim. Control CSF (left bars), hSCI CSF (right bars); *P<0.05 TBI vs. control.

Figure 23:
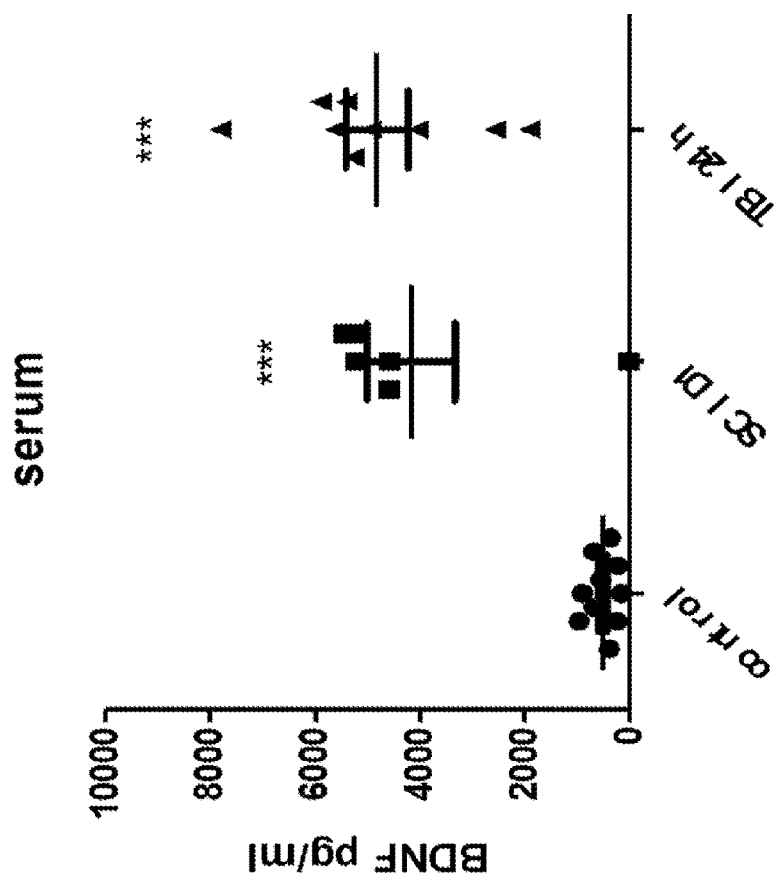

FIG. 23 shows human traumatic brain injury and spinal cord serum samples show elevations of novel biomarker BDNF when compared to control serum samples TBI and SCI patient samples used were collected within 24 h after injury. Shown are SCI and TBI n=10, control n=16. ***p<0.001 SCI or TBI different from control serum.

Figure 24:
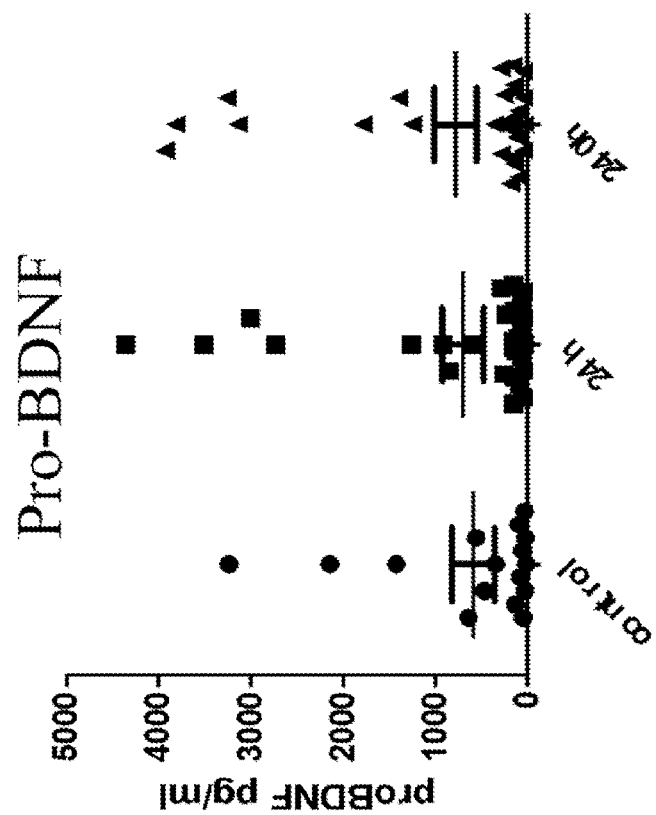

FIG. 24 shows human traumatic brain injury serum versus to control serum profile of biomarker pro-BDNF. TBI patient samples used were collected at 24 h at 240 h (10 days) after injury. TBI n=20, control n=16. Pro-BDNF levels were detectable as (pg/mL; mean±SEM) 583.1±230.4 for control, and elevated to 698.9±224.0 at 24 b after TBI and 780.2±232.0 at 240 h after TBI.

Figure 25B:
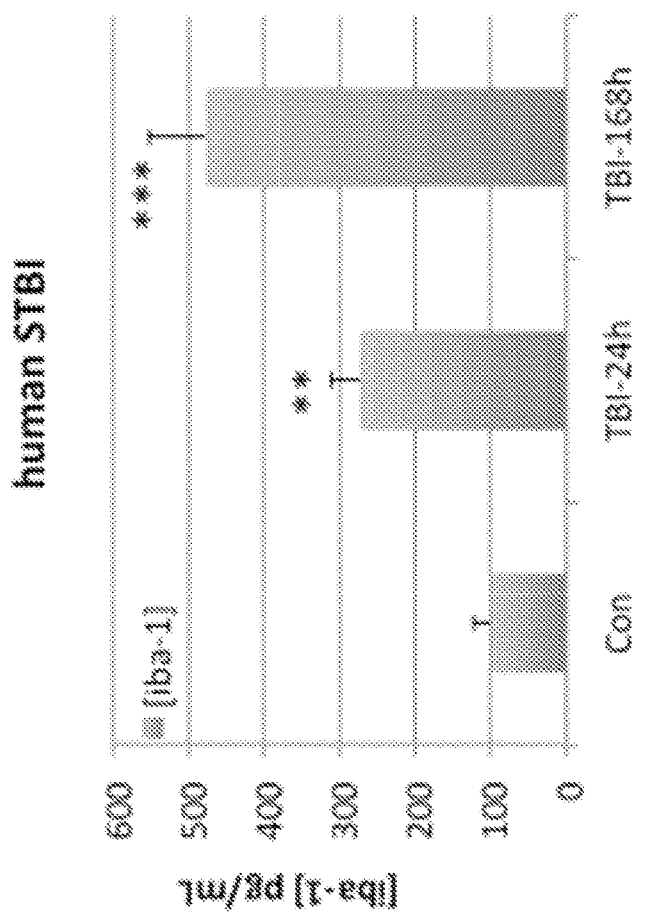
Figure 25A:
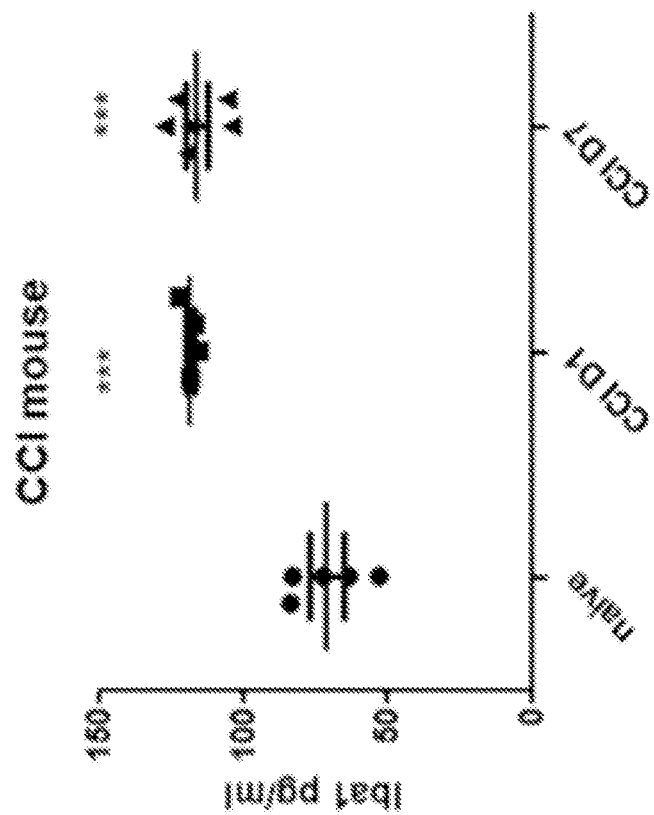

FIGS. 25A-25B show human and mouse traumatic brain injury serum versus to control serum profile for biomarker Iba-1. (A) Serum Samples from naïve mouse vs. mice with controlled cortical impact (TBI, CCI) at day 1 and 7 post-injury (n=6 each) were assayed for iba-1 levels. Iba-1 levels were detectable in mouse serum and found elevated in TBI serum at day 1 and day 7 post-injury (*p<0.001) as compared to naïve control serum levels. (B) Severe TBI patient samples used were collected at 24 h at 168 h (7 days) after injury. TBI n=12, control n=10. Iba-1 levels were detectable in human serum and found elevated in TBI at 24 h (p<0.005) and TBI 168 h (***p<0.001) as compared to control.

Figure 26B:
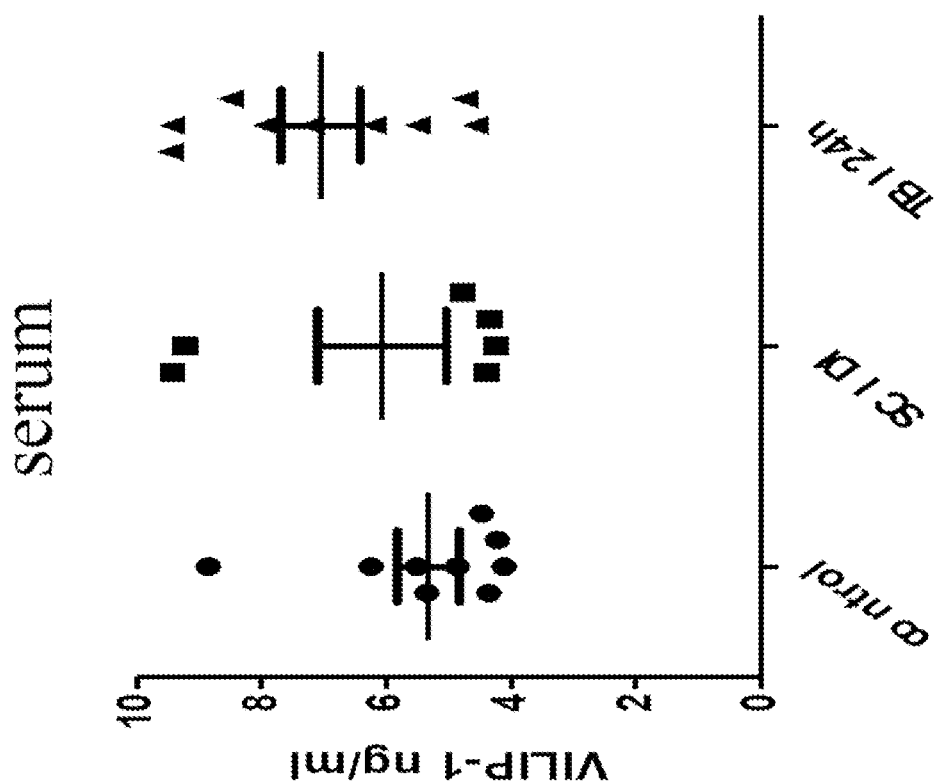
Figure 26A:
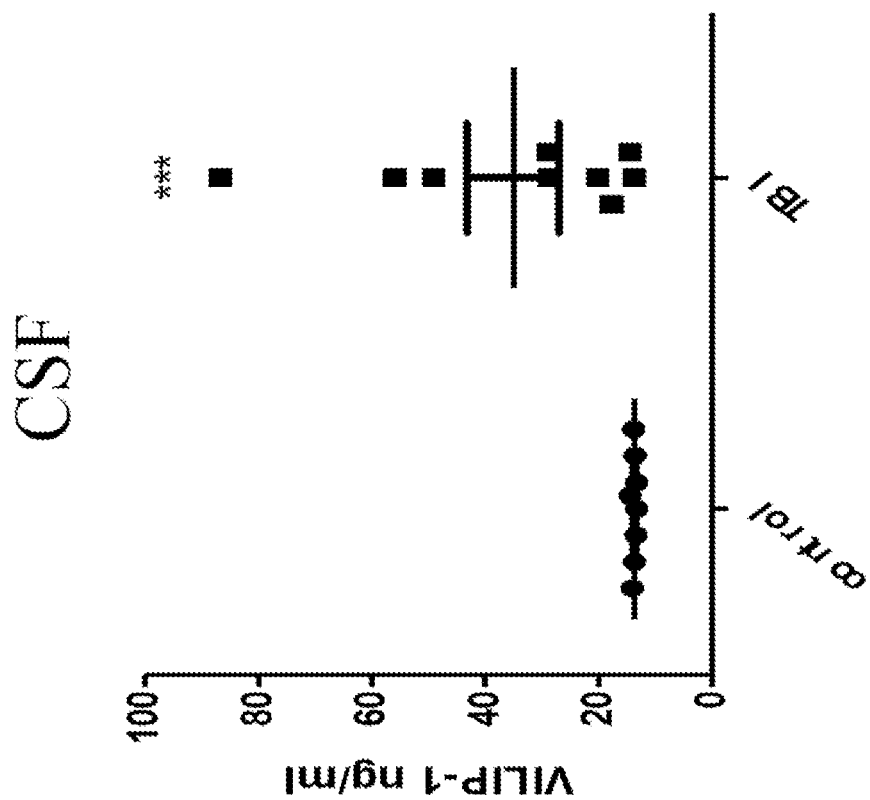

FIGS. 26A-26B show Visinin-like protein-1 (VILIP-1, VSNL1) elevations in human TBI CSF and human spinal cord injury and Tin serum as compared to respective controls. (A) CSF samples from control or TBI (day 1) were assayed for VILIP-1 levels. (***p<0.001) as compared to control CSF levels. (B) Severe SCI and TBI patient serum samples used were collected at 24 h after injury (n=6.8) VILIP-1 levels were detectable in human serum and found elevated in SCI at 24 h (6.07±1.03 pg/mL; mean+SEM) and TBI at 24 h (7.06±0.63) as compared to control serum group (5.33±0.50).

FIG. 27. Table 1 enumerating a list of new protein biomarkers for acute, subacute and/or chronic traumatic brain injury and spinal cord injury described in this document.

FIG. 28. Table 2. Identification of Differentially Expressed Proteins of sham and SCI rat lysate (24 h) using CAX-PAGE-/RPLC-MSMS platform.

Figure 29:
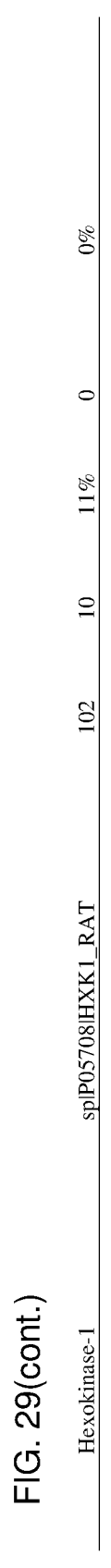

FIG. 29. Table 3. Identification of Differentially Expressed Proteins of sham and SCI rat lysate (7 days) CAX-PAGE-/RPLC-MSMS platform.

FIG. 30. Table 4. Various types of traumatic brain injury biomarkers by categories.

FIG. 31. Table 5. Various types of traumatic brain injury biomarker entities.

DETAILED DESCRIPTION OF THE INVENTION

Calcium binding protein S100 beta (S100β), glial fibrillary acidic protein (GFAP), myelin basic protein (MBP), neuron specific enolase (NSE), neurofilament protein (NFL), SBDP150/SBDP145/SBDP120, C-terminal hydrolase-L1 (UCH-L1), microtubule-associated 2 (MAP-2), and interleukins 6 and 8 (IL-6 and IL-8) have been identified as TBI biomarkers and some suggested similar SCI biomarkers as well. It was reasoned that TBI biomarkers might also be potential markers of spinal cold damage. These biomarkers can be validated for their potential use in clinical settings to determine the severity of SCI. However, due to the complexity of spinal cord injury, multiple interventions targeting different complications of damage may be required. So, it is unlikely that a single biomarker can be successfully used to diagnose and determine the severity of SCI patients.

Potential new SCI markers have been identified by using a CAX-PAGE-LC-MS/MS proteomic platform that can provide a better resolving and separation power and characterize proteome changes associated with SCI injury. The analysis has been done on SCI injured samples collected from both an SCI animal model (weight-drop) and human clinical studies of SCI patients. Comparing the molecular differences between the injured and non-injured regions produced a panel of SCI candidate biomarkers that can be used to correlate with disease progression. The identification of novel biomarkers implicated in SCI is important to delineate the severity of the injury and provide a new avenue for therapeutic intervention. In addition, since both SCI and TBI are similar pathophysiology and are inter-related neurotrauma, the identified new SCI biomarkers will also be elevated in biofluids in TBI patients (such as CSF, blood) and can serve as TBI biomarkers.

In addition, quantitative immunoblotting (Western blotting) and sandwich enzyme-linked immunosorbent assay (sw-ELISA) were also used for certain targeted TBI biomarker candidates based on a Systems biology and interactome analysis (FIGS. 24-25) and serial CNS tissue, biofluid (CSF and/or serum, plasma) samples from either animal model of TBI with different magnitude and injury type (mouse controlled cortical impact, single or repetitive overpressure blast wave brain injury in mice, single or repetitive close head concussive brain injury in mice), and rat spinal cord injury, as well as serial biofluid (CSF and/or serum, plasma) samples from severe TBI and spectrum TBI (covering severe-moderate to mild), with Glasgow coma scale (GCS) 3-15) and human spinal cord injury patients. Samples are collected at acute (day 1-3), subacute (day 7-10) to chronic (1 month to more than 1 year) phases after TBI or SCI.

Overall, the levels and types of biomarker proteins depended on the type and severity of the trauma, whether or not the trauma was repetitive and depending on the time line from the initial injury.

In particular, a large number of proteins were found to be significantly altered and useful as biomarkers for central nervous system injuries such as traumatic spinal cord injury (SCI), traumatic brain injury (TBI) and chronic traumatic encephalopathy, depending, among other factors, on stage of injury. Proteins with the more detectable changes include TDP-43 and its breakdown products BDPs (39 kDa, 35 kDa, 25 kDa).

Total-Tau (T-Tau) and phospho-Tau (P-Tau); for example at sites Thr181, Ser202, Ser202/Thr205, Thr231, Ser396/Thr401 and in particular P-Tau/T-Tau ratio are useful as acute and subacute/chronic biomarkers for central nervous system injuries and CTE formation detection. Tau and P-tau were assayed with available sw-ELISA methods. CNS injury-dependent T-Tau, P-Tau or P-Tau/T-Tau ratio elevations were confirmed from biofluid (CSF, serum, or plasma) from TBI patients or animals.

Triosephosphate isomerase (TPI-1), transferrin (TF), phosphoprotein enriched in astrocytes 15 (PEA-15), and cathepsin D (CathD) are also likely to be found as biomarkers for central nervous system injuries (TBI and SCI). Their CNS injury-dependent biofluid elevations can be confirmed by immunoblotting ELISA using biosample (CNS tissue, CSF, serum, or plasma) from TBI and SCI patients or animals.

IL-6 (Interleukin-6), Iba-1 (ionized calcium-binding adapter molecule-1), visinin-like proteins including VSNL1/VISL1 (Visinin-Like Protein 1, Hippocalcin-like protein 3, VSNL2/HPCAL4 (Hippocalcin-like protein 4) and VSNL3/VILIP-3/HACAL1 (Hippocalcin-like protein 1, Pro-BDNF (Proprotein form) and mature form of Brain-derived neurotrophic factor (BDNF) were identified based on CNS injury neuro-systems biology/interactome study and their CNS injury-dependent level elevations confirmed by immunoblotting and/or sw-ELISA using biofluid (CSF, serum, or plasma) from TBI and SCI patients or animals.

Combination biomarkers are particularly notable; for example, TPI-1, Transferrin, PEA-15 and Cathepsin D in combination with GFAP, GFAP breakdown products (GFAP-BDPs) and alphaII spectrin breakdown products and UCH-L1 and MBP (Myelin basic proteins (21K, 18.5, 17K, 14K). An additional combination of biomarkers is fatty acid synthase, NME/NM23 nucleoside diophosphate kinase 1, Stathmin 1, Eukaryotic translation elongation factor 2, Annexin A1, Annexin A2, Cathepsin D, Phosphoglucomutse 1, Glutamic oxaloacetic transaminase 2, mitochondrial (aspartate aminotransferase 2).

Other combination of CNS injury biomarkers are also noted; for example, Visinin-like proteins (e.g. VISL1, VSNL2, VSNL3), BDNF, Pro-BDNF, S100b, IL-6 and iba-1, in combination with TPI-1, Transferrin, PEA-15 and Cathepsin D or with GFAP, GFAP breakdown products (GFAP-BDPs) and alphaII spectrin breakdown products and UCH-L1 and MBP.

Proteomic analysis is a useful technique for simultaneously determining multiple proteins in a biological system; it provides robust methods to study protein abundance, expression patterns, interactions, and subcellular localization in the blood, organelle, cell, tissue, organ or organism that can be studied to provide accurate and comprehensive data about that system. Proteomics is the most powerful technique which can aid in the discovery of novel biomarker candidates; it utilizes extensive sample procedure and Data Dependent Acquisition to follow disease-specific proteins (identity and concentration). It facilitates the identification of all differentially expressed proteins at any given tune in a proteome and correlates these patterns with the healthy ones during disease progression. It has been used to study protein expression at the molecular level with a dynamic perspective that helps to understand the mechanisms of the disease. The complexity, immense size and variability of the neuroproteome, extensive protein-protein and protein-lipid interactions, all limit the ability of the mass spectrometer to detect all peptides/proteins contained within the sample; further, some peptides/proteins are extraordinarily resistant to isolation. Therefore, the analytical methods for the separation and identification of peptides/proteins must manage all of these issues by using separation techniques combined with the powerful new mass spectrometry technologies to expand the scope of protein identification, quantitation and characterization.

The complexity of a biological sample can be reduced by further separation or fractionation at the protein or peptide level. Multidimensional LC can be used for two or more different types of sequential combinations to improve significantly the resolution power and results in a larger number of proteins to be identified. Ion-exchange chromatography (IEC) in the first dimension is very suitable for the separation of proteins and peptides, separating proteins based on their differences in overall charges. IEC's stationary phase is either an anion or a cation exchanger, prepared by immobilization of positively or negatively charged functional groups on the surface of chromatographic media, respectively. Proteins or peptide separation occurs by linear change of the mobile-phase composition (salt concentration or pH) that decreases the interactions of proteins with the stationary phase, resulting in finally eluting the proteins. Also, SDS-PAGE can be used for further protein separation by apparent molecular weight with the resolving distance optimized for the proteome of interest. Furthermore, peptides can be separated by their hydrophobicity using a reversed phase C18 column, which can be directly coupled to the electrospray mass spectrometer (ESI-LC-MS/MS). Reversed-phase liquid chromatography (RPLC) is most often used in the second dimension due to its compatibility with the downstream mass spectrometry (sample concentration, desalting properties, and volatile solvents).

Proteomics has two approaches: "bottom-up", which involves direct digestion of a biological sample using a proteolytic enzyme (such as trypsin) that cleaves at well-defined sites to create a complex peptide mixture, followed by analysis of the digested samples on platforms that include liquid chromatography prior to tandem mass spectrometry (LC-MS/MS); and "top-down", that involves separating intact proteins from complex biological samples using techniques such as liquid chromatography or 2-D gel electrophoresis, followed by differential expression analysis using spectrum analysis or gel imaging platforms. Although top-down analysis preserves protein-protein interactions and does not lose the protein information, it has been limited because of the difficulty in intact protein processing due to the lack of separation methods (only gel based) as well as the challenges of performing mass spectrometry on intact high-molecular weight proteins.

Mass spectrometry (MS) is the most important tool for protein identification and characterization in proteomics due to the high selectivity and sensitivity of the analysis. Electrospray ionization (ESI) is considered as an ideal ionization source for protein analysis due to two characteristics: first, the ability to produce multiply charged ions from large molecules (producing ions of lower m/z that are readily separated by mass analyzers such as quadrupoles and ion traps), and second, the ease of interfacing with chromatographic liquid phase separation techniques. Electrospray ionization followed by tandem mass spectrometry (ESI-MS/MS) is one of the most commonly used approaches for protein identification and sequence analysis.

Proteomic analysis has been conducted previously by others to identify biomarkers and assess severity of SCI utilizing traumatic animals, but these methods have not been used to identity biomarkers in CSF patients with traumatic SCI because CSF sampling is challenging; for example, here differential neuroproteomics analysis of spinal cord injury has been performed to show that not only can injury be demonstrated but severity can also be assessed.

Systems Biology (SB)-Assisted Biomarker Integration

Rapid growth of high throughput technology in genomic and proteomic studies facilitates generation of tremendous amounts of data. A comprehensive database from the relevant scientific literature using data integration and warehousing techniques can be developed. Database of brain injury-related information, including high throughput "omic" datasets (genomics, proteomics, metabolomics, lipidomics etc.), "targeted" pathway, and molecular imaging studies can be generated. Systems modeling and simulation are essential for effective therapeutics development future. Different model representations have been established to serve these purposes. The graphical diagrams of biological processes such as Pathway Studio, Gene Spring, Ingenuity Pathway and Gene GO give visual presentations of network models by incorporating genome, proteome and metabolome data. However, different formats which incorporate quantitative data generated from or validated with directed biological studies have emerged and have found further use in system simulation and analysis. These bioinformatics software (as Pathway Studio, Gene Spring, Ingenuity Pathway and Gene GO) have been used to construct functional interaction maps of the generated high-throughput data. Functional interaction maps depict altered subsets of genes and/or proteins describing perturbed cellular functions relevant to a specific disorder in question. A major strength of interaction maps lies in their ability to predict and identify certain gene(s) and or protein(s) that have been missed by experimental analysis as well as to provide potential functions of identified proteins with an unknown physiology.

Since central nervous system (CNS) injury is a very complex condition with multiple comorbidities, a wide range of systems biomarker candidates can be employed to match different conditions. Systems biology tools are unbiased approaches to identify nest-redundant neuromodulation/neurotoxicity pathways and to further pinpoint candidate diagnostic biomarkers and/or molecular targets for therapy. These tools help to organize available data and knowledge according to the high-level, holistic view required by system biology. Analysis methods (e.g. Support Vector Machines, Bayesian Networks, Cognitive Maps, and Dynamic Feature Selection) have been used for integration: System biology also supports the iterative, hypothesis-free approach to scientific discovery that is increasingly being adopted in biological research. The resulting high-level views (pathways, maps, biomarkers), together with the data sources are available through a comprehensive in-house service. Following that, predictive systems responses can also be generated by applying optimization-based predictive Model that factor in multi-group multi-stage analysis.

Both SCI and TBI are devastating diseases with many consequences and no known effective treatment. Although it is quite easy to diagnose acute traumatic. SCI or TBI, the assessment of injury severity and projection of disease progression or recovery is often challenging. Proteomics is a promising approach for biomarker discovery; it has been used to study protein expression at the molecular level with a dynamic perspective. Systems biology is another approach to identify additional unobvious biomarkers for CNS injury such as SCI and TBI.

To validate the presence or level elevations of a candidate TBI or SCI biomarker protein in disease biofluid, cerebrospinal fluid (CSF) can be analyzed because it is proximal to injury site and blood sample (such as serum, plasma) due to their accessibility), from human TBI or SCI patients or animal model of TBI and SCI. It can be compared with normal control biofluid samples). The candidate biomarker is then quantified in such biofluid using immunological methods such as immunoblotting and sandwich enzyme-linked immunosorbent assay (sw-ELISA) methods and the data analyzed.

EXAMPLES

The following examples are provided as illustrations of the invention and are in no way to be considered limiting.

Example 1

Mouse controlled cortical impact (CCI) for severe TEL A CCI device was used to model TBI. CB57BL/6 mice (male, 3-4 months old, Charles River Laboratories) were anesthetized with 4% isoflurane in oxygen, as a carrier gas for 4 minutes, followed by maintenance anesthesia of 2-3% isoflurane. After reaching deep plane of anesthesia, mice were mounted in a stereotactic frame in a prone position; and secured by ear and incisor bars. Core body temperature will be monitored continuously by a rectal Thermistor probe and maintained at 37±1° C. by placing an adjustable temperature controlled heating pad beneath the rats. An integrated Impactor One Stereotaxic impactor device for CCI (Leica inc.) is used. The impactor is electromagnetically controlled. Animals are mounted in a stereotactic frame in a prone position and secured by ear and incisor bars. A midline cranial incision was made and a unilateral (ipsilateral) craniotomy (3 mm diameter) was performed adjacent to the central suture, midway between the bregma and the lambda. The dura mater was kept intact over the cortex: Brain trauma was induced using a mounted impactor tip (with 2 mm diameter) by impacting the right cortex (ipsilateral cortex) at a velocity of 3.5 m/s, 1.5 mm compression depth (for severe injury) and a 200 ms dwell time (compression duration). Sham injured control animals (if performed) underwent identical surgical procedures, but did not receive an impact injury.

Mouse Single and Repetitive Mild Closed Head Injury to Model Concussive TBI:

Mouse single of repetitive closed head injury is fashioned after a previous study (Shitaka et al. J Neuropathol Exp Neurol 2011 July; 70(7):551-67). The mice were selected at random to be exposed to single mCHI or rmCHI (four impacts with a 72 hr interval between impacts) and no injury. On day 1, mice were anesthetized with 4% isoflurane in oxygen as a carrier gas far 4 min followed by maintenance anesthesia of 2% to 3% isoflurane. After reaching a deep level of anesthesia, the mice were shaved and mounted in a stereotactic frame in a prone position Brain trauma was produced using a Impactor One Stereotaxic impactor device (Leica Inc.) by impacting the sagittal suture midway with a commercial rubber impactor tip (1 cm in thickness, 9 mm in diameter) at a velocity of 4.0 m/s, 3.8 mm compression depth and a 200 ms dwell time (compression duration). The center of impact corresponds to the central sagittal suture midway between, coronal and lambdoid sutures. The deformation of the rubber tip spread the impact force over the skull. For the rmCHI mice. Additional injuries, were administered at days 4, 7 and 10 after the original injury. Sham control animals underwent identical procedures, but did not receive an impact injury.

Figure 1:
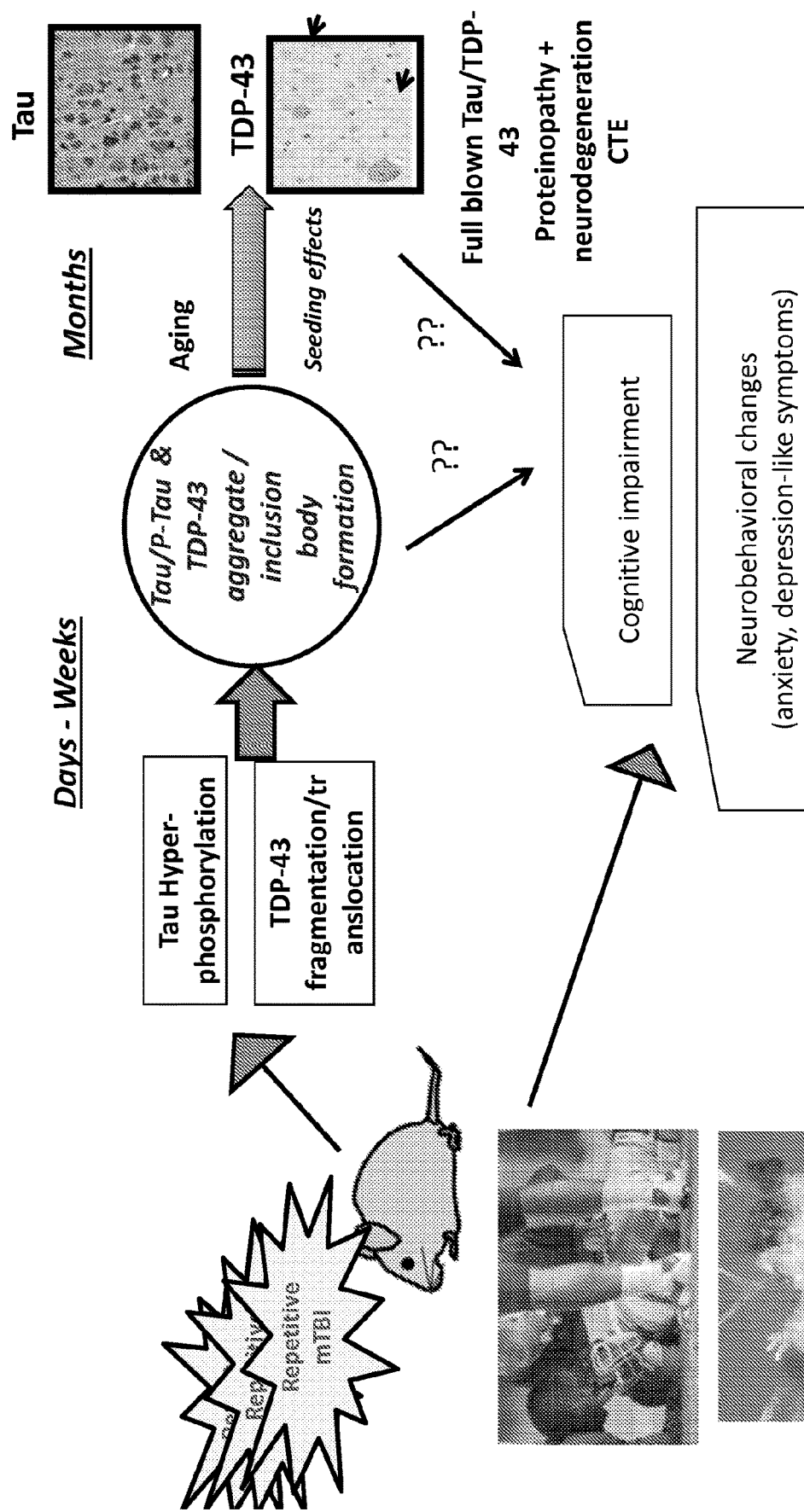
FIG. 1 shows Tau protein plus TAR DNA-binding protein 43 (TDP-43) proteinopathy after repetitive closed head traumatic brain injury, resulting in the pathogenesis of post-TGI CTE.

Mouse Overpressure Blast-Wave Induced Brain Injury Model:

Overpressure blast-wave induced brain injury (OBI) experienced by exposure to improvised explosive device (IED), roadside bombing or during breacher exercises or operations is becoming and emerging challenge in the field of TBI in both research and clinical management and rehabilitation standpoints because very little is known about its pathological manifestation and consequences. The shocktube has 4' inner diameter, and is 7 ft long with realistic overpressure and underpressure blast waves. Briefly, mice are anesthetized with 3-5% isoflurane in a carrier gas of $O_2$ for approximately 3-5 minutes. Animals exposed to blast will receive a single discharge from the apparatus, whilst those exposed to sham blast will be exposed to the sound of a single blast outside of the shocktube, but not directly to the blast wave. The design features a 4 inch inner diameter shock tube (total 7 ft in length) that contains the high pressure driver section with its end collected to nitrogen gas tank and the opposing side a partition for Mylar membrane (diaphragm) insertion followed by a modular driven section (lower pressure) with an open end (see FIG. 1). Mylar membrane with thickness (0.05-0.07 in) was used that provide mean peak overpressure between 100 to 300 kPa (from mild to high overpressure impact) peak pressure, lasting less than 1.0 ms with rapid exponential decay. Mouse and its head are secured with Velcro straps onto wire-mesh platform insert 1 ft into the open end of the driven section. The orientation used is such that the mouse in a prone position rest on the horizontal wire-mesh platform with its nose points toward the incoming shockwave.

Example 2

Figure 3:
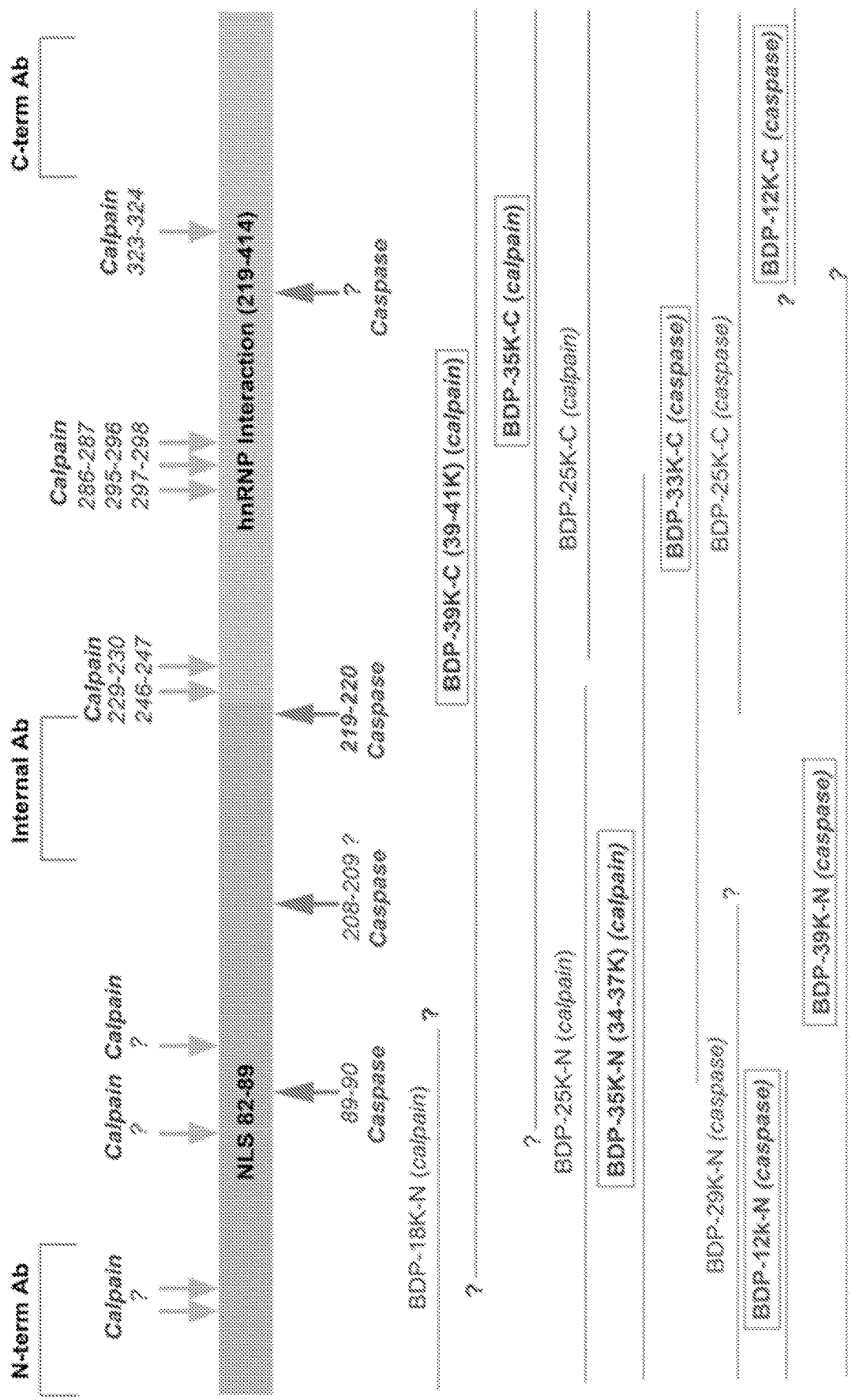
FIG. 3 shows a schematic of transactivation response DNA-binding protein 43 (TDP 43) proteolysis by calpain and caspase-3 pathways. In this model, caspase cleaves at the N-terminal (Asp89*Ala90, Asp219*Val220, based on Zhang Y J, et al Journal of Neuroscience 2007; 27: 10530-10534) producing caspase-dependent CTFs at 33 and 25 kDa and unknown C-terminal cleavage sites generate fragments of 39 and 12 kDa. However, calpain cleaves at least six sites (Phe229*Ala230; Leu243*Cys244; Gln286*Gly287; Gly295*Gly296; Ala297*Gly298; Met323*Ala324, based on Yamashita T, et al Nature Communications 2012; 3: 1307) producing multiple fragments. But the cleavage sites generating major, calpain specific C-terminal fragments (CTFs) of 39 and 35 kDa remain unknown.

FIG. 4 shows the detection of TAR. DNA-binding protein 43 (TDP-43, transactive response DNA binding protein 43 kDa and its breakdown products. (BDPs 39 kDa and 35, 25 kDa) (FIG. 3) in brain (cortex) tissue lysate in mice following TBI (controlled cortical impact) and blast overpressure brain injury). The detection method shown is quantitative immunoblotting (western blots). Other methods such as sandwich ELISA method or amplified sandwich ELISA can also be used. The data indicate that TDP-43 BDPs are released from injured brain cells and tissue into biofluids such as cerebrospinal fluid (CSF) (FIG. 5) and/or blood, including, serum and plasma).

Example 3

Figure 5A:
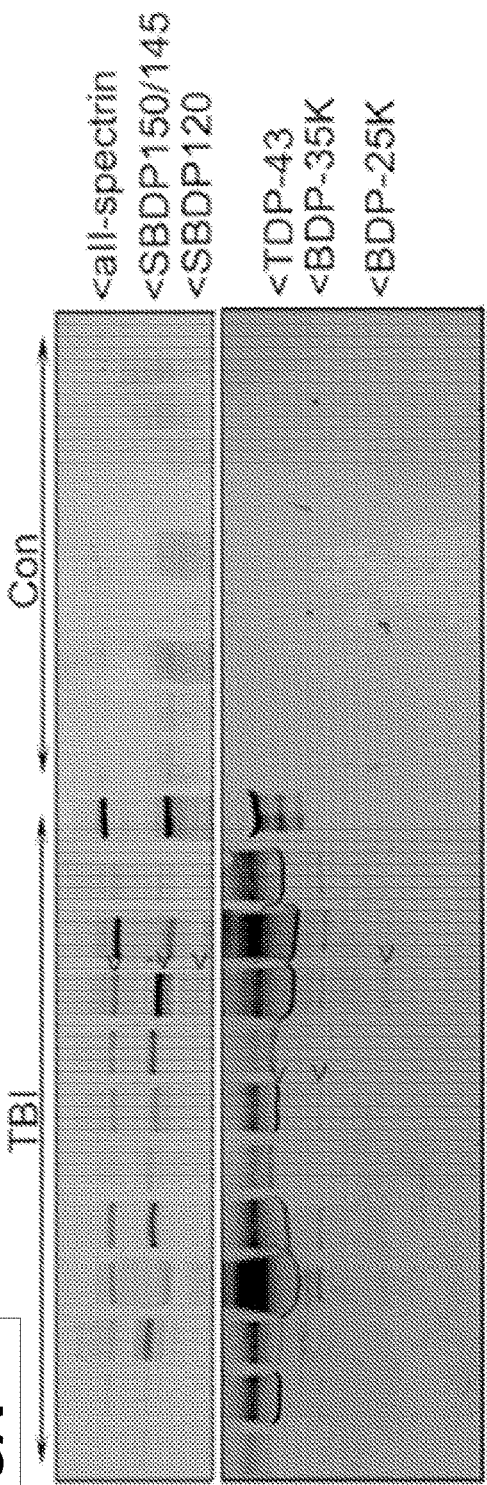
FIGS. 5A-5B. Transactivation response DNA-binding protein 43 (TDP-43) and breakdown products (BDPs) released into human cerebrospinal fluid (CSF) after severe traumatic brain injury (TBI). (A) For the determination of TDP-43 levels, 10 mL of fivefold concentrated CSF samples from either controls or TBI patients in the first 24 hours post TBI were used. Released TDP-43 was detected with C-terminal TDP-43 antibody. alphaII-Spectrin was also probed as a control biofluid marker Each lane represents an individual subject. For western, the high level of albumin (66K) (indicted with '}'), pushes down and distort the band of intact TDP-43. (B) Scatterplots for SBDP150/145K, TDP-43, and BDP-35K C-terminal fragments levels in human CSF.
Figure 5B:
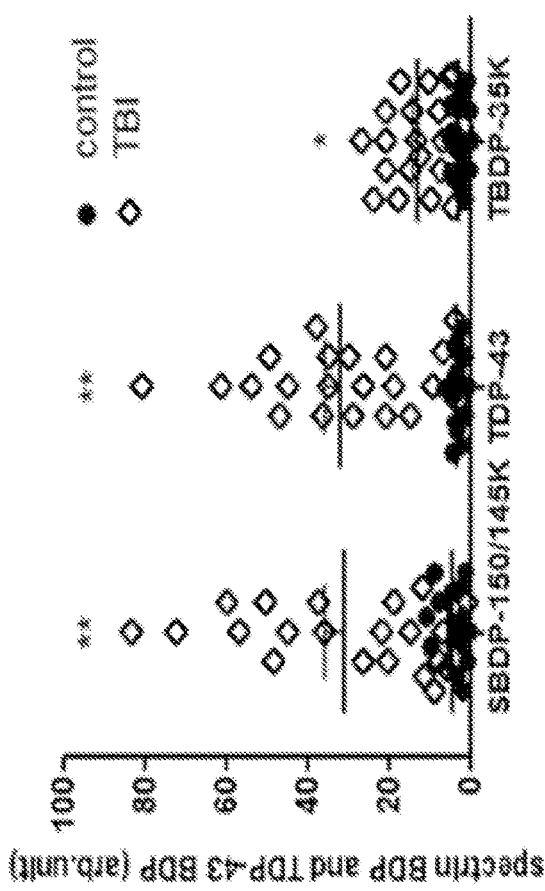

FIG. 5 shows the detection of intact TDP-43 and BDPs (35K; 25K) released into human CSF after severe TBI (n=21) over normal controls (n=12). This TDP-43 and BDP release pattern is comparable to alphaII-spectrin BDP (SBDP150, 145) release into CSF after TBI in humans. The detection method used is quantitative immunoblotting (western blots). Other methods such as sandwich ELISA method or amplified sandwich ELISA can also be used, as demonstrated by SBDP. TDP-43 and its BDPs are likely released from injured brain cells and tissue into biofluids such as cerebrospinal fluid (CSF) and blood, including serum and plasma, causing the biofluid levels of TDP-43 and its BDPs to rise after CNS-injury. This example also demonstrates that TDP-43 and BDP quantification tests can distinguish TBI from control subjects using biofluids with the first 24 h, and possibly longer.

Example 4

Figure 2:
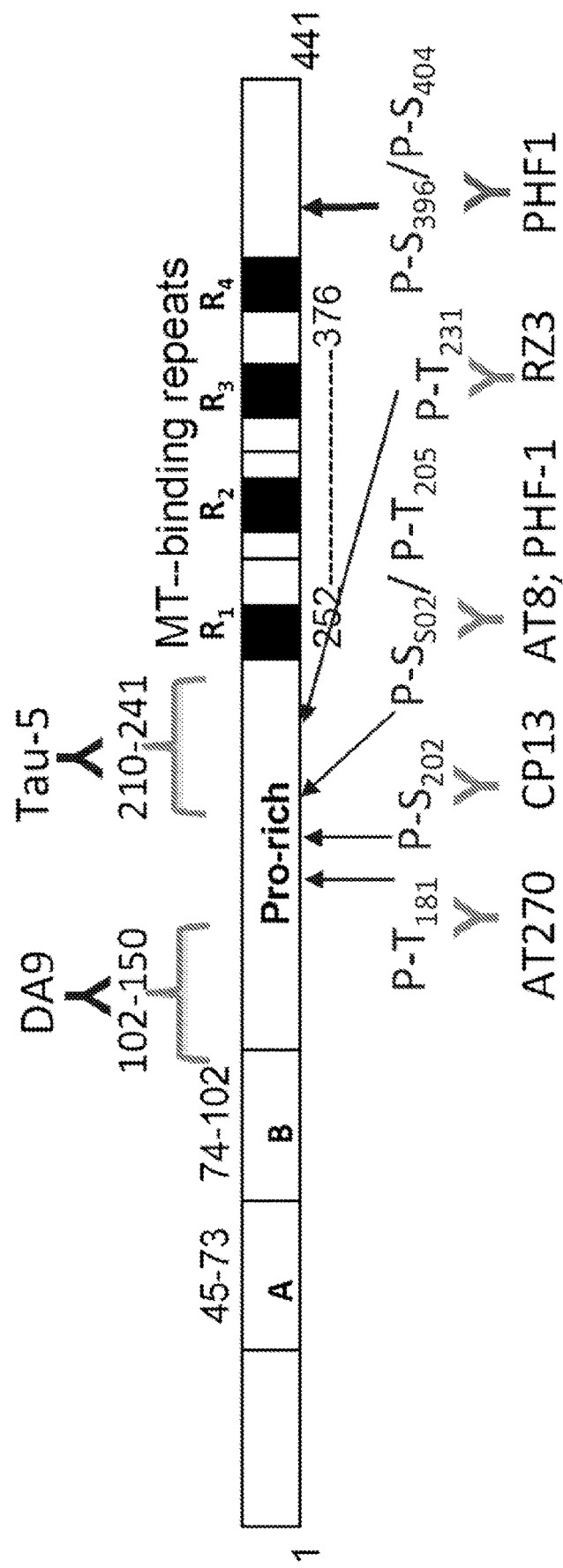
FIG. 2 illustrates Tau (MAPT) protein as a microtubule associated protein and its structure schematics. Shown is human 4R form (441 amino acids; aa) showing major pathological phosphorylation sites (including T-181, S-2-2, S205, T-231 and S396/S404) before the P-residues are specific monoclonal antibodies (MAb) recognizing these phospho-specific peptides. Also for example, sequences that are recognized by known MAb are a.a. 102-150 (recognized by DA9) or aa 210-241 (by Tau-5).
Figures 6A, 6B:
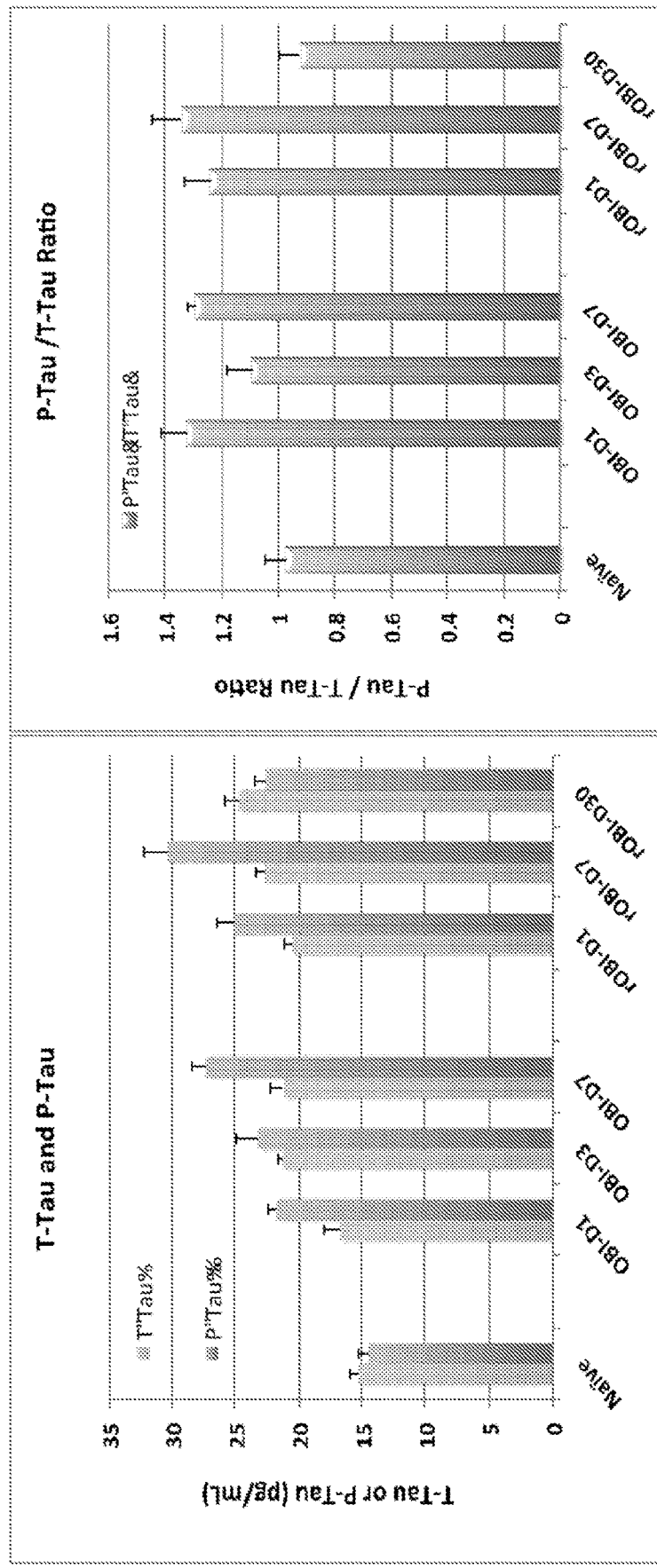
FIGS. 6A-6B. Serum Tau and P-Tau and P-Tau/T-tau elevations at various time points after single (OBI) or repetitive (rOBI) overpressure blast wave induced brain injury in mice ANOVA p<0.001 for OBI and rOBI group over naive for (A) T-Tau, P-Tau and (B) P-Tau-Tau ratio.
Figures 7A, 7B:
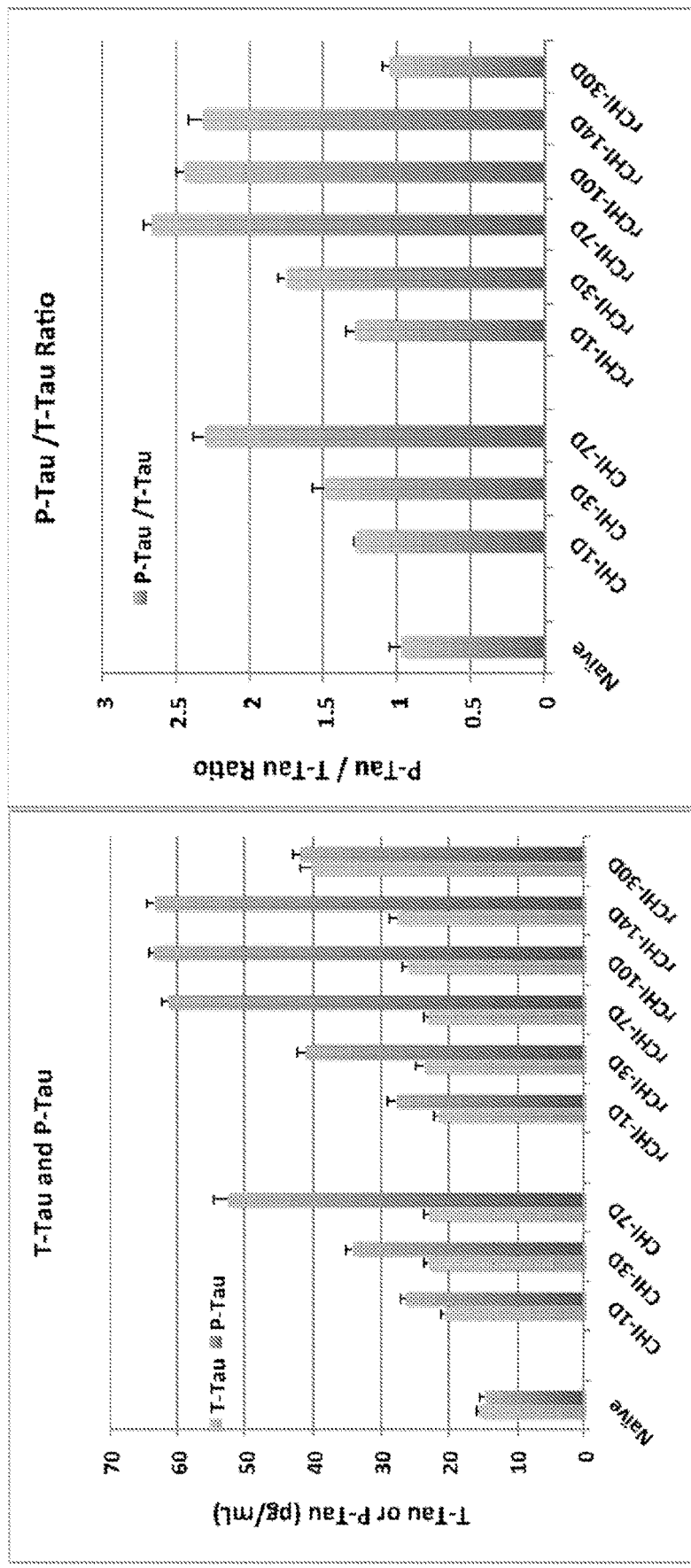
FIGS. 7A-7B. Serum Tau and P-Tau and P-Tau/T-tau elevations at various time points after single (CHI) or repetitive (rCHI) closed bead concussive brain injury in mice. ANOVA p<0.001 for OBI and rOBI group over naïve for (A) T-Tau, P-Tau and (B) P-Tau/T-Tau ratio.

FIGS. 6 and 7 show the detection of serum total microtubule-associated protein Tau (T-Tau) and phosphorylated form of Tau; i.e., P-Tau (at Serine-202) and P-Tau/T-Tau ratio (FIG. 2) elevations after both single and repetitive closed head injury (CHI; rCHI) and single and repetitive blast overpressure brain injury (OBI, rOBI) in mice at different time points post injury (day 1, 3, 7, 10, 14, and/or 30). The detection method used is quantitative amplified sandwich ELISA. Other sensitive immunoassay formats can be used.

Example 5

FIG. 8 shows the detection of total Tau and P-Tau marten in human acute severe TBI CSF samples. In this human severe TBI study, total Tau is elevated in acute TBI CSF groups in comparison to control CSF, P-Tau and P-Tau/T-Tau ratio elevations are even more robust in the TBI SCI group. This example demonstrates that Tau, P-Tau tests can distinguish TBI from control subjects using biofluids with the first five days. CSF Tau and P-Tau assays were run as described above.

Example 6

Figure 9C:
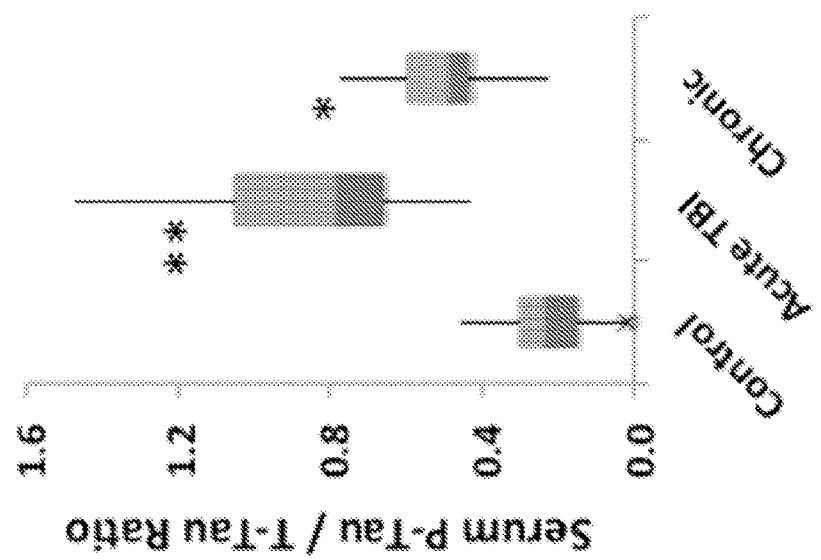
FIGS. 9A-9C show Serum T-Tau, P-Tau and P-Tau/T-Tau detection of acute and chronic TBI. Healthy Control vs. acute severe TBI (first 24-72 h) and chronic (ave. 30 day) serum samples, (A) Total tau, (B) P-tau and (C) P-Tau/Total-Tau ratio are plotted. N=10-16 *p<0.05 different from control, **, p<0.01 different from control.
Figure 9B:
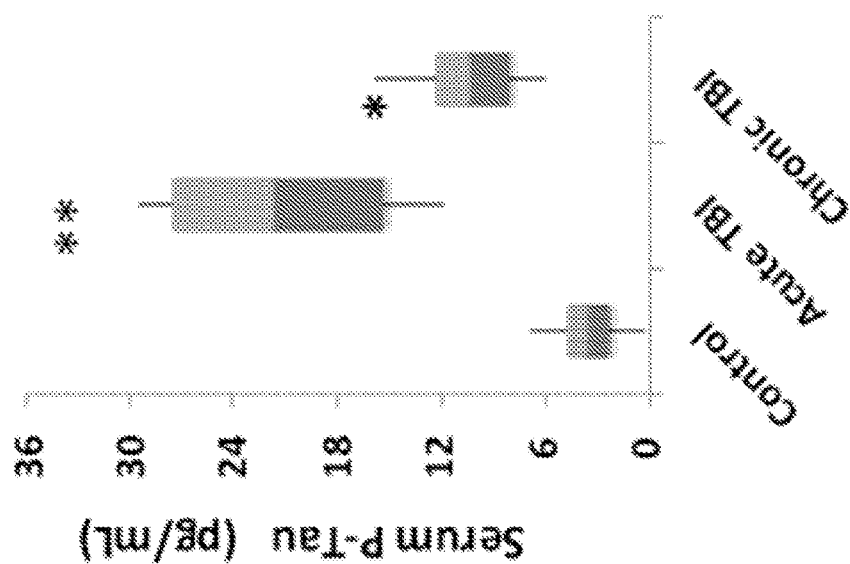
Figure 9A:
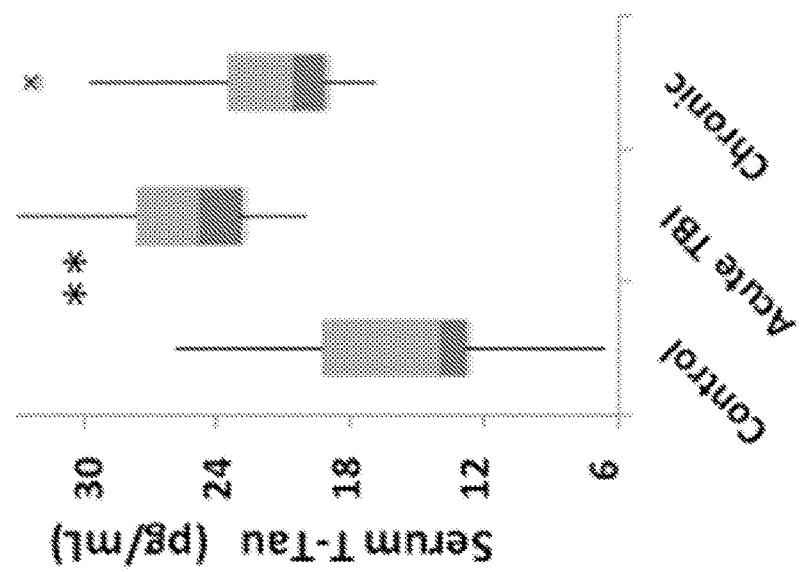

FIG. 9 shows the detection of total Tau, P-Tau, and P-Tau/T-Tau ratio in Day 1-3 and Day 30 (range 19-50 days) severe TBI serum samples that are higher than the levels in the normal control serum. It further shows that in addition to differential P-Tau, Tau levels, the use of P-Tau/T-Tau ratio is a useful diagnostic method to differentiate acute (Day 1-3) and chronic (average Day 30) phases of severe human TBI serum samples versus normal controls. Serum/plasma Tau and P-Tau assays were run as described above.

Example 7

Figure 10B:
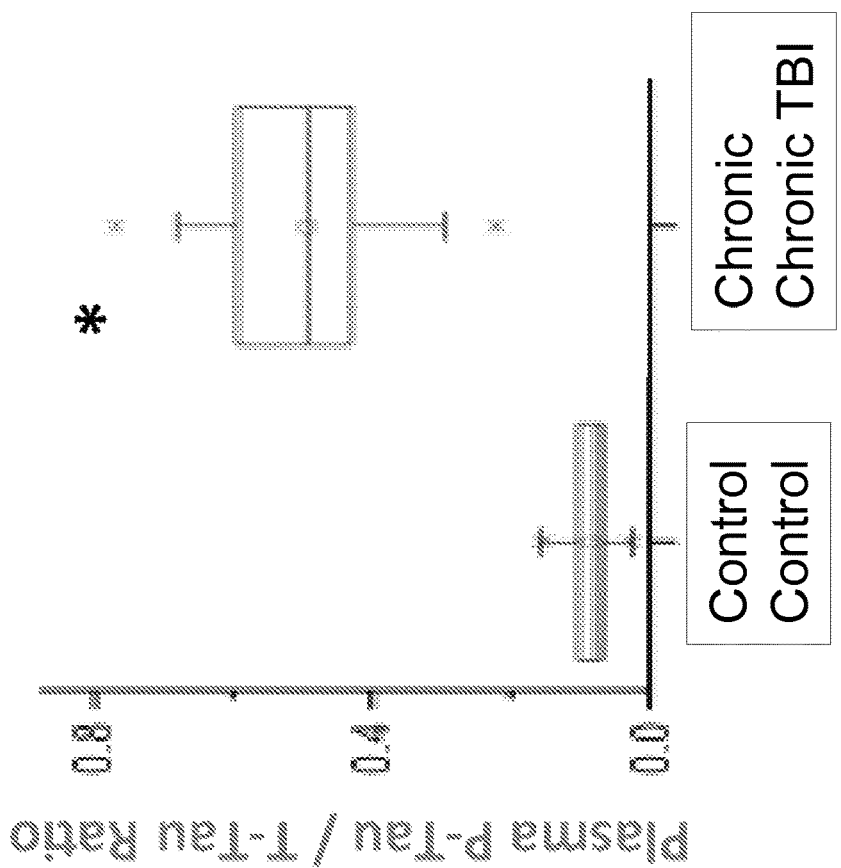
FIG. 10A shows plasma P-Tau and FIG. 10B shows P-Tau/T-Tau Ratio in Chronic human TBI. Plasma samples (average 6.3 mo.; range 1-12 mo.) vs. normal controls. n=21-29. *p<0.05 chronic TBI different from control.
Figure 10A:
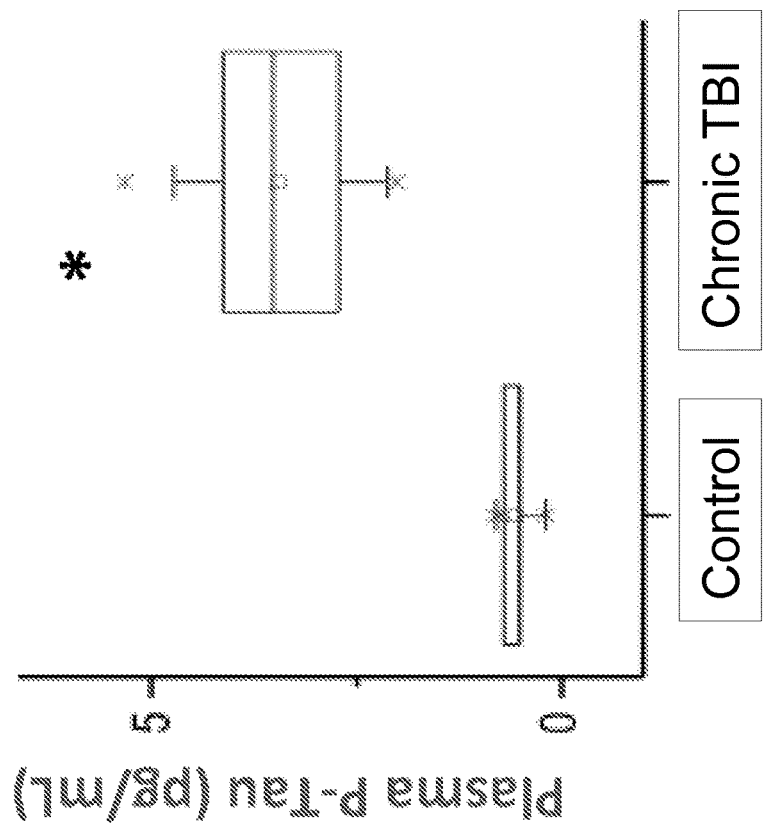

FIG. 10 further shows the detected elevations of P-Tau and P-Tau/T-Tau ratio in plasma samples from chronic TBI patients (in rehabilitation) (average 6.3 months post-TBI; range 1-12 months) vs. normal controls. n=21-29. It shows that in addition to differential P-Tau, Tau levels, the use of P-Tau/T-Tau ratio is a useful diagnostic method to differentiate acute (Day 1-3) and chronic (Day 30) phases of severe human TBI serum samples versus normal controls.

Example 8

Figures 11A, 11B:
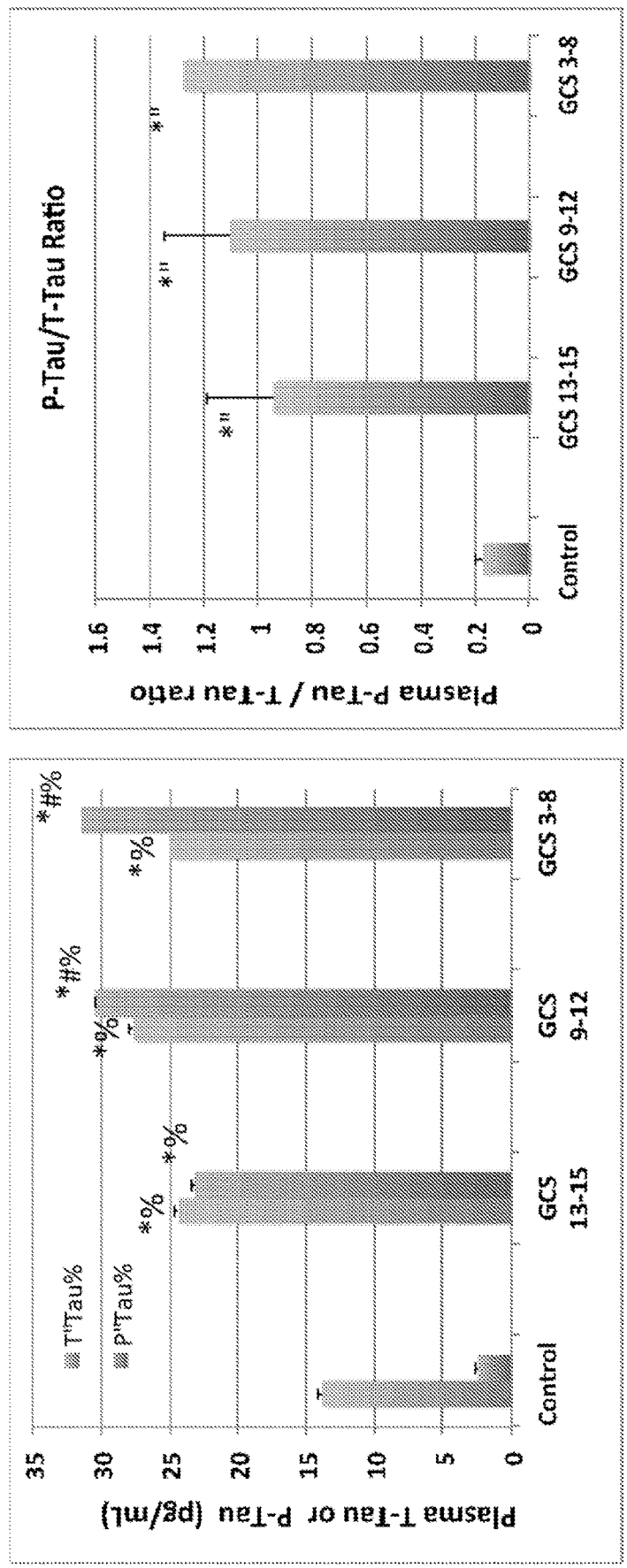
FIGS. 11A-11B show that for spectrum TBI, T-Tau, P-Tau and P-Tau/T-Tau ratio detecting control vs. different TIN severity grouped as GCS 13-15 (mild), GCS 9-12 (moderate) and GCS 3-8 (severe). A) T-Tau (left bars), P-Tau, (right bars). (B) P-Tau/T-Tau ratio. *p<0.05 different from control, #, p<0.05 different from CSG 13-15 group.

FIG. 11 shows the Tau, P-tau and P-Tau/T-Tau ratio using plasma samples from a human-TBI study covers the full spectrum of TBI (severe, moderate, mild). Plasma from n=65 TBI subjects was used from the acute phase of TBI (within 24 h). The T-Tau, P-Tau and P-Tau/T-Tau ratio can differentiate control vs. different TBI severity grouped— GCS 13-15 (mild), GCS 9-12 (moderate) and GCS 3-8 (severe).

Figures 12A, 12B:
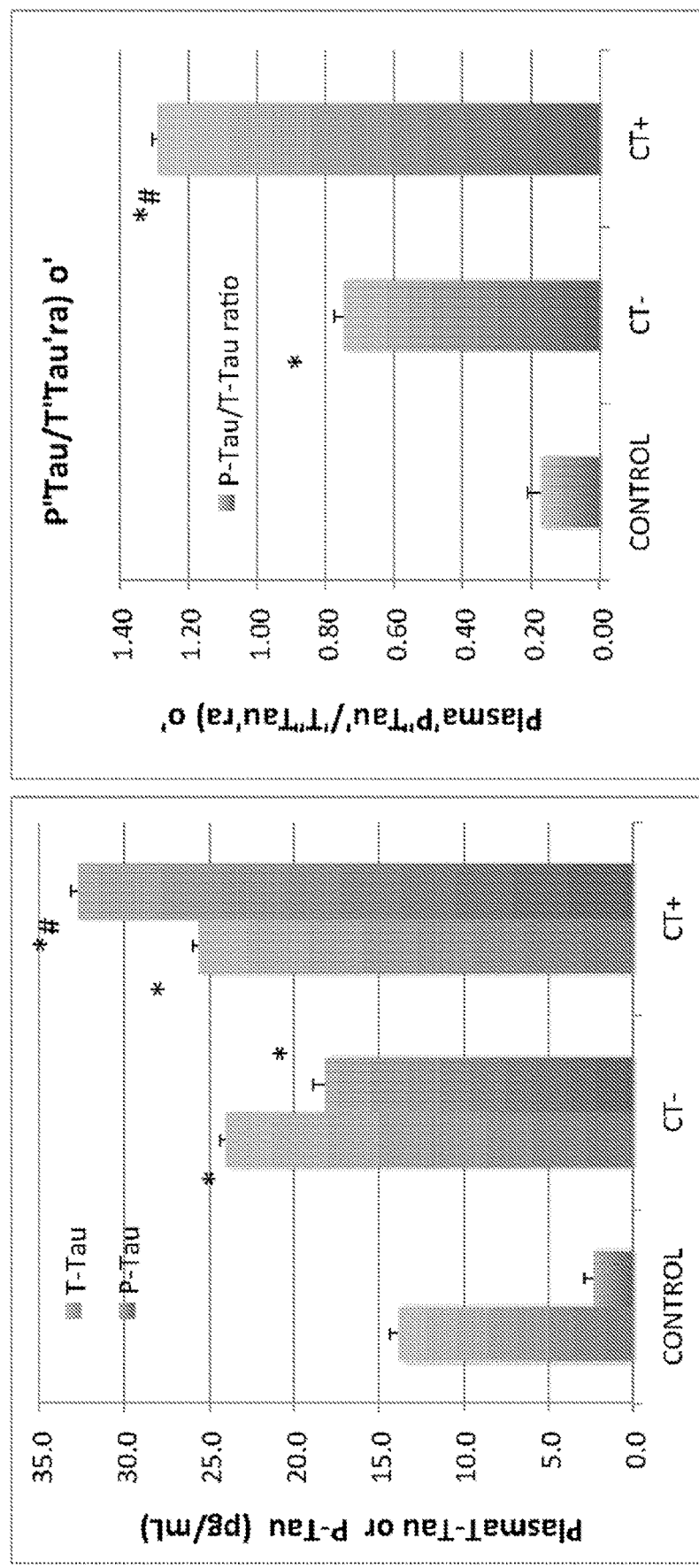
FIGS. 12A-12B show that for spectrum TBI, T-Tau, P-Tau and P-Tau/T-Tau ratio detecting control vs. CT normal and CT abnormal TBI patience. (A, left panel) T-tau (leftbars), P-Tau, (right bars). (B, right panel) P-Tau/T-Tau ratio. *p<0.05 different from control, #, p<0.05 different from CSG 13-15 group.
Figure 13A:
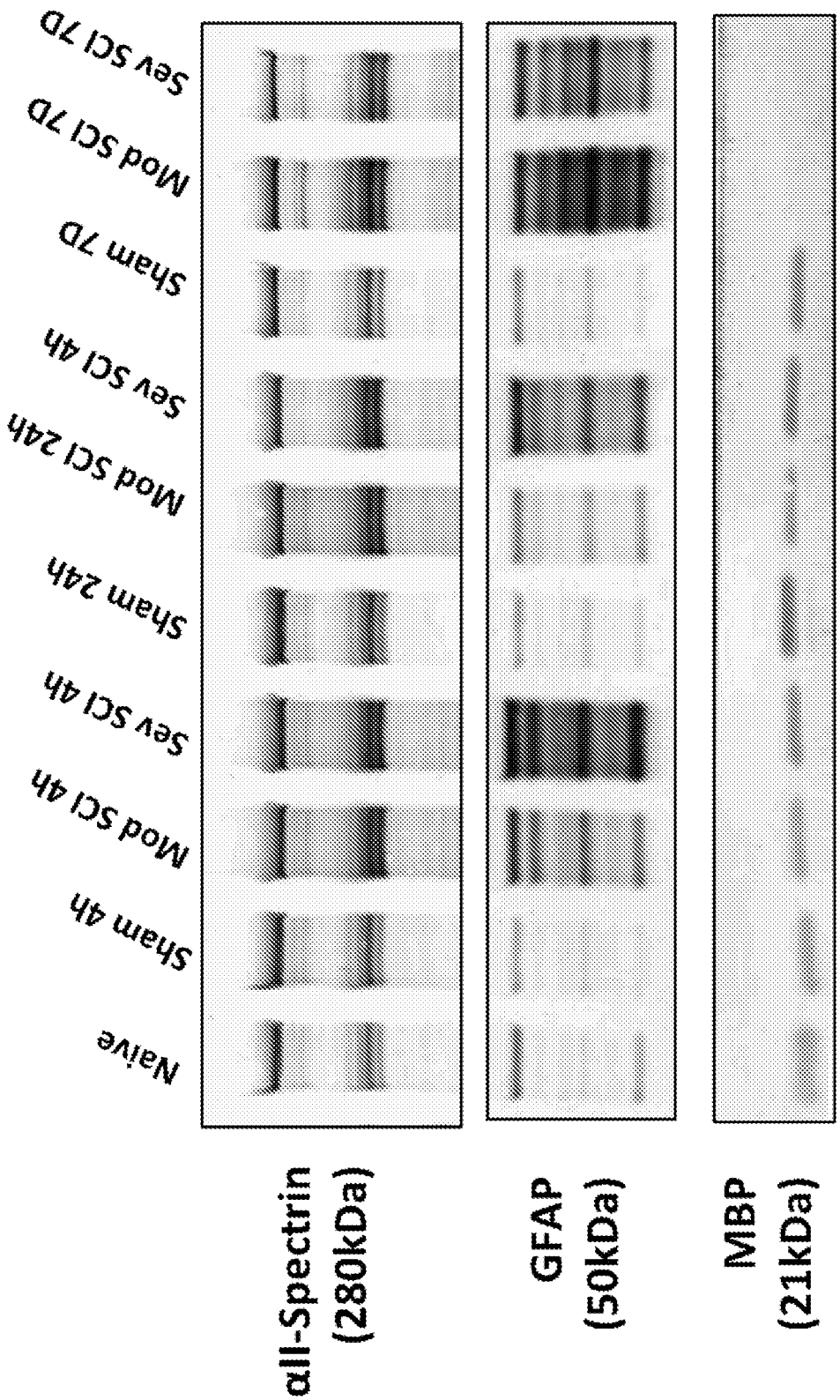
FIGS. 13A-13D show examples of rat spinal cord tissue samples shows elevations of neurotrauma biomarker. MBP (B). SBDP150, SBDP145, SBDP120 (C), GFAP, GFAP-BDP44K, GFAP-BDP40K (D) at 4 h, 24 h and/or 7 d after spinal cord injury. (A) representative Immunoblot examples. Tissue examples are the injury epicenter. *p<0.05 moderate or severe TBI different from respective sham and naïve, (C) alphaII-spectrin, SBDP150, SBDP145 and SBDP120 (bars from left to right), (D) GFAP-50K (intact), GFAP-BDP-44K, GFAP-BDP-40K (bars from left to right).
Figure 13B:
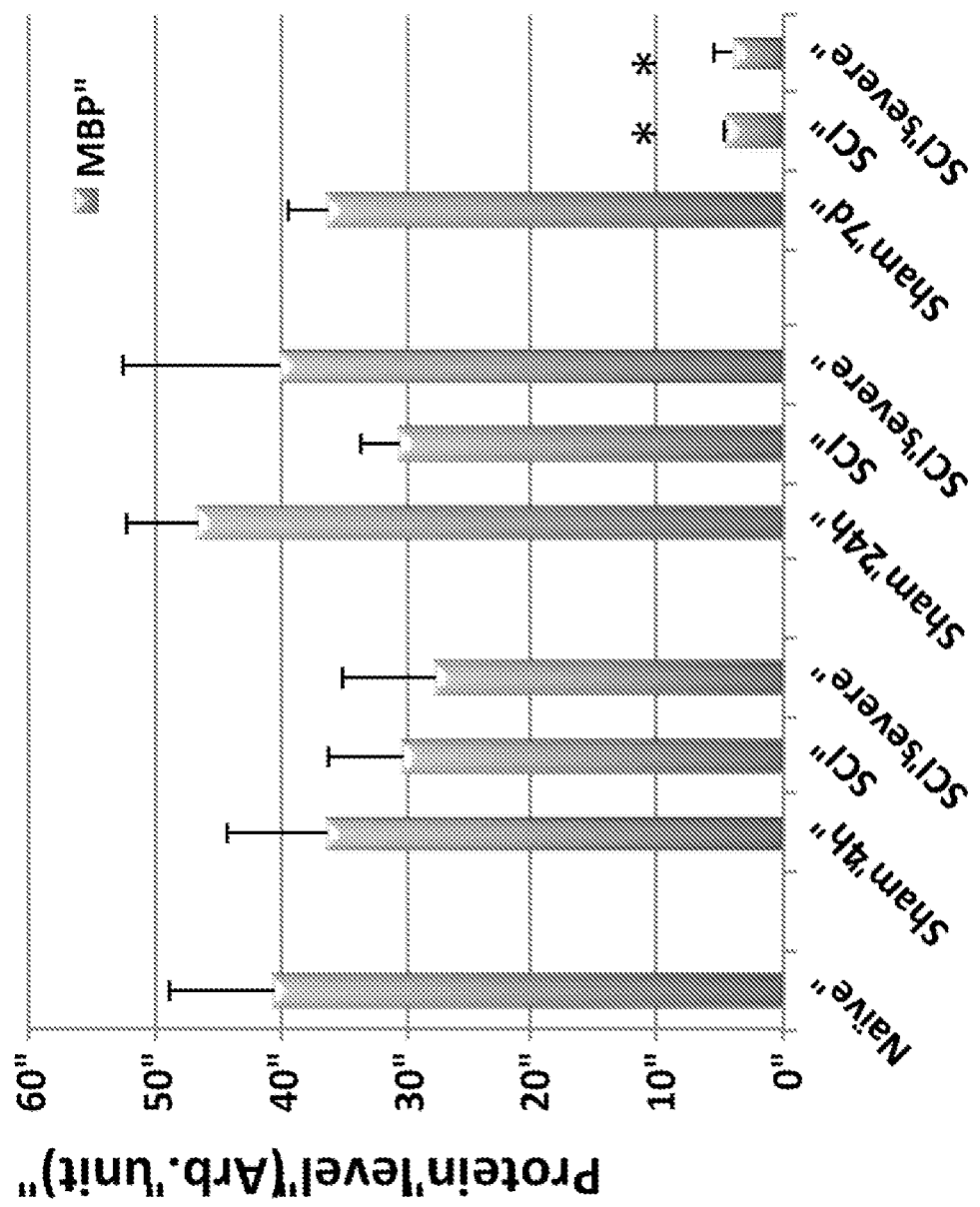
Figure 13C:
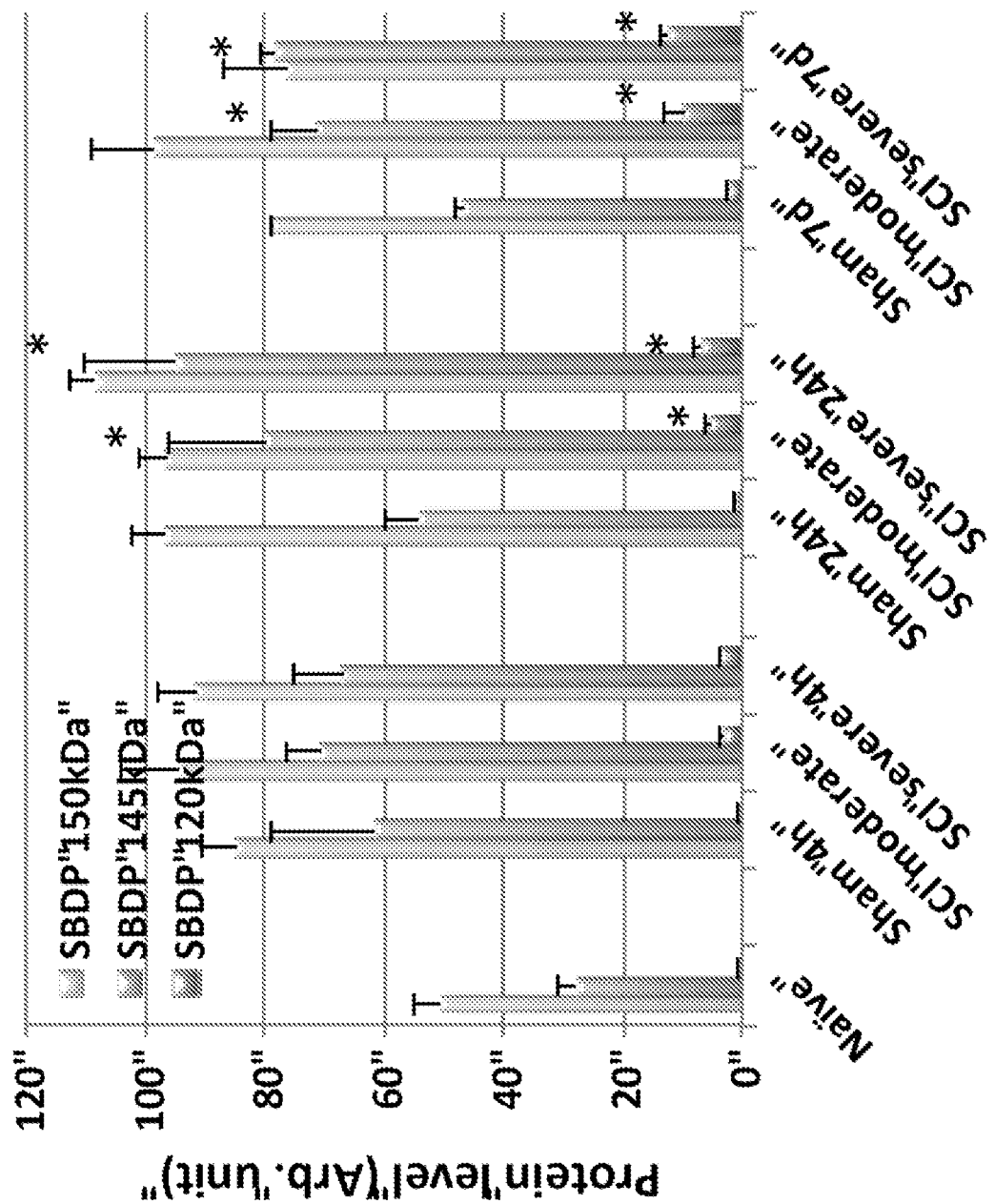
Figure 13D:
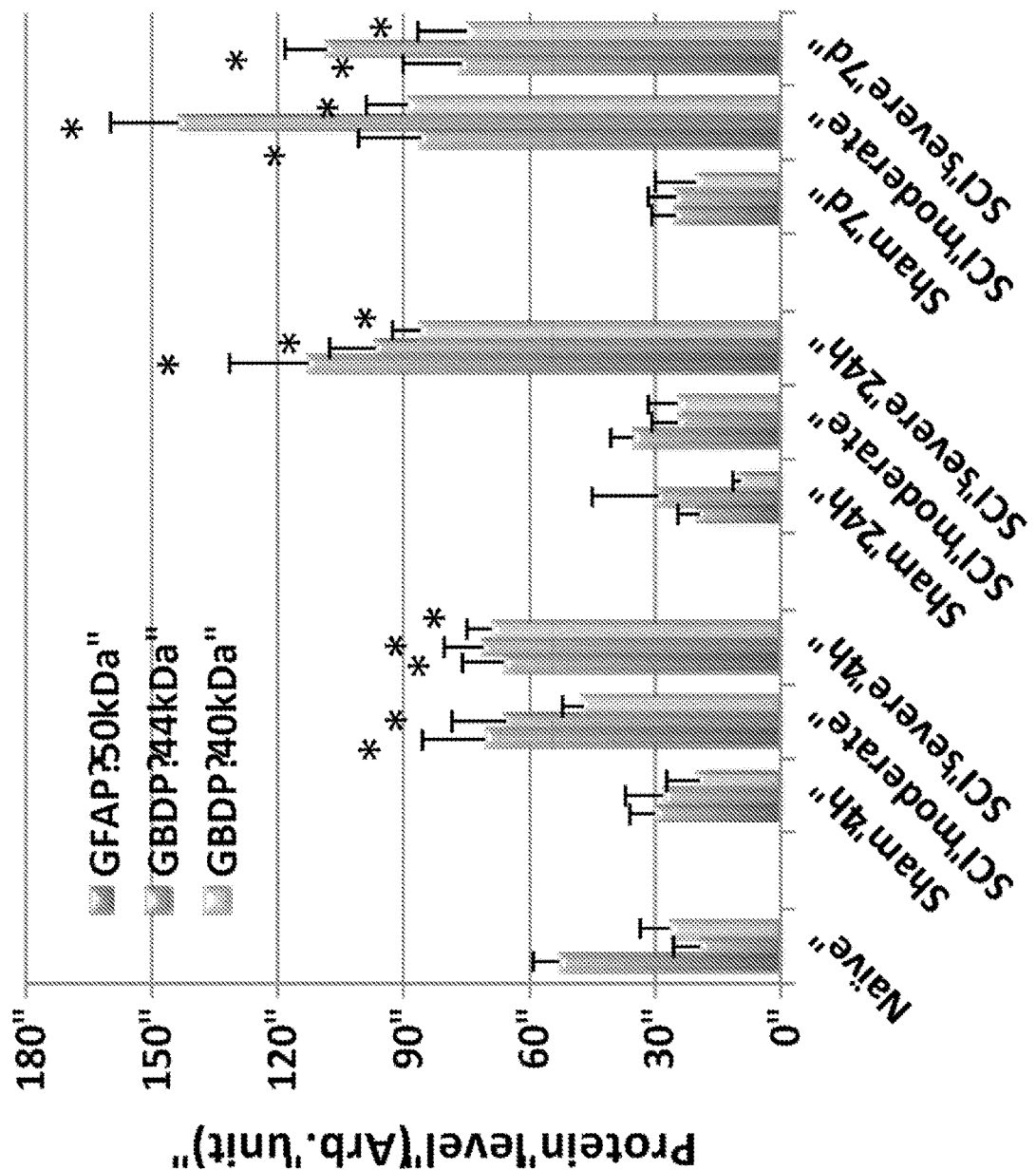

FIG. 12 shows the Tau, P-tau and P-Tau/T-Tau ratio can differentiate control plasma samples vs. plasma samples from CT normal and CT abnormal TBI patients. In other words, (CT−; or cranial Computed Tomography scan normal) are all higher than normal control, while TBI (CT+; or cranial CT scan showing pathology) values are yet higher. This indicates that P-tau/Tau ratio, when used will have strong differential diagnostic ability for acute time points of TBI.

Example 9

Rat Spinal Cord Injury Model
Adult female Fischer rats (220-250 g) were housed according to the National Institutes of Health and United States Department of Agriculture guidelines. Institutional Animal Care and Use Committee of the University of Miami approved all animal procedures. Prior to surgery, rats were anesthetized (45 mg ketamine/kg, 5 mg xylazine/kg) by intraperitoneal injection. An adequate level of anesthesia was determined by monitoring the corneal reflex and withdrawal to painful stimuli for hind limbs. All animals underwent T9-T10 spinal laminectomy. During surgery, rats were placed on a warming pad to maintain body temperature at 37°±0.5° C. Briefly, the rat was placed ventrally on top of a small bit sterile to evaluate the surgical site presenting an adequate exposure of the back anatomy. A 2 cm longitudinal skin incision was centered over the T9 spinus process along the midline. As previously described, perispinal nerves and ligaments were laterally dissected and retracted followed by removal of bony elements of the posterior spine including the spinus process in lamina using a micro Rongiers. The ninth thoracic spinal segment was then exposed without removing the dura mata by removing the dorsal part of the vertebra. The exposed cord was next contused by a 10 gm weight dropped from a height of either 12.5 mm (moderate), or 25 mm (severe) by using the New York University (NYU)-MASCIS impactor (FIG. 16). This model and injury severeties have been shown in Dr. Dalton Dietric's laboratory at University of Miami as well as others to produce well-described pattern of electrophysiological, behavioral and histopathological consequences.

Rat SCI-CSF Collection
Following SCI, CSF samples were drawn at 4, 24 or 48 hrs post-trauma. CSF was collected as previously described. At appropriate time points, injured, sham-injured and naïve animals were anesthetized as described above and secured in a stereotactic frame with the head allowed to move freely along the longitudinal axis. The head was flexed so that the external occipital protuberance in the neck was prominent and a dorsal midline incision was made over the cervical vertebrae and occiput. The atlanto-occipital membrane was exposed by blunt dissection and a 25 gauge needle attached to polyethylene tubing was inserted into the cisterna magna. Approximately 0.1 to 0.15 ml of CSF was collected per rat, then they were removed and immediately euthanized by decapitation. CSF samples were centrifuged at 4,000×g for 4 min. at 4° C. to clear any contaminating erythrocytes.

Sample Preparation
SCI and control samples were rapidly snap frozen in liquid nitrogen and homogenized to fine powder using a small mortar and pestle set over a dry ice. The powder was scraped into chilled microfuge tubes, then lysed with 1% Triton X-100 lysis buffer containing 20 mM Tris HCl pH 7.4. 150 mM sodium chloride (NaCl), 5 mM ethylenediaminetetracetic (EDTA), 5 mM ethyleneglycol bis(aminoethyl ether) tetraacetic acid (EGTA), 10 μL 1M dithiothreitol (DTT), 100 μL, of phosphatase inhibitors (all from Sigma-Aldrich), with a complete mini protease inhibitor cocktail tablet (Roche Biochemicals). Lysis was conducted for 3 hours at 4° C. with hourly vortexing. Lysates were then centrifuged to remove DNA, lipids, and particulates at 15,000 g for 10 min at 4° C. The supernatant was collected and protein content was determined using a DC Protein Assay (BioRad) then, the protein concentration was standardized to 1 μg/μl for immunoblotting analysis. Pooled 1-mg SCI and control samples were-prepared for differential analysis using CAX-PAGE.

Example 10. Human CSF Samples (Control, TBI, SCI)

Archived de-identified CSF samples from traumatic brain injury (TBI) and spinal cord injury (SCI) were used. CSF from a severe TBI study was collected from consenting adult subjects presenting to the Emergency Department. For subjects after sustaining blunt trauma to the head with a Glasgow coma scale (GCS)<8, CSF samples were collected for up to ten days or until an intraventriculostomy (IVC) was no longer clinically indicated. CSF was sampled from the buretrol of the CSF drainage system by a qualified and trained hospital employee according to the hospital's standard procedures. Alternatively, timed CSF samples (10 mL) with a total collection time not exceeding 1 hr were collected into 15-mL conical polypropylene centrifuge tubes (BD Falcon). The CSF samples (5-10 mL) were then centrifuged at 4,000 RPM with a tabletop centrifuge at room temperature for 5-7 minutes to remove loose cells and debris. One mL aliquots of cleared CSF (supernatant) were pipetted into 2 mL cryogenic tubes and snap-frozen and stored at −80° C. in an ultralow temperature freezer until use. For this study, timed CSF samples collected within the first 24 h from injury were used (n=14). The control samples CSF (n=10) were purchased from Bioreclaimation Inc.

In addition, spinal cord injury subjects (SCI) classified as moderate-severe (AIS Grades A, B & C) were recruited at the University of Miami Hospital. Patients were classified according to the American Spinal Injury Association scale (AIS) of impairment (degree of impairment) and AIS on discharge (improvement), urodynamic test (bladder control), somatosensory evoked potential test, and magnetic resonance (MRI) scan. The patients were further classified as traumatic paraplegia or traumatic quadriplegia. For CSF collection, strict aseptic techniques were conducted when a lumbar puncture was performed at L2-3 or L3-4 and ail intrathecal catheter inserted for intrathecal drainage of CSF. Timed CSF samples were diverted to glass tubes (no preservative, heparin or EDTA) for the specified vol. (3 cc), spun at 4,000 RPM at room temperature (to remove loose cells and debris). Aliquots of 500 μL of cleared CSF (supernatant) were placed into 1.2 ml cryovials and stored at −80° C. in an ultralow temperature freezer until used. In this study, CSF samples were collected within 48 h.

Quantitative Immunoblotting Analysis and Antibodies (Tissue, CSF)

Gel Electrophoresis and Electrotransfer. 2× Laemmli sample buffer containing 65.8 m M Tris (pH 6.8), 0.1 mm DTT, 2% SDS, 0.01% bromophenol blue and 10% glycerol in distilled water was used for processing the control and SCI injured samples. Twenty micrograms of protein from each sample was centrifuged for one min at 10,000 g and then resolved by SDS-PAGE on 420% or 10-20% Tris/glycine gels (Invitrogen Life Technologies) at 200 V for 60 minutes at room temperature. The fractionated proteins were transferred to a polyvinylidene difluoride (PVDF) membrane (Invitrogen) by electroblotting using the iBlot Gel Transfer Device (Invitrogen) for seven minutes. Following the transfer, the membranes were blocked in 5% nonfat dry milk in TBST (20 mM 150 Tris-NaCl and 0.003% Tween-20, pII 17.5) for an hour.

Immunoblotting membranes containing tissue protein were incubated with the primary antibody overnight at 4° C. with shaking. Monoclonal anti-mouse α-spectrin (Enzo Life Sciences NY, USA), polyclonal anti-rabbit GFAP (Abeam, Mass., USA), and monoclonal anti-mouse UCHL-1 (EMD Milipore, Mass., USA) were used at a dilution of 1:1000 in 5% milk. Polyclonal anti-rabbit transferrin (Abeam, Mass., USA), polyclonal anti-goat cathepsin D (Santa Cruz Biotechnology, TX, USA), polyclonal anti-rabbit triosephosphate isomerase (TIM) (Santa Cruz Biotechnology, TX, USA), and polyclonal anti-rabbit astrocytic phosphoprotein (PEA-15) (Cell Signaling, MA, USA) were used at a dilution of 1:500, 1:200, and 1:1000, respectively in 5% milk. On the following day, the membranes were washed three times with TEST and probed with an alkaline phosphatase-conjugate goat secondary antibody (EMD Milipore, Mass., USA) at a dilution of 1:5000 in 5% milk for an hour, followed by TBST washing. Immunoreactivity was detected using 5-bromo-4-chloro-3-indolylphosphate (BCIP)/nitroblue tetrazolium phosphatase (Kirkegaard & Perry Laboratories, Gaithersburg, Md., USA). Immunoreactive bands are imaged by digital scanner and protein band density is then quantified by NTH ImageJ software.

Sandwich ELISA Analysis (CSF, Serum, Plasma)

Serum/plasma (30-100 uL), the CSF (0.5-10 uL) and/or brain tissue lysate (2-20 ug total protein equivalent) samples will be processed for 96-well plate sandwich ELISA biomarker analysis format, together with different amount (0.020 ng to 200 ng) of standard biomarker protein (for standard curve generation). This method is used to measure TDP-43 and BDPs, Tau, P-Tau, GFAP and BDP, UCH-L1, cathepsin D, Transferrin, PEA-15, and TPI-1 (TIM). Typically, sandwich ELISA contains one capture antibody and one detection antibody for the target protein. These antibodies can be polyclonal (rabbit) or monoclonal (mouse). The detection antibody is either labeled with florescent dye or coupled to horse radish peroxidase (HRP) or with biotin for streptavidin-HRP based amplification. Assays will be performed on a Spectamax190-Pro microplate reader. Alternately, include P-tau and total Tau (commercially total tau ELISA kits were purchased from called Innotest hTau Ag (#80226) and INNOTEST® PHOSPHO-TAU (181P) (#80323) (Innogenetics). NF-H, GFAP ELISA from Biovendor, UCH-L1 can be from USCNcompany (www.uscnk.us). Alternatively for high sensitivity, P-Tau and Tau, established surround sound fiber optic immunoassay (SOFIA), rolling circle-amplification ELISA method or digital ELISA (Quanterix SIOMA system) are used.

Proteomic Method (T-PAGE RPLC-Tandem) Mass Spectrometry)

CAX-PAGE RPLC-Tandem Mass spectrometry was based on an established method. It includes a comprehensive multi-dimensional separation scheme, with cationic/anionic-exchange (CAX) chromatography, followed by 1D polyacrylamide gel electrophoresis (PAGE) to reduce protein complexity. A reversed phase liquid chromatography-tandem mass spectrometry (LC-MS/MS) proteomic platform is then utilized to examine and characterizes proteome changes associated with SCI.

Cation/Anion Exchange Chromatography Step

The CAX chromatography was performed on a BioRad Biologic DuoFlow system with sulfoproyl SCX (S1) and quaternary ammonium SAX (Q1) modified Sepharose pre-packed ion-exchange columns (BioRad) that were placed in series, and connected in tandem along with a QuadTec UV detector and BioFrac fraction collector. Buffers consisted of 20 mM Tris-HCl (pH 7.5 molecular biology grade, Fisher Scientific) in double distilled water (mobile phase A) and 20 mM Tris-HCl with 1 M NaCl (Fisher Scientific, crystalline 99.8% certified) in double distilled water (mobile phase B). Samples of hog proteins from pooled lysates were injected with an optimized method for differential analysis. The first and second linear gradient steps were from 0 to 5% B, and 5 to 10% in 5 mL each at a flow rate of 1 mL/min; and followed by a six-step gradient, each step increased 5% from 10 to 40% in 1 mL, the last gradient step was from 40 to 50% in 1 ml. Then, the composition was held at 50% B for 1 mL and re-equilibrated to 0% B in 3 mL. The UV chromatograms were monitored at a wavelength of 280 and 214 am for each run. Forty four 1-mL fractions were autonomously collected via the BioFrac fraction collector into 1.5 mL screw-cap microfuge tubes kept on ice.

1D-SDS-PAGE Step

Fractions collected throughout CAX chromatography were concentrated using Millipore centrifugal ultrafiltration units (Millipore Corporation) which have a retaining power for proteins of >3 kDa. Each ultrafiltration unit was treated with 500 μl of 1% SDS (passivation for improved recovery) and soaked for three hours at room temperature, and then all the device units were rinsed with tap water followed by distilled water and spun at 15,000 rpm for 20 min twice. The collected fractions (0.5 ml) were added to the ultrafiltration units and spun at 15,000 rpm for 50 min at 4° C. 2× Laemmli buffer (containing 65.8 mM Tris (pH 6.8), 0.1 mM Dirt 2% SDS, 0.01% bromophenol blue and 20% glycerol in distilled water) was added (20 µl) for each unit and boiled for few seconds prior to collection by centrifugation at 1000 g for 3 min. The protein fractions were run side-by-side (i.e., sham next to SCI 6 h & SCI 24 h), by loading 20 µl of each fraction onto a Criterion TGX Any kD gels (BioRad), 1 mm wide, for 20 min at 300V in a Tris-glycine buffer.

Gel Band Visualization and Quantification Step

The gels were visualized with Coomassie blue stain (BioRad) for differential band analysis. Scanning of the gel and membrane bands was performed using an Epson Expression 8836XL high-resolution flatbed scanner (Epson). UN-SCAN-IT software (version 6.1, Silk Scientific Corporation) was used for quantitative densitometric analysis of selected gel or membrane bands based on their relative intensities. Fold increase or decrease between differential bands was computed by dividing the greater value by the lesser value with a positive sign and negative sign to indicate an increase or decrease after SCI injury. Differential bands were boxed and labeled according to their 2D-position. Gel band intensity was quantified by NIH ImageJ software.

In-Gel Protein Digestion Step

Gels were thoroughly rinsed twice with Optima LC-MS grade water. Differential bands were excised, cut into pieces, placed in 1.5 mL low retention Eppendorf tubes, and washed with 100 µL Optima LC-MS $H_2O$. The gel bands were washed again by 50% 100 mM ammonium bicarbonate (Fisher)/50% acetonitrile (Burdick-Jackson, Optima LC-MS grade). Bands were dehydrated with 100% acetonitrile and dried by Speedvac (Labcoco), and then they were rehydrated with 50 µL of 10 mM dithiothreitol, DTT (Thermo) in 50 mM ammonium bicarbonate and incubated for 30 min a. 56° C. DTT was replaced by 50 µL of 55 mM iodoacetamide (Amersham Biosciences) in 50 mM ammonium bicarbonate and reacted for 30 min in the dark at room temperature for alkylation. Gel pieces were washed with 50 mM ammonium bicarbonate followed by 100% acetonitrile dehydration and dried by Speedvac. For protein digestion, gel pieces were rehydrated with 15 µL of 12.5 ng/uL trypsin solution (Promega Gold) for 30 min at 4° C., and then 20 µL of 50 mM ammonium bicarbonate was added and incubated overnight at 37° C. The hydrophobic peptide extraction was performed with 50% acetonitrile/50% water with 0.1% formic acid. The peptide extract was dried by Speedvac and resuspended in 20 µL Optima LC-MS grade $H_2O$ with 0.1% formic acid after sonication for 15 min and centrifuged at 1500 rpm. Trypsinized band extracts were analyzed by nanospray reversed-phase liquid chromatography and tandem mass spectrometry.

Reversed-Phase Liquid Chromatography and Tandem Mass Spectrometry (RPLC-MS/MS) Step Nano-reversed-phase liquid chromatography tandem mass spectrometry was employed for protein separation and identification. Nanoflow was performed on a NanoAcquity UPLC (Waters, Milford, Mass., USA); the autosampler was used to load two microliters of each sample onto a 5 µm particle size Symmetry 180 µm×20 mm C18 trapping column at 4 µL/min for 10 min. Then, the sample plug was loaded onto a 1.7 µM particle size BEH130 C18 100 µm×100 mm analytical column at 300 nL/min. The mobile phase consisted of solvent A (water with 0.1% formic acid) and solvent B (acetonitrile with 0.1% formic acid). Separation was achieved within a run dine of 115 min at a flow rate of 300 nL/min. The first linear gradient was from 1% to 40% B over 90 min, the second linear gradient was from 40% to 100% B over 5 min and held for 5 min before returning to initial mobile-phase composition (1% B). Tandem mass spectra were collected on LTQ-XL (Thermo, San Jose, Calif., USA) using a Data Dependent Acquisition method in Xcalibur 2.0.7 (Thermo), in which data dependent scanning was specified as a criteria to select the top 10 most abundant ions using 11 separate scan events at a given chromatographic time point (115 min) for subsequent analysis. The mass spectrometer was set to perform a full-scan and subsequently MS/MS scans on the ten most intense ions in the full-scan spectrum MS (scan event 1) with Dynamic Exclusion enabled. Dynamic Exclusion temporarily puts a mass into an exclusion list after its MS/MS spectrum is acquired, providing the opportunity to collect MS/MS information on the second most intense ion from the full-scan spectrum MS (scan event 1). All MS/MS spectra were analyzed using Proteome Discoverer 1.3 (Thermo). SEQUEST (version: 1.3.0.339) and X! Tandem (version: CYCLONE (2010.12.01.1)). Database search engines were set up to search a trypsin-Indexed uniprot-Rattus+norvegicus fasta (unknown version, 35126 entries). The search was achieved using the average mass for matching the precursor with a fragment ion mass tolerance of 0.8 Da and a parent ion tolerance of 2.00 Da. Carbamidomethylation of cysteine was selected as a static modification, while the oxidation of methionine was selected as a dynamic modification. Using the output from SEQUEST and X! Tandem, Scaffold (version: Scaffold_3.3.3, Proteome Software) was used to validate, organize, and interpret mass spectrometry data. Peptide identifications were accepted if they could be established at greater than 95.0% probability as specified by the Peptide Prophet algorithm. Protein identifications were accepted if they could be established at greater than 99.9% probability and contained at least 2 identified peptides.

With, the use of rat SCI tissue (caudal segment from epicenter, 4 hours, day 1 and day 7 post-injury), and CAX-PAGE RPLC-tandem mass spectrometry proteomic method, protein biomarker candidates could be identified. Additional spinal cord tissue (caudal, and rostral segment and epicenter segment, Cerebrospinal fluid (CSF) and blood samples) form the rat study and CSF and serum/plasma from injured human patients was also used for clinical studies of SCI patients. Panels of SC candidate biomarkers were identified that can be used to correlate with, disease progression or to identify potential SCI therapeutic targets (shown in Tables 2, 3). This was followed by cross-validating these biomarker candidates in biofluid from human TBI subjects. The identified biomarkers have diagnostic, prognostic and managing utilities for all neurotrauma types (including both TBI and SCI).

Example 11. CAX-PAGE Differential Neuroproteomic Analysis

CAX chromatography was employed to fractionate SCI samples and control proteins according to their surface charges followed by 1D gel electrophoresis to separate proteins based on their molecular weight. Pooled spinal cord tissue lysate samples of rostral regions collected from the SCI rat contusion model SCI at 4 h, 24 h, and 7 d time points (n=5, each) were first subjected to CAX chromatography ion exchange (CAX separation has the ability of retaining both positively and negatively charged proteins). There were chromatographic differences with high protein recovery for differential expression profiling of sham and SCI rat lysates (UV chromatograms at a wavelength of 280 nm) which were attributed to the injured spinal cord proteome. Both sham and SCI proteins were distributed into 28 fractions (1 ml) and collected after using tandem CAX columns. Protein fractions were analyzed side-by-side on a 1D-gel for differential comparison, 24 h sham vs. 24 h SCI and 7 d, sham vs. 7 d SCI. Differential bands were boxed and labeled according to their 2D position with number and letter (e.g. the top band excised from the lane of fraction X was labeled XA). ImageJ densitometry software was used for quantification of selected differential gel band intensities to derive the relative fold increase or decrease.

Differentially displayed bands were selected from the 1D-gels and cut into pieces for proteomic analysis, then trypsinized. Trypsinized peptides were separated by reversed-phase liquid chromatography online with tandem mass spectrometry (RPLC-MS/MS) for protein identification. All MS/MS spectra were analyzed using Proteome Discoverer 1.3 (Thermo), SEQUEST and X! Tandem database search engines have been utilized to search the experimental spectra against a rat indexed database and validated by Scaffold 3. Based on identified unique peptides, sequence coverage, and molecular weight gel band, the protein biomarker candidates were isolated in each band.

41 and 38 proteins for 24 h and 7 d, respectively reported in Tables 2 and 3 were identified by the analysis to be differentially expressed between sham and SCI. The identified proteins were grouped as having increased (22 & 22 proteins) or decreased (19 & 16 proteins) abundance for 24 h and 7 d, respectively. The proteins with increased levels post-SCI (24 h) included aldehyde dehydrogenase 4 family, member A1 (Aldh4a1) protein (Fragment), LOC367586 protein, aminoacylase-1A, transketolase, Gamma-enolase, elongation factor 2, protein Tln1, and peroxiredoxin-2. After 7 d the list included aldo-keto reductase family 1, member B10 (aldose reductase), pyruvate kinase PKM, Acyl-CoA synthetase family member 2, mitochondrial, and protein-L-isoaspartate (D-aspartate, O-methyltransferase). Among the proteins with decreased levels post-SCI (24 h) were isocitrate dehydrogenase: [NADP], mannose-6-phosphate isomerase, pyridoxal kinase, stathmin, and peripheral myelin protein 2 (Pmp2). After 7 d, alcohol dehydrogenase [NADP(+)], L-Lactate dehydrogenase B chain, ribosyldihydronicotinamide dehydrogenase [quinone], and ATP citrate lyase-CRA a isoform. Some differentially expressed proteins are common in both 24 hand 7 d time points, annexin A1 & A2, glyceraldehyde-3-phosphate dehydrogenate, Pgm1 protein (Fragment), glutathione S-transferase Mu 5, triosephosphate isomerase, and transferrin (serotransferrin). Also, the presence of the same proteins were identified in both up and down regulated bands. This can be explained as families of proteins (Ex: annexin 1&2), mobility in CAX or PAGE would-Vary with (protein modification, or altered by proteases (BDP) so these proteins could elute in different fractions due to differences in surface charge. Between the 1 day and 7 day SCI increased protein level groups; we found that 7 of them overlapped (glyceraldehyde-3-phosphate dehydrogenase, Alcohol dehydrogenase [NADP(+)], annexin A2, Pgm1 protein, triosephosphate isomerase (TIM), glutathione S-transferase Mu 5, serotransferrin (transferrin)). Between the 1 day and 7 day post-SCI decreased protein level groups, only two proteins were on both lists (annexin A2 and Pgm1 protein).

Since necrosis, apoptosis, and cell death pathways are activated early after SCI damage, known biomarkers, spectrin breakdown products (SBDP) SBDP-150 and SBDP-145 were targeted as reporters of calpain-mediated necrotic injury; SBDP-120 as a marker for caspase-mediated apoptosis, and GFAP breakdown products GBDP-44; BDP-40 as reporters of calpain-mediated glial injury, to validate the potential value of the new identified candidates. The candidate protein selection was based on the spinal cord specificity, antibody availability, and levels of peptide abundance. Five biomarker candidates were selected; blood brain barrier (BBB) located transferrin, lysosomal protease cathepsin D, trisephosphate isomerase (TPI-1), astrocytic phosphoprotein-15 kDa (PEA-15), and potential stroke biomarket nucleoside diphosphate kinase A to confirm their protein alterations associated with SCI. The proteolytic damage markers to the spinal cord structural and cellular components were validated by quantitative immunoblotting using specific antibodies for each protein. Differential changes in the above mentioned proteins were confirmed by using (tissue lysate and CSF) sham and SCI (4 h, 24 h and 7 d) groups in the two severity points (moderate and severe) in rat spinal cord tissue (rostral, epicenter) and CSF.

Example 12

FIG. 13 shows the SCI-tissue immunoblotting validation of representative protein biomarkers. In upper-left panels, time course of post-SCI biomarkers validation illustrated by Western blot of rat spinal cord tissue (epicenter) lysate of rostral section (sham, and two SCI severity) collected at three time points (4 h, 24 h and 7 days), the known markers probed are alphaII-spectrin and GFAP and MBP. In the remaining panels, immunoblotting quantification of spinal cord tissue lysate samples (sham and two SCI severity levels at 3 time points) for alphaII-spectrin-breakdown product SBDP150, 145, 120, GFAP and GFAP-BDP (44 and 40 KDa), and MBP biomarkers. All biomarkers are elevated after injury except that MBP marker is reduced in tissue at 7 day after SCI.

Figure 14:
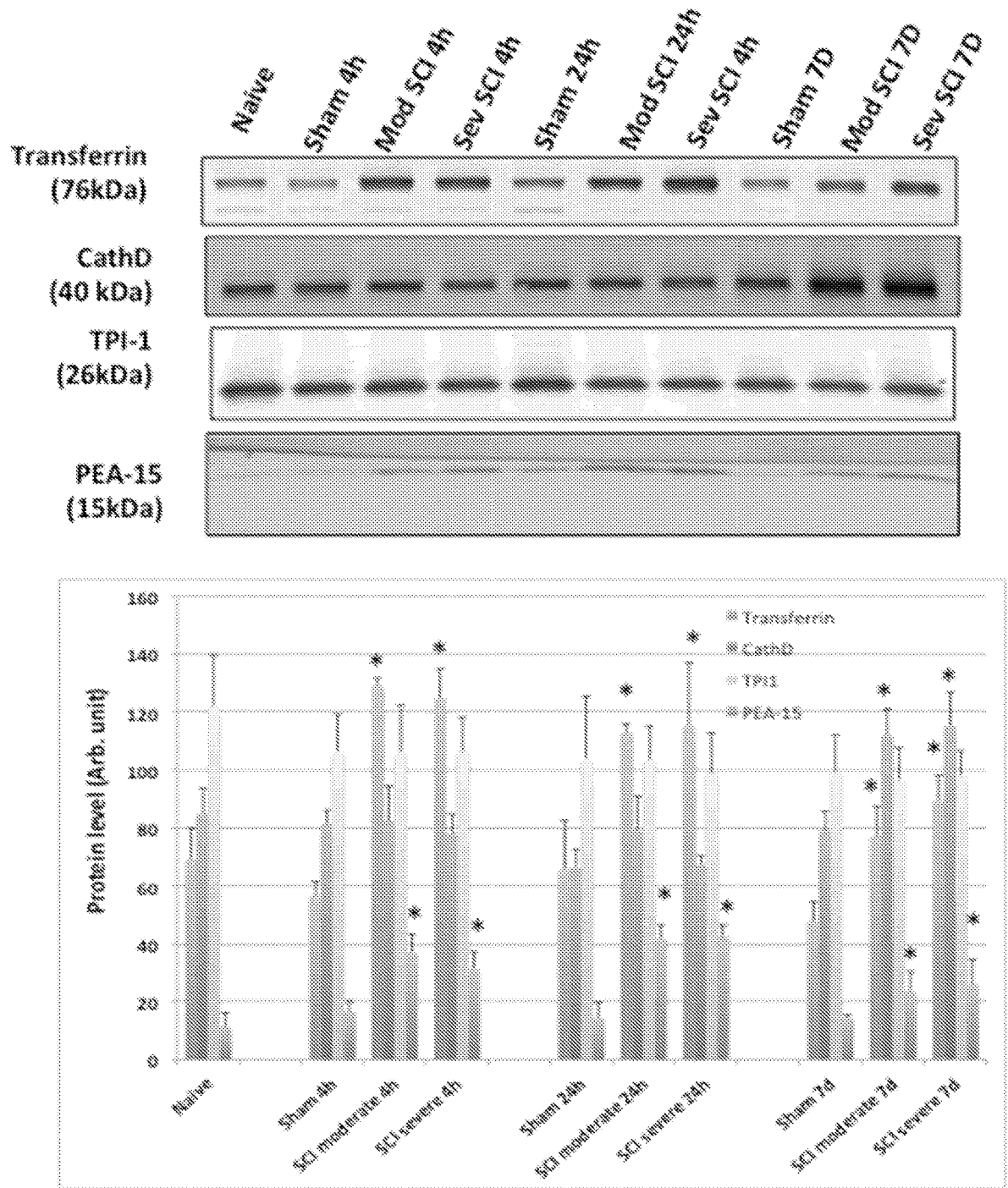
FIG. 14 shows examples of rat spinal cord tissue samples shows elevations of novel biomarker Transferrin, Cathepsin D (CathD) and Phosphoprotein enriched in astrocytes 15
Figure 15A:
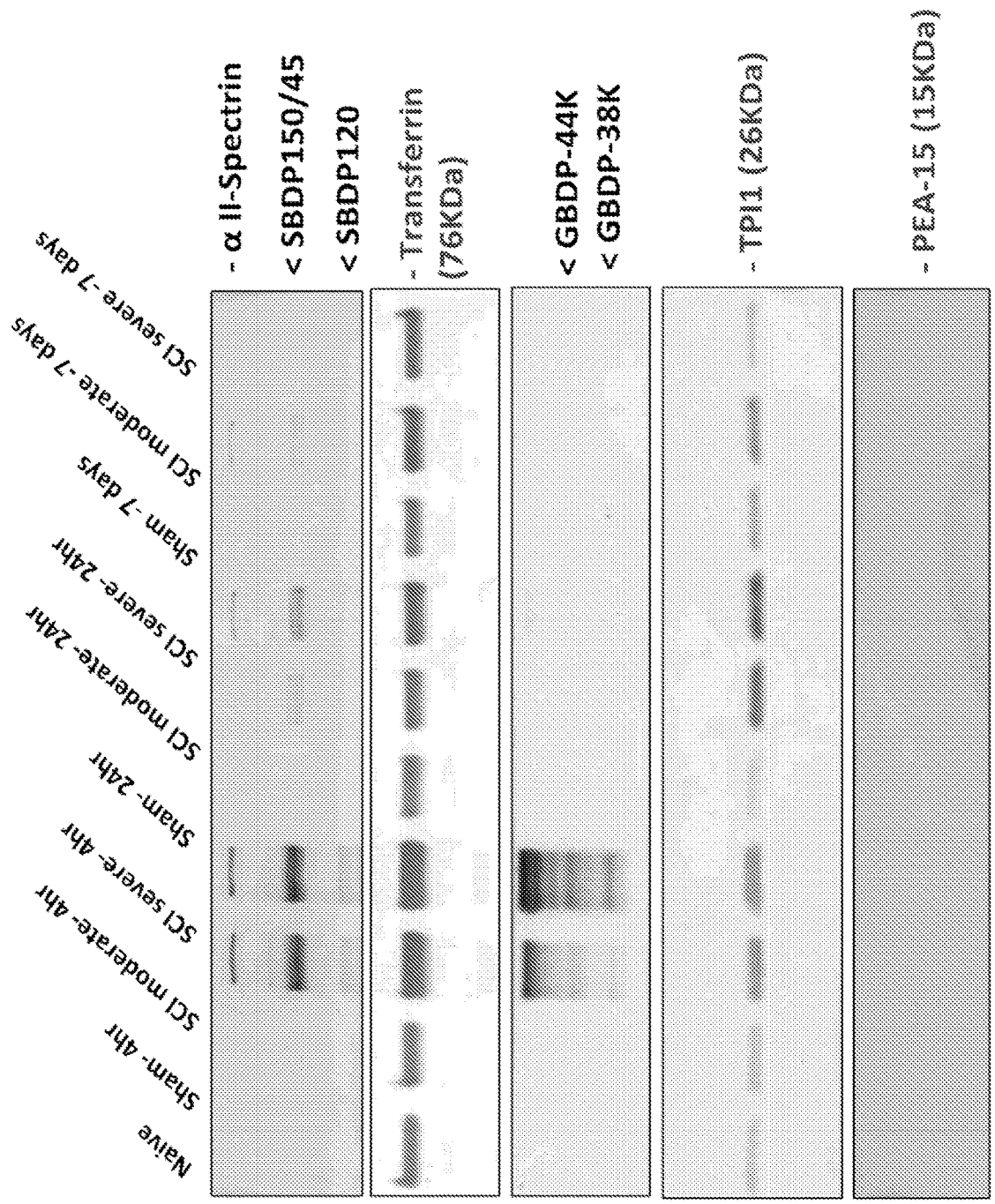
Figure 15B:
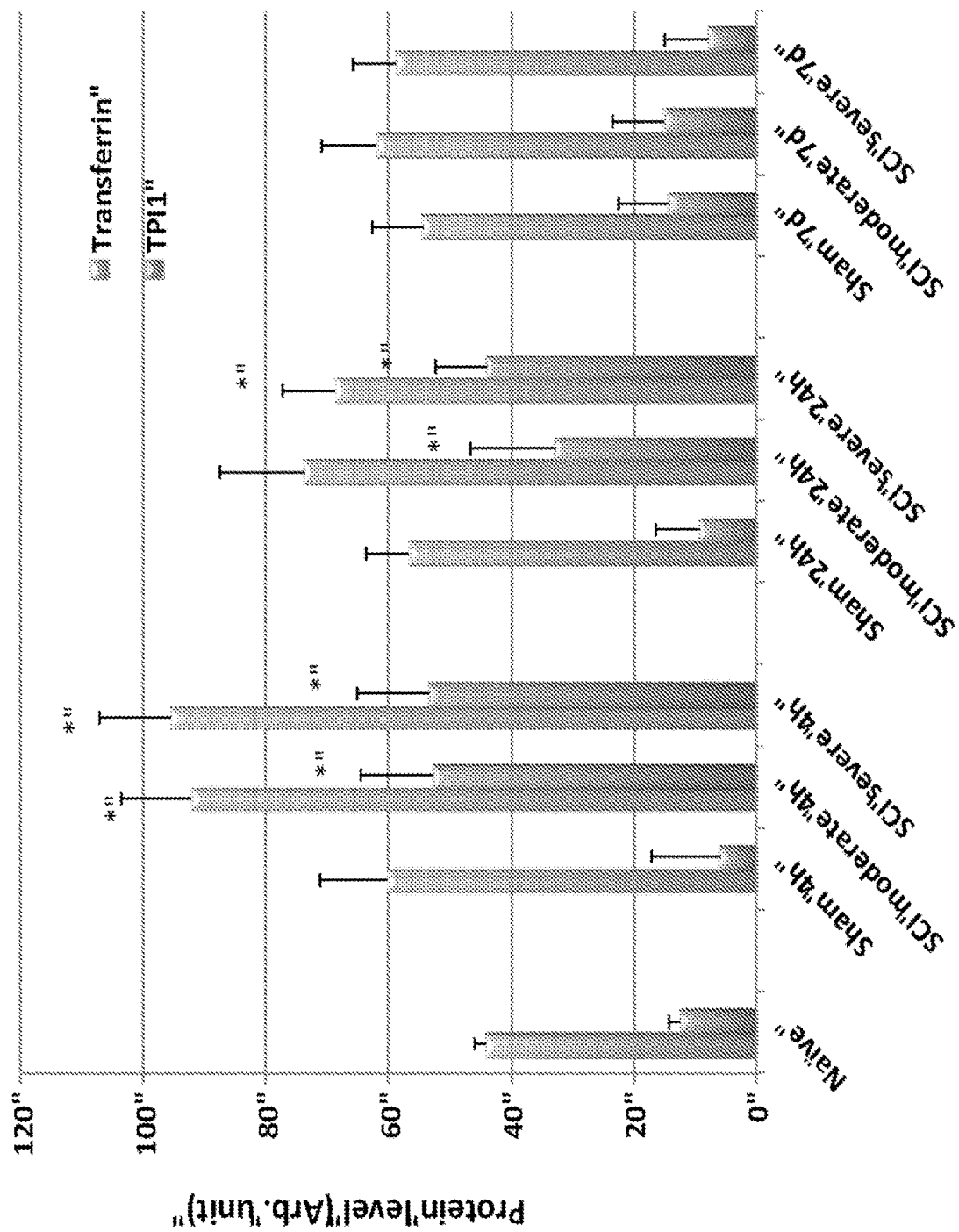
Figure 15C:
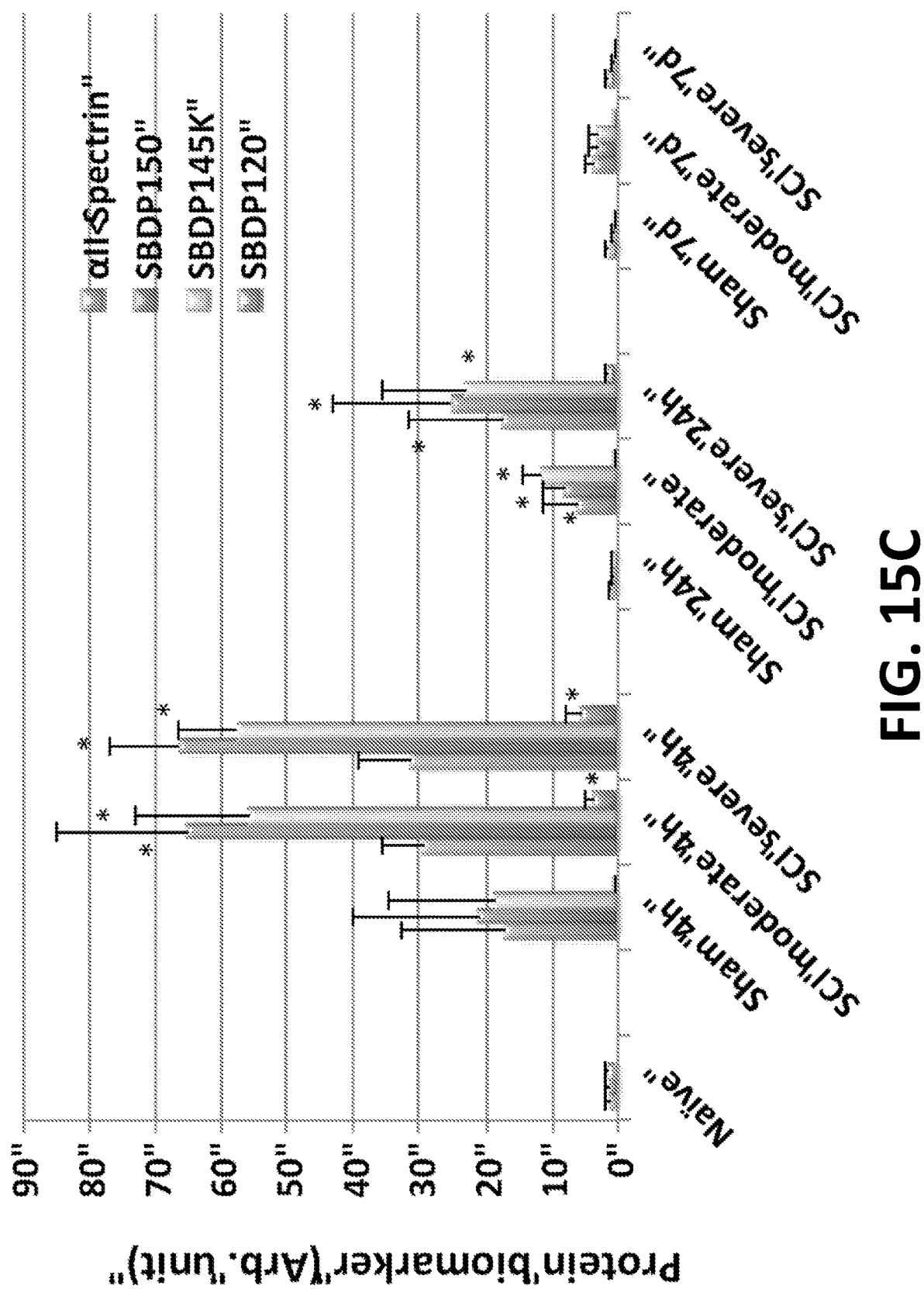
Figure 15D:
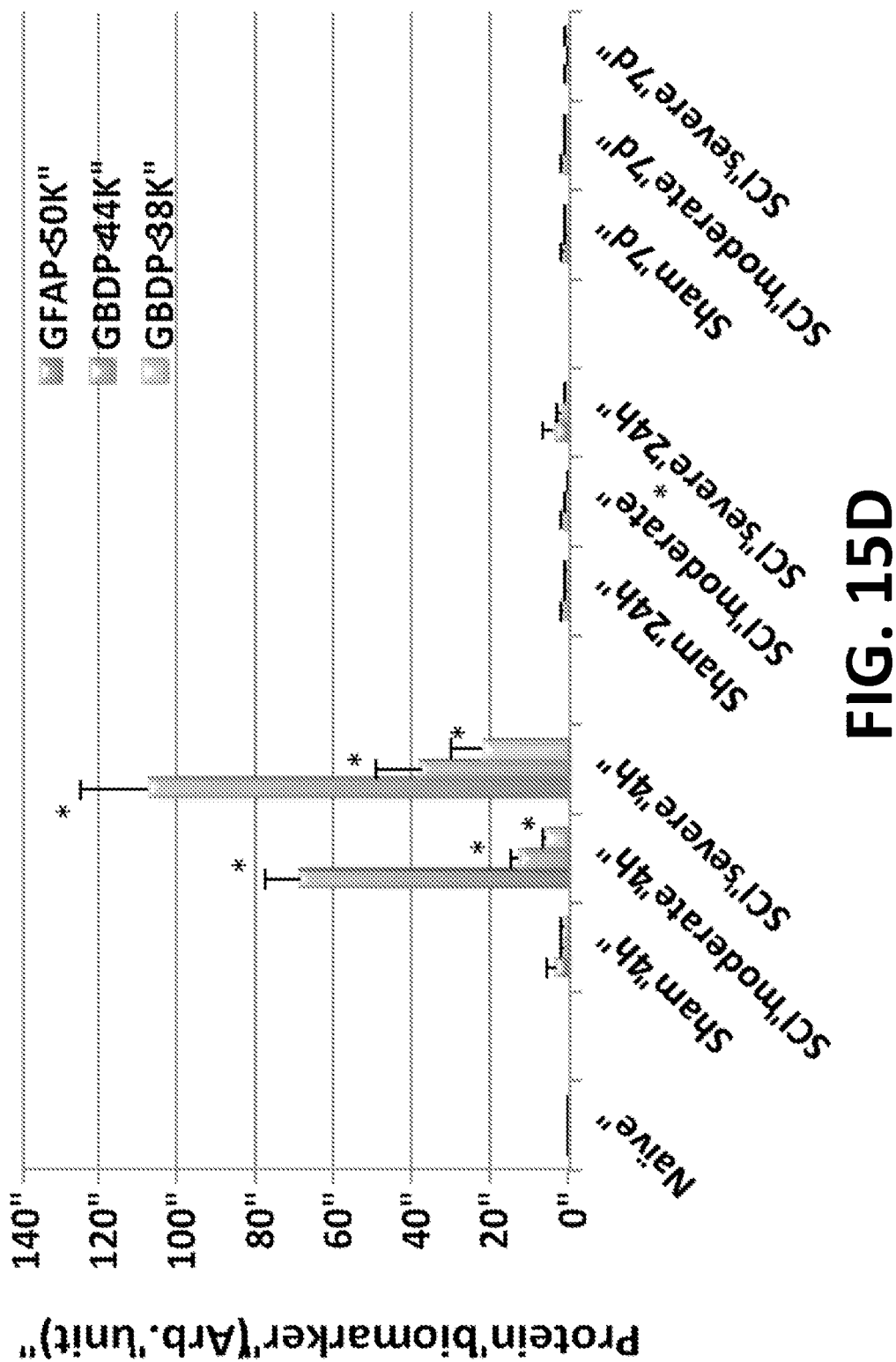

FIG. 14 shows the SCI-tissue immunoblotting validation of representative protein biomarkers. In upper panel, time course of post-SCI new biomarker candidates validation illustrated by Western blot of rat spinal cord tissue (rostral) lysate of rostral section (sham, and two SCI severity) collected at three time points (4 h, 24 h and 7 days), Novel candidate markers probed include transferrin, cathepsin D, TPI-1 and PEA-15. Western blot of carbonic anhydrase. LE served as a loading control (not shown) In bottom panel, immunoblotting quantification of spinal cord tissue lysate samples for post-TBI increases of cathepsin D, TPI-1 and PEA-15 biomarkers. All markers are elevated at 4 h and 24 h post-SCI, except that CathD has delayed increase after injury (at day 7).

FIG. 15 further illustrates the detectability of representative SCI biomarker elevations in rat CSF after SCI by immunoblotting method. In panel (A) Time course of post-SCI biomarkers release and new candidate marker validation illustrated by Western blot quantification of rat spinal cord CSF samples (sham, and two SCI severity) collected at three time points (4 h, 24 h and 7 days), the markers probed are alphaII-spectrin (SBDPs), Transferrin, GFAP, GFAP-BDPs and TPI-1. The detection method shown is quantitative immunoblotting (western blots) Other methods such as sandwich ELISA method or amplified sandwich ELISA can also be used.

FIG. 16 shows the time course of alphaII-spectrin-BDPs (SBDPs), Transferrin, GFAP GFAP-BDPs and TPI-1, CathD and PEA-15 biomarker release into human CSF (2 patients) after SCI, detected by immunoblotting.

Figure 17B:
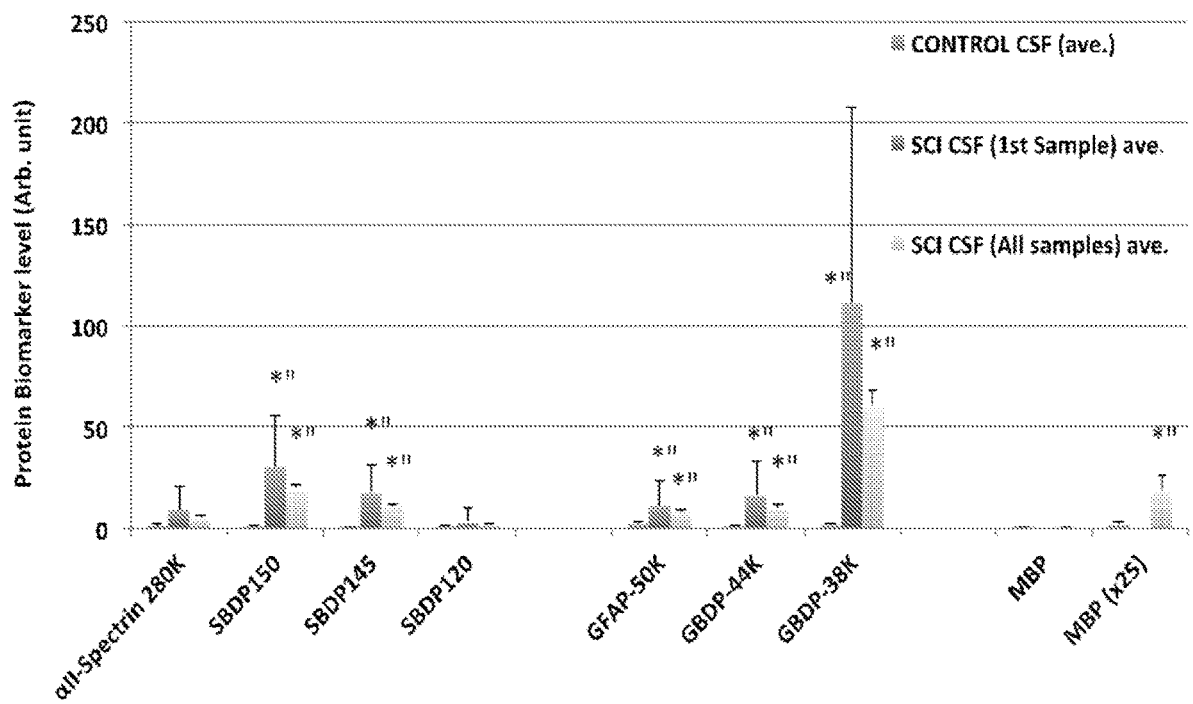

FIG. 17 shows parallel time course of release of similar SCI biomarkers (alphaII-spectrin-BDPs (SBDPs), Transferrin, GFAP, GFAP-BDPs and TPI-1, CathD and PEA-15) into human CSF after SCI, detected by immunoblotting and processed for quantification (n=12-15 patients). In this example, the detection method shown is quantitative immunoblotting (Western blots). Other methods such as sandwich ELISA method or amplified sandwich ELISA can be used.

FIG. 18 shows human spinal cord injury CSF and serum GFAP levels from the same subject at same time points with a correlation (n=12 subjects), despite that GFAP levels in CSF are about 10-100 higher than those found in serum. If CNS injury biomarkers are shown to be elevated in human CSF samples, they are expected to be elevated in blood (e.g. serum, plasma samples) in a quantifiable manner also.

Example 13. Neuro-Systems Biology (SB) Pathway and Interactome Analysis

Various types of brain injury and SCI biomarkers (Tables 4, 5, 6) identified are applied to Systems Biology (SB) to derive interactome maps (FIGS. 19 and 20) which might help identify additional unobvious pathways or hot spots. Systems Biology (SB) is a new field of science that analyzes the relationships among all the individual components in a biological system (genes, proteins, metabolites etc.) by quantitative description of the interaction among them. The goal of this approach is to develop computational models of these systems, therefore the responses of the system to any kind of perturbation; for example, environmental disturbance, genetic mutation etc., can be predicted. Pathway analysis of various biomarker types have been or can be used to revealed association with CNS disorders; including neurodegenerative disorders, stroke, traumatic brain injury (TBI) and spinal cord injury (SCI).

Experimental Systems Biology Method

An SB approach was utilized to determine the critical biochemical pathways in the pathogenesis of brain injury and SCI. Pathway Studio software 9.0 (Ariadne Genomics Inc. MD, USA) was employed to identify significant pathways and interactome across individual samples as a signature to predict clinical outcomes. Pathways of brain injury systems and SCI identified candidate biomarkers were generated. Various brain systems biomarkers including acute injury, neuroinflammation, neuroregeneration, and neurodegeneration) markers (Table 2) are from literature and then used to generate brain injury systems biomarker list (Table 3). SCI candidate biomarkers can be identified (Table 4) and input separately into Pathway Studio for SB analysis.

Neuro-Systems Biology Analysis.

Pathway Studio 9.0 has been utilized to search for possible protein-protein interactions, common regulators, cell processes, and related pathways for associations among the various brain injury systems biomarker proteins (Table 4, Table 5). The network was generated using the "Shortest Path" algorithm to map interactions between altered proteins. Several processes believed to be central to the pathogenesis of TBI disorders were identified using this search. Some examples of those processes include cell death, inflammation, oxidation, and apoptosis (FIG. 19).

Similarly, SCI candidate biomarkers were identified using a rat model of SCI (Table 6) and these candidate biomarker proteins are input into Pathway Studio for SB analysis. Using "Shortest Path" algorithm, potential interactions among these protein components were mapped (FIG. 20). Several Non-redundant converging pathways were identified—they highlight the potential role of neuronal death mechanism, cell invasion, oxidative stress, and cell differentiation pathway as main players on SCI. Additional data and literature-mining and new experiments can be done to further understand the pathological pathways involved in spinal cord structural and functional changes, SCI recovery, complications and other SCI-related co-morbidities. Such maps can also brave utilities in the diagnosis, prognosis and management of SCI, TBI or similar CNS injury. These SB methods allow the identification or additional unobvious biomarkers for CNS injury. Useful Biomarkers suggested by this SB approach were S100b, IL-6, iba-1, visinin-like proteins and BDNF and Pro-BDNF proteins (Table 1).

Example 14. Additional TBI and SCI Biomarkers and Validation

FIG. 21 shows that human spinal cord injury CSF samples show significant elevations of novel SCI biomarker S100b and IL-6, SCI patient CSF samples are collected from day 1 to day 6 after injury. Shown here are all samples from patients n=12-15 and control n=10-12.

FIG. 22 shows an example of detecting; elevations of Transferrin, CathD, TPI and PEA-15 and CNS injury biomarkers GFAP and GFAP-BDP in acute human TBI CSF samples as compared to normal controls (N=10-14). Based on data on SCI CSF (FIGS. 14, 16), Transferrin, CathD, TPI, and PEA-15 were identified as novel neuroinjury biomarkers. Since both SCI and TBI are similar and related neurotrauma, it is likely that Transferrin, CathD, TFI-1 and PEA-15 will also be elevated in biofluids in TBI patients (such as CSF). Here in TBI CSF, the same markers Transferrin, CathD, TPI-1 and PEA-15 elevation in fact supports this notion (GFAP and GFAP-BDP were assayed also as benchmark).

FIG. 23 shows that human traumatic brain injury and spinal cord serum samples show elevations of novel biomarker BDNF (mature form) when compared to control serum samples. TBI and SCI patient samples used were collected within 24 h after injury. Shown are SCI and TBI n=10, control n=16. TBI and SCI BDNF levels are higher than control serum. BDNF is a member of the neurotrophin family and related to Nerve Growth Factor. BDNF are found in the brain and the periphery, BDNF acts on neurons of CNS and the peripheral nervous system (PNS), supporting the survival of existing neurons, and facilitating the growth and differentiation of new neurons and synapses. In the brain, it is active in the hippocampus, cortex, and basal forebrain. It is also expressed in the retina, motor neurons, and also present in the kidneys, prostate and saliva.

FIG. 24 shows human traumatic brain injury serum compared to a Control serum profile of biomarker pro-BDNF. BDNF also exists as pro-BDNF form (precursor). TBI patient samples used were collected at 24 h and at 240 h (10 days) after injury. TBI n=20, control n=16. Pro-BDNF levels were detectably higher at 24 h and at 240 h after TBI. Thus the combined use of assaying Pro-BDNF and BNDF might be used is tandem biomarkers for TBI or SCI.

FIG. 25 shows human and mouse traumatic brain injury serum compared to control scrum profile for novel microglial biomarker Iba-1. The left panel shows serum samples from naïve mousse vs. mice with controlled cortical impact (TBI, CCI) at day 1 and 7 post-injury (n=6) each assayed for iba-1 levels. Iba-1 levels were detectable in mouse serum and found elevated in TBI serum at day 1 and day 7 post-injury (*$p<0.001$) as compared to naïve control serum levels. The right panel shows Severe TBI patient samples collected at 24 h at 168 h (7 days) after injury. TBI n=12, control n=10. Iba-1 levels were detectable in human serum and found elevated in TBI at 24 h (p<0.005) and TBI-168 h (***p<0.001) as compared to control.

FIG. 26 shows Visinin-like protein-1 (VSNL1) elevations in human TBI CSF and human spinal cord injury and TBI serum as compared to respective controls. Left panel shows CSF samples from control or TBI (day 1) were assayed for VILIP-1 levels. Right panel shows severe SCI and TBI patient serum samples used were collected at 24 h after injury (n=6-8) where VILIP-1 levels were detectable in human serum and found elevated in SCI at 24 h (6.07±1.03 pg/mL; mean+SEM) and TBI at 24 b (7.06±0.63) as compared to control serum group (5.33±0.50). This is a novel finding, although VILIP-1 was suggested to be a possible marker for Alzheimer's disease (Lee et al. Clin Chem. 2008 Aug. 14; 54(10):1617-23), there are no prior data to suggest that it might be a TBI or SCI biomarkers. VSNL1 is a member of the visinin/recoverin subfamily of neuronal calcium sensor proteins. The encoded protein is strongly expressed in granule cells of the cerebellum and also in other neurons in the rest of the brain.

The data also infer that not only that VILIP-1 is a TBI/SCI biomarker, but also that other visinin-like proteins that are abundant in the CNS (VSNL2, VSNL3) (Table 1) are also possible biomarkers for CNS injury.

What is claimed is:

1. A method of detecting a biomarker related to traumatic injury to the central nervous system in a subject having a traumatic injury to the central nervous system or suspected of having a traumatic injury to the central nervous system, comprising:
    (a) obtaining a first biological fluid sample selected from the group consisting of blood, serum, plasma, and cerebrospinal fluid from the subject up to 1-3 days after the traumatic injury or suspected traumatic injury to the central nervous system;
    (b) contacting the biological fluid sample with a first antibody that specifically recognizes the biomarker P-Tau; and
    (c) detecting the level of binding of the first antibody to the biomarker in the biological fluid samplessample indicating the traumatic injury to the central nervous system.

2. The method of claim 1, further comprising:
    (d) contacting the biological fluid samples with a second antibody that specifically recognizes a second biomarker selected from the group consisting of visinin-like protein (VILIP)-1, VILIP-2, VILIP-3, brain-derived neurotropic factor (BDNF), pro-BDNF, ionized calcium-binding adaptor molecule-1 (iba-1), and phosphoprotein enriched in astrocytes 15 (PEA-15), and neurofilament protein-H, -M, or -L; and
    (e) detecting the level of binding of the second antibody to the second biomarker in the biological fluid samples.

3. The method of claim 1, further comprising:
    (d) contacting the biological fluid samples with a second antibody that specifically recognizes a second biomarker selected from the group consisting of glial fibrillary acidic protein (GFAP) and neurofilament protein-H, -M, or -L; and
    (e) detecting the level of binding of the second antibody to the biomarker in the biological fluid samples.

4. The method of claim 1, further comprising:
    (d) contacting the biological fluid samples with a second antibody that specifically recognizes the biomarker total Tau (T-Tau); and
    (e) detecting the level of binding of the second antibody to the biomarker in the biological fluid samples.

5. The method of claim 1, further comprising:
    (d) contacting the biological fluid samples with a second antibody that specifically recognizes the biomarker T-Tau; and
    (e) detecting the level of binding of the second antibody to the biomarker in the biological fluid samples.

6. The method of claim 5, further comprising:
    (f) obtaining one or more additional biological fluid samples from the subject at later times, contacting the biological fluid samples with a second antibody that specifically recognizes the biomarker T-Tau, and detecting the level of binding of the second antibody to the biomarker in the biological fluid samples.

7. The method of claim 6, wherein the later times are selected from one or more of 5 days, 14 days, 1 month, 3 months, and 6 months.

8. The method of claim 6, further comprising:
    (f) calculating the P-Tau to total Tau ratio for each of the biofluid samples.

9. The method of claim 5, further comprising:
    (f) calculating the P-Tau to total Tau ratio for each of the biofluid samples.

10. The method of claim 1, further comprising:
    (d) contacting the biological fluid samples with a second antibody that specifically recognizes the biomarker neurofilament protein-H, -M, or L; and
    (e) detecting the level of binding of the second antibody to the biomarker in the biological fluid samples.

11. The method of claim 1, wherein the first biological fluid sample is obtained from the subject within 24 hours of the traumatic injury or the suspected traumatic injury.

12. The method of claim 1, wherein the traumatic injury to the central nervous system is traumatic brain injury or traumatic spinal cord injury.

13. The method of claim 1, wherein the P-Tau is phosphorylated at Thr231, Ser202, Thr205, Thr181, Ser396, Ser404 or any combination thereof, based on the numbering of human Tau 441.

14. The method of claim 1, further comprising:
    (d) obtaining one or more additional biological fluid samples from the subject at later times, contacting the additional biological fluid samples with a first antibody that specifically recognizes the biomarker P-Tau, and detecting the level of binding of the first antibody to the biomarker in the biological fluid samples indicating the traumatic injury to the central nervous system.

15. The method of claim 14, wherein the later times are selected from one or more of 5 days, 14 days, 1 month, 3 months, and 6 months.

16. The method of claim 1, further comprising:
    (d) contacting the biological fluid samples with a second antibody that specifically recognizes the biomarker GFAP; and
    (e) detecting the level of binding of the second antibody to the biomarker in the biological fluid samples.

* * * * *